United States Patent
Shue et al.

[11] Patent Number: 5,798,359
[45] Date of Patent: Aug. 25, 1998

[54] PIPERAZINO DERIVATIVES AS NEUROKININ ANTAGONISTS

[75] Inventors: Ho-Jane Shue, Pine Brook; Neng-Yang Shih, North Caldwell; John Piwinski, Clinton Township; Xiao Chen, Edison; David J. Blythin, North Caldwell, all of N.J.

[73] Assignee: Schering Corporation, Kenilworth, N.J.

[21] Appl. No.: 451,113

[22] Filed: May 25, 1995

Related U.S. Application Data

[62] Division of Ser. No. 432,739, May 2, 1995.

[51] Int. Cl.$^6$ .................. A61K 31/495; A61K 31/395; C07D 401/00; C07D 403/00
[52] U.S. Cl. .................. 514/255; 514/210; 514/212; 540/481; 540/597; 544/359; 544/360; 544/372
[58] Field of Search .................. 544/360, 359, 544/372; 514/255, 210, 212; 540/481, 597

[56] References Cited

U.S. PATENT DOCUMENTS

| | | | |
|---|---|---|---|
| 5,350,852 | 9/1994 | Eonds-Alt et al. | 544/336 |
| 5,464,788 | 11/1995 | Bock et al. | 514/252 |
| 5,589,489 | 12/1996 | Shenvi et al. | 514/323 |
| 5,607,936 | 3/1997 | Chiang et al. | 514/255 |

FOREIGN PATENT DOCUMENTS

| | | |
|---|---|---|
| 0655442 | 5/1995 | European Pat. Off. |
| 9429309 | 12/1994 | WIPO |

*Primary Examiner*—Mukund J. Shah
*Assistant Examiner*—Brenda Coleman
*Attorney, Agent, or Firm*—Anita W. Magatti

[57] ABSTRACT

The invention relates to compounds of the formulas

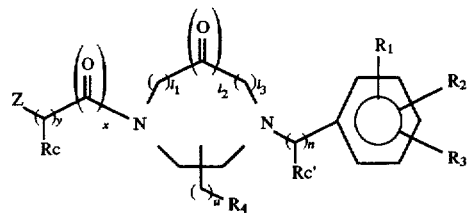

wherein Z, $R_c$, y, x, $l_1$, $l_2$, $l_3$, u, $R_4$, $R_{c'}$, n, $R_1$, $R_2$, and $R_3$, are as described herein. These compounds are neurokinin antagonists. These compounds are useful in the treatment of chronic airway diseases such as asthma.

12 Claims, No Drawings

PIPERAZINO DERIVATIVES AS NEUROKININ ANTAGONISTS

This is a division of application Ser. No. 08/432,739, filed May 2, 1995.

BACKGROUND OF THE INVENTION

The present invention relates to a genus of compounds useful as antagonists of neurokinin receptors. In particular, these can be neurokinin-1 receptor ($NK_1$) antagonists. Some can also be neurokinin-1 receptor ($NK_1$)antagonists and neurokinin-2 receptor ($NK_2$) antagonists, that is, $NK_1/NK_2$ dual receptor antagonists.

Neurokinin receptors are found in the nervous system and the circulatory system and peripheral tissues of mammals, and therefore are involved in a variety of biological processes. Neurokinin receptor antagonists are consequently expected to be useful in the treatment or prevention of various mammalian disease states, for example asthma, cough, bronchospasm, inflammatory diseases such as arthritis, migraine, nociception, and various gastrointestinal disorders such as Crohn's disease.

In particular, $NK_1$ receptors have been reported to be involved in microvascular leakage and mucus secretion, and $NK_2$ receptors have been associated with smooth muscle contraction, making $NK_1$ and $NK_2$ receptor antagonists especially useful in the treatment and prevention of asthma.

SUMMARY OF THE INVENTION

The invention relates to compounds of the formula:

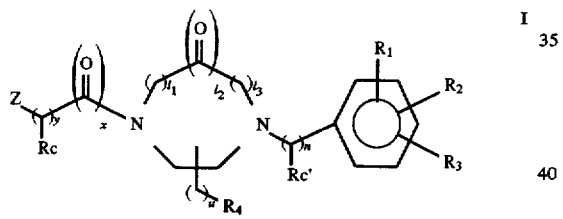

I wherein each $R_1$ is independently

H, $C_1$-$C_6$ alkyl, $CF_3$, $C_2F_5$, $NO_2$, $OR_a$, $-O-C(O)-Ra$,

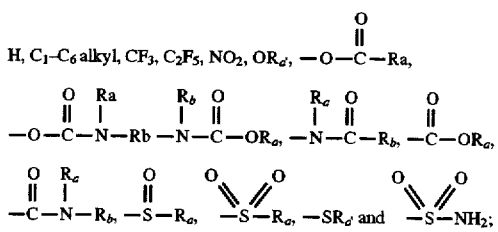

and where $R_a$ is not H

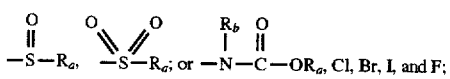

and each $R_2$, and $R_3$ is independently

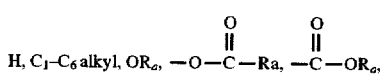

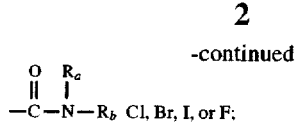

each $R_a$ and $R_b$ is independently selected from the group consisting of H; $C_1$-$C_6$ alkyl, $CF_3$, $C_2F_5$, phenyl, and benzyl;

each $R_c$ and $R_{c'}$ is selected from the group consisting of H, $C_1$-$C_6$ alkyl, $C_2$-$C_6$ alkenyl, $C_2$-$C_6$ alkynyl, unsubstituted or substituted phenyl, and unsubstituted or substituted benzyl, with the proviso that no more than one $R_c$ is other than H in the

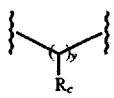

moiety, and no more than one $R_{c'}$ is other than H in the

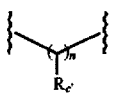

moiety;

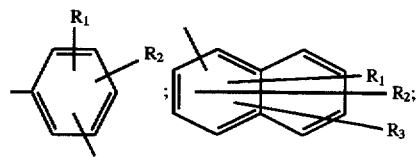

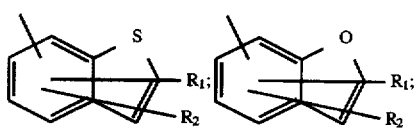

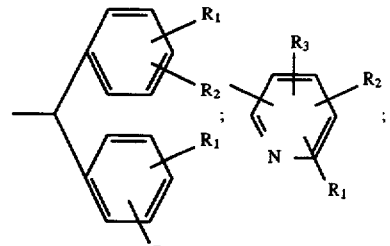

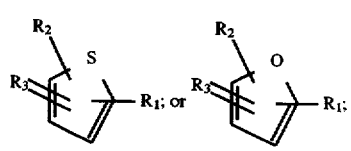

and wherein $l_1$ is 0, $l_2$ is 0, $l_3$ is 2 to 4, and x is 0, and y is 2 to 4; or
x is 1, and y is 0 to 3;
wherein
$l_1$ is 0, $l_2$ is 1, $l_3$ is 1 to 3, and x is 0, and y is 2 to 5; or
wherein
$l_1$ is 1 to 3, $l_2$ is 1, $l_3$ is 0, and x is 0, and y is 2 to 4; or x is 1, and y is 0 to 3;

Z is selected from the group consisting of

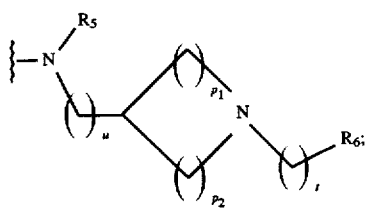

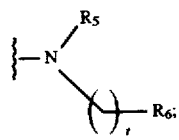

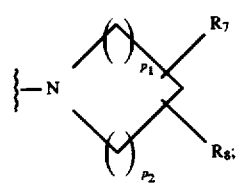

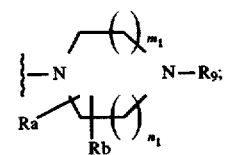

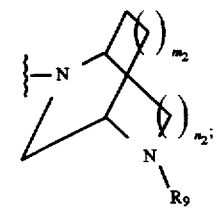

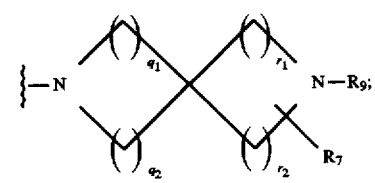

$m_1$ is 1 to 2;

$n_1$ is 1 to 2;

$m_2$ is 0 to 2;

$n_2$ is 1 to 2;

$p_1$ and $p_2$ are each independently 1 to 4 with the proviso that $p_1$ and $p_2$ added together are 2 to 6;

$q_1$ and $q_2$ are integers and each is independently 0 to 4 with the proviso that $q_1$ and $q_2$ added together equal 3 to 5;

$r_1$ and $r_2$ each is independently 0 to 4, with the proviso that $r_1$ and $r_2$ added together are 3 to 5;

each t is 0 to 4;

each u is independently 0 to 2; and $R_5$ is selected from the group consisting of

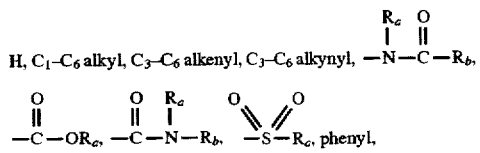

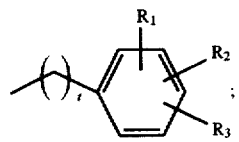

wherein $R_a$ is not H when $R_5$ is

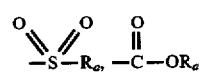

and with the proviso that when $R_5$ is $C_3$–$C_6$ alkenyl or $C_3$–$C_6$ alkynyl, the double or triple bond cannot be directly attached to nitrogen;

$R_6$ is selected from the group consisting of

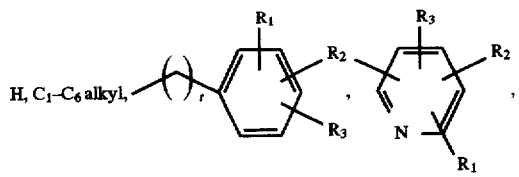

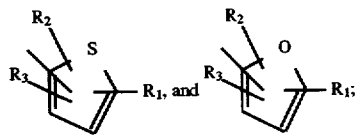

$R_7$, and $R_8$ are each independently selected from the group consisting of

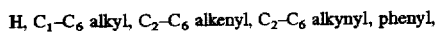

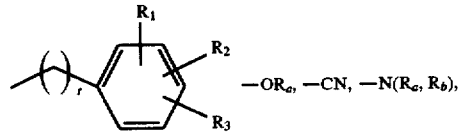

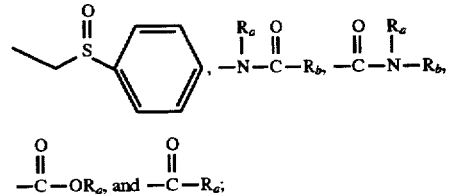

$R_7$, and $R_8$ are each independently selected from the group consisting of

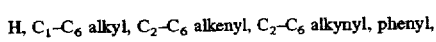

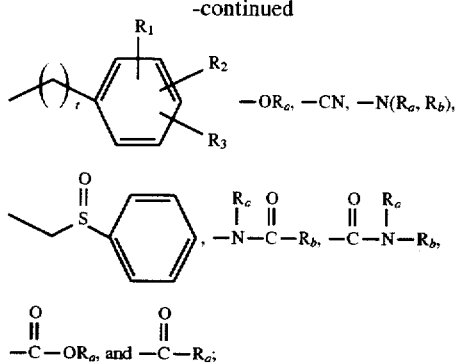

and wherein $R_7$ and $R_8$ can be bonded to the same carbon atom, or $R_7$ and $R_8$ taken together can be a carbonyl group;

and with the proviso that no two groups selected from the group consisting of $-OR_a$ and $-N(R_a,R_b)$, can be bonded to the same carbon atom, and with the further proviso that no group selected from the group consisting of $-OR_a$ and $-N(R_a,R_b)$, can be bonded to a carbon adjacent to a nitrogen atom;

$R_9$ is selected from the group consisting of

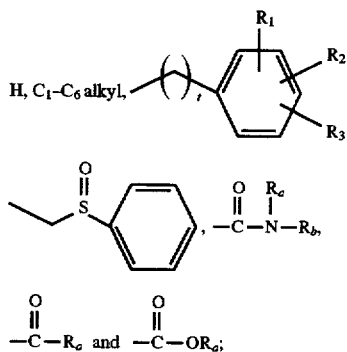

wherein $R_a$ is not H, when $R_9$ is

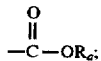

and wherein substituted means 1 to 3 substituents independently selected from the group consisting of H, $C_1$–$C_6$ alkyl, $CF_3$, $C_2F_5$, OH, $OC_1$–$C_6$ alkyl, Cl, Br, I and F;

or a pharmaceutically acceptable salt thereof.

Preferred compounds of the invention are compounds of formula I wherein $l_1$ is 0, $l_2$ is 0, $l_3$ is 2 to 4, and n is 0 to 5; and
x is 0, and y is 2 to 4; or
x is 1, and y is 0 to 3.

Preferred compounds of the invention are compounds of formula I wherein $l_1$ is 0, $l_2$ is 1, $l_3$ is 1 to 3, and
n is 1 to 5, and
x is 0, and y is 2 to 5.

Preferred compounds of the invention are compounds of formula I as described above wherein $l_3$ is 1.

Preferred compounds of the invention are compounds of formula I wherein $l_1$ is 1 to 3, $l_2$ is 1, $l_3$ is 0,
n is 1 to 5; and
x is 0, and y is 2 to 4; or
x is 1, and y is 0 to 3;

A compound according to formula I wherein one of $R_1$, $R_2$, and $R_3$ in the

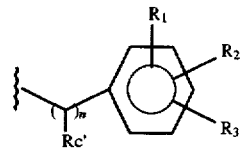

moiety of formula I is H.

A compound according to formula I wherein two of $R_1$, $R_2$, and $R_3$ in the

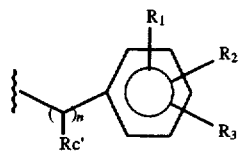

moiety of formula I is H.

A compound according to formula I wherein all of $R_c$ or all of $R_{c'}$ are H.

A compound according to formula I wherein $R_4$ is phenyl or

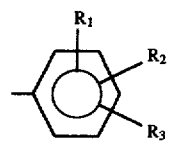

wherein each $R_1$ is independently

H, $C_1$–$C_6$ alkyl, $CF_3$, $C_2F_5$, $NO_2$, $OR_a$, Cl, Br, I, F, $$-O-\overset{O}{\underset{\|}{C}}-R_a,\ -O-\overset{O}{\underset{\|}{C}}-\overset{R_a}{\underset{|}{N}}-R_b,\ -\overset{R_b}{\underset{|}{N}}-\overset{O}{\underset{\|}{C}}-OR_a,$$

$$-\overset{R_a}{\underset{|}{N}}-\overset{O}{\underset{\|}{C}}-R_b,\ -\overset{O}{\underset{\|}{C}}-OR_a,\ -\overset{O}{\underset{\|}{C}}-\overset{R_a}{\underset{|}{N}}-R_b,\ -\overset{O}{\underset{\|}{S}}-R_a,$$

$$-\overset{O}{\underset{\diagdown}{S}}\!\!\diagup\!\!\overset{O}{R_a},\ -SR_a,\text{ and }-\overset{O}{\underset{\diagdown}{S}}\!\!\diagup\!\!\overset{O}{NH_2};$$

and where $R_a$ is not H in $$-\overset{O}{\underset{\|}{S}}-R_a,\ -\overset{O}{\underset{\diagdown}{S}}\!\!\diagup\!\!\overset{O}{R_a};\text{ or }-\overset{R_b}{\underset{|}{N}}-\overset{O}{\underset{\|}{C}}-OR_a,$$

and each $R_2$, and $R_3$ can be independently

H, $C_1$–$C_6$ alkyl, $OR_a$, $-O-\overset{O}{\underset{\|}{C}}-R_a$, $-\overset{O}{\underset{\|}{C}}-OR_a$, $-\overset{O}{\underset{\|}{C}}-\overset{R_a}{\underset{|}{N}}-R_b$ Cl, Br, I, or F;

and each $R_a$ and $R_b$ is independently selected from the group consisting of H; $C_1$–$C_6$ alkyl, $CF_3$, $C_2F_5$, phenyl, and benzyl.

A compound according to formula I wherein Z is

A compound according to formula I wherein Z is

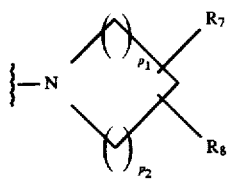

A compound according to formula I wherein Z is

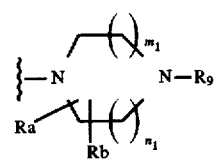

A compound according to formula I wherein Z is

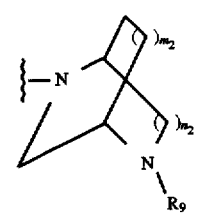

A compound according to formula I wherein $R_5$ is H, $C_1$–$C_5$ alkyl, or

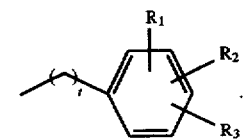

A compound according to formula I wherein $R_6$ is H, $C_1$–$C_5$ alkyl, or

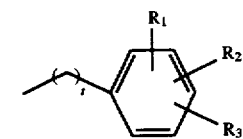

A compound according to formula I wherein $R_7$ is H, $C_1$–$C_5$ alkyl, or

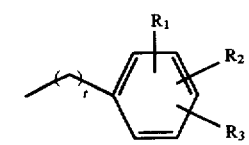

A compound according to formula I wherein $R_8$ is H, $C_1$–$C_5$ alkyl, or

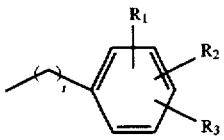

A compound according to formula I wherein $R_9$ is H, $C_1$–$C_5$ alkyl, or

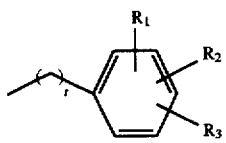

A compound according to formula I wherein one of $R_1$, $R_2$, $R_3$ is H, Z is Q, R, or S all of $R_c$ and $R_{c'}$ are H and $R_4$ is substituted or unsubstituted phenyl, $l_1$ and $l_2$ are 0–3 is 2; x, y, and n are 1; and u is 0.

Exemplary compounds of the invention are compounds of the formulas:

A compound according to claim 1 selected from the group consisting of

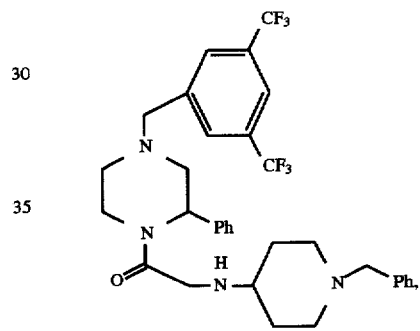

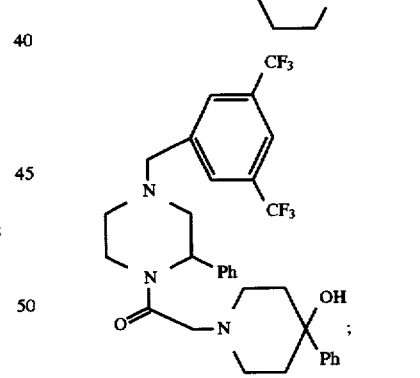

or a compound selected from the group consisting of

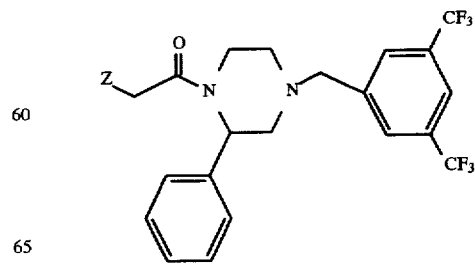

wherein Z is
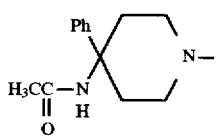
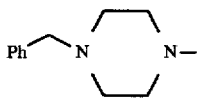
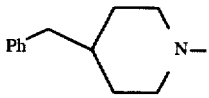
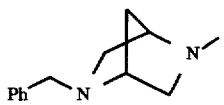
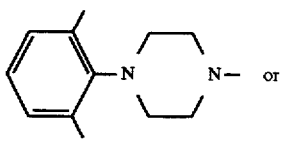 or
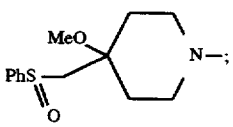
or a compound selected from the group consisting of
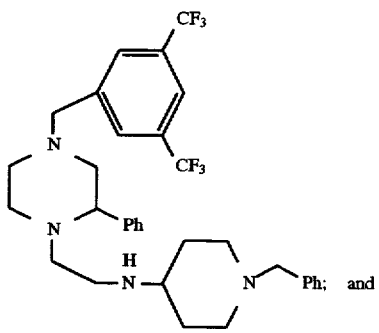
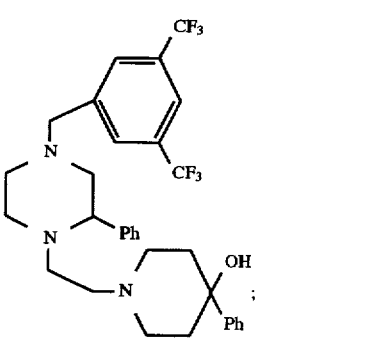
or a compound selected from the group consisting of
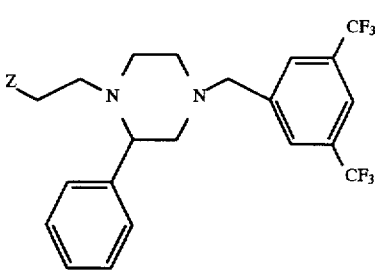
wherein Z is
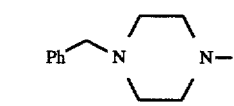
or
or a compound selected from the group consisting of
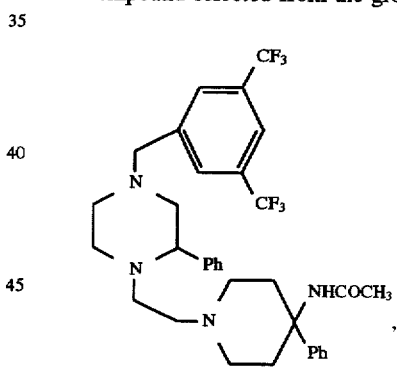
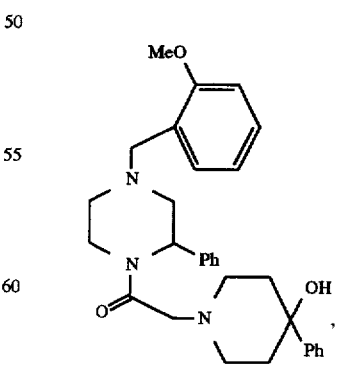

-continued or a compound selected from the group consisting of wherein Z is or a compound selected from the group consisting of
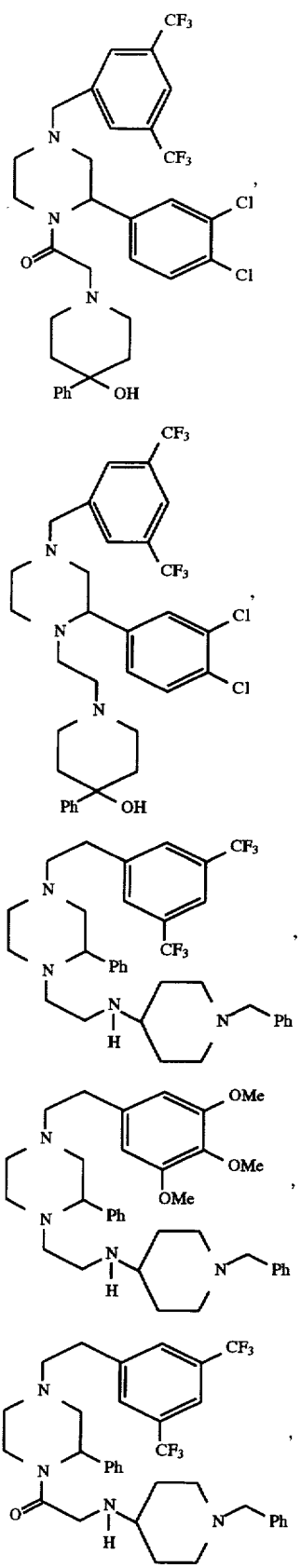
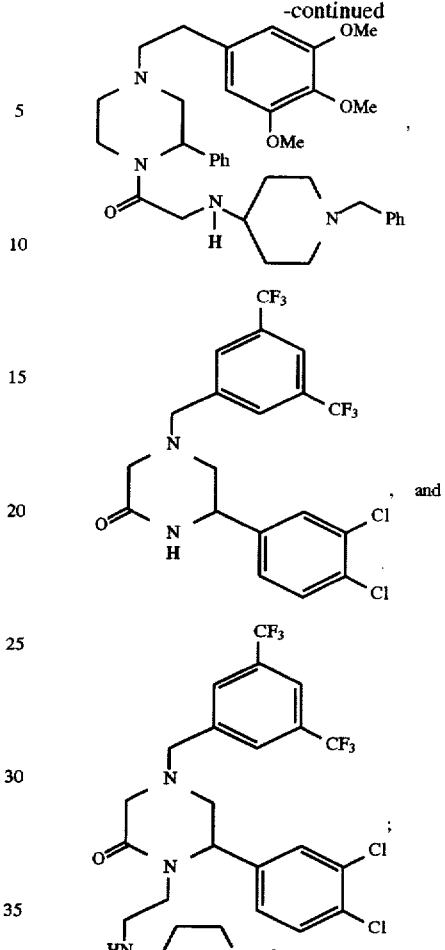
or a compound selected from the group consisting of
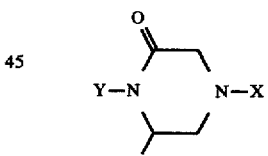
wherein Ar is
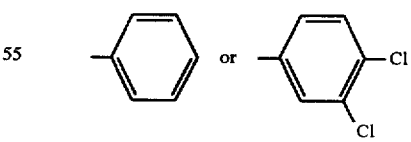
and wherein X is and Y is
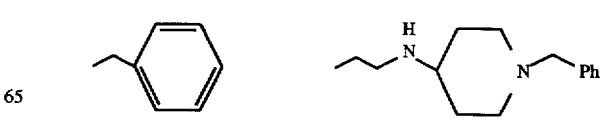

-continued
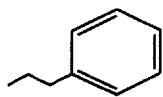 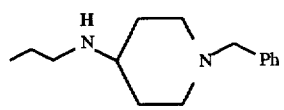
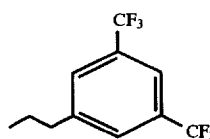 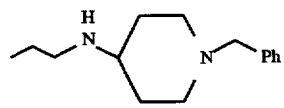
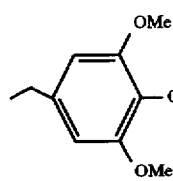 
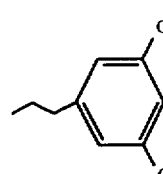 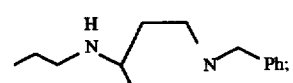
or a compound selected from the group consisting of
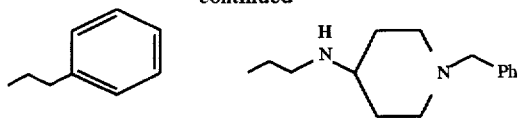
wherein Ar is
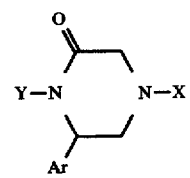
wherein X is and Y is
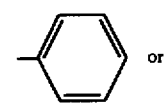 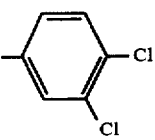
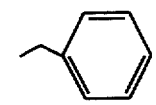 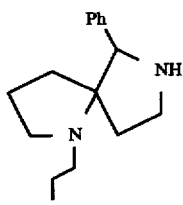
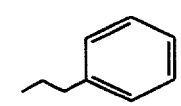 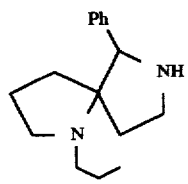
-continued
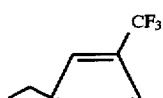 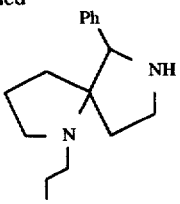
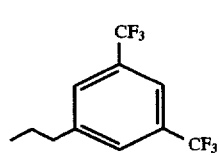 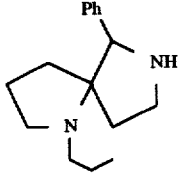
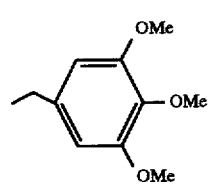 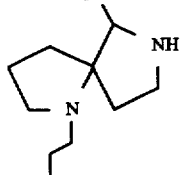
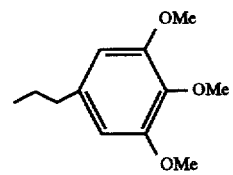 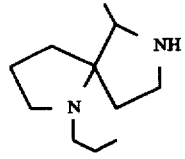
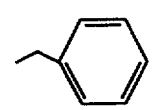 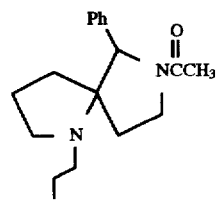
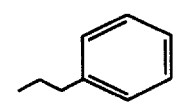 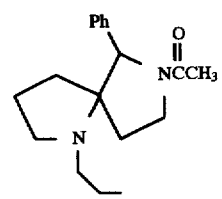
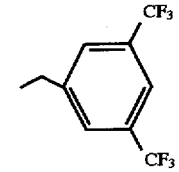 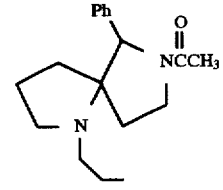
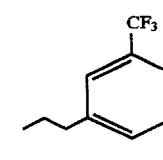 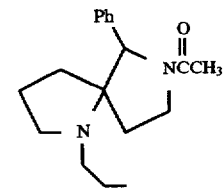

or a compound selected from the group consisting of wherein Ar is phenyl or 3,4-dichlorophenyl wherein A is and Z is or a compound selected from the group consisting of wherein X is and wherein X is and Y is -continued
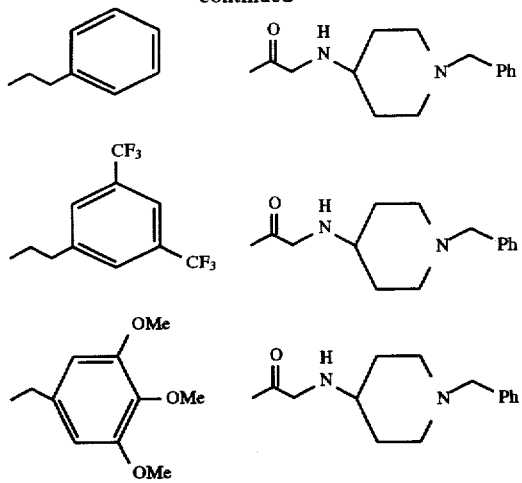
and
or a compound selected from the group consisting of
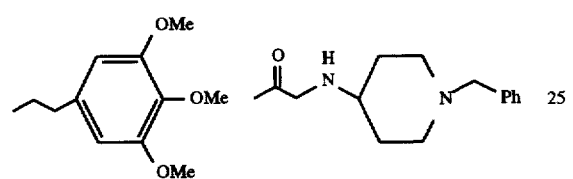 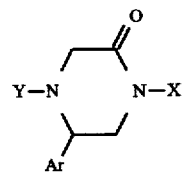
wherein Ar is
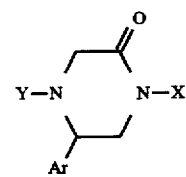
and wherein X is and Y is
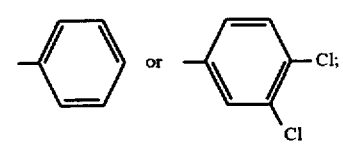
-continued
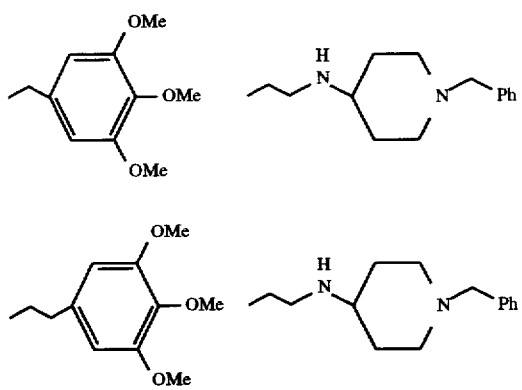
or a compound selected from the group consisting of
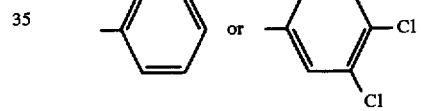
wherein Ar is
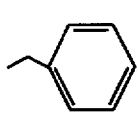 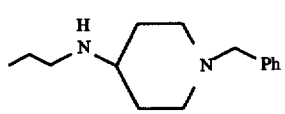
and wherein X is and Y is
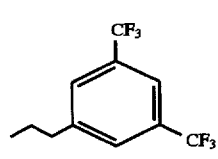 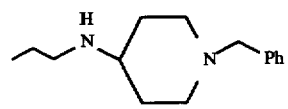
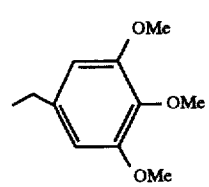 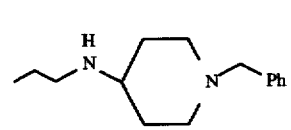
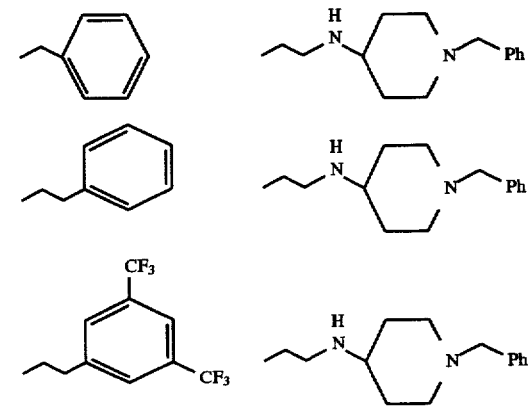

-continued
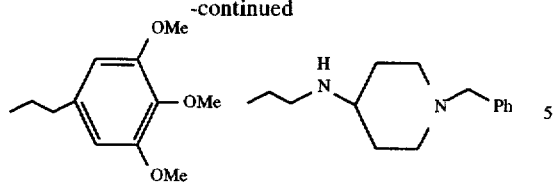
or a compound selected from the group consisting of
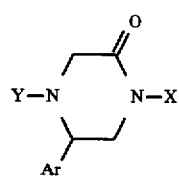
wherein Ar is
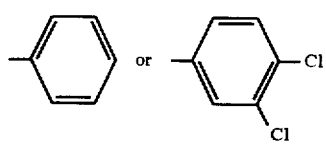
and wherein X is and Y is
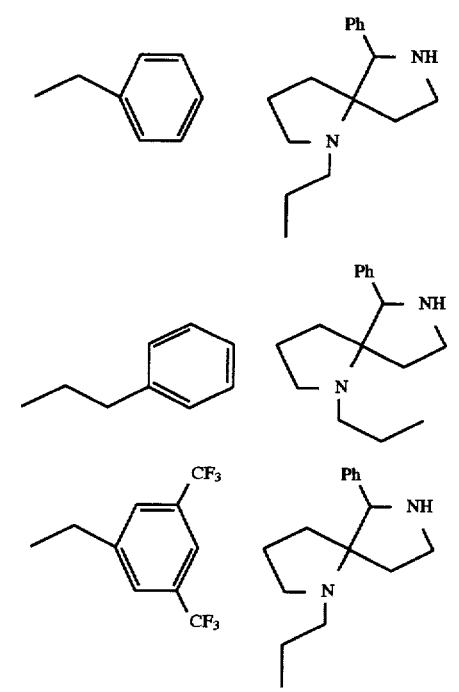
-continued
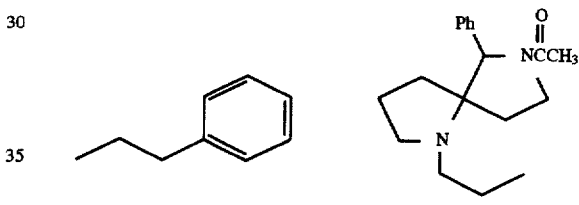
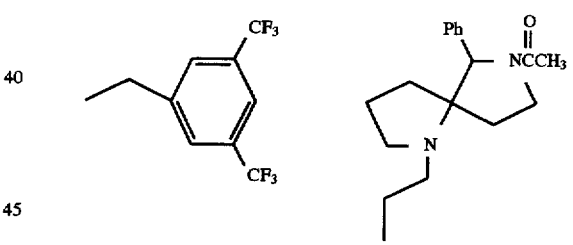
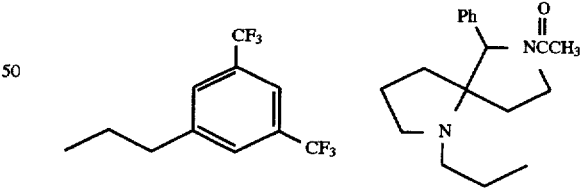
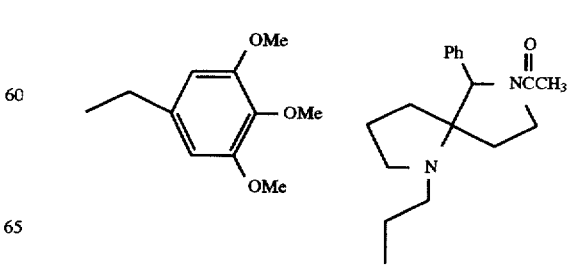

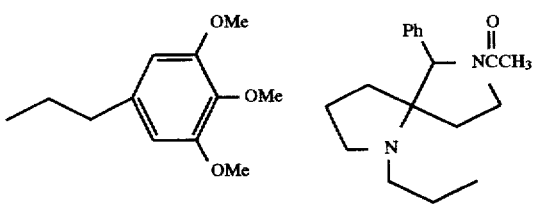

or a pharmaceutically acceptable salt thereof.

The invention also relates to a pharmaceutical composition comprising a thereapeutically effective amount of a compound of formula I in combination with a pharmaceutically acceptable carrier.

The invention also relates to a method for treating chronic airway diseases such as asthma and allergies; inflammatory diseases such as inflammatory bowel disease, psoriasis, fibrositos, osteoarthritis, and rheumatoid arthritis; migraine; central nervous system disorders such as depression, psychosis, dementia, and Alzheimer's disease; Down's syndrome; neuropathy; multiple sclerosis; ophthalmic disorders; conjunctivitis; auto immune disorders; graft rejection; systemic lupus erythematosus; GI disorders such as Crohn's disease and ulcerative colitis; disorders of bladder function; circulatory disorders such as angina; Raynaud's disease; coughing and pain. In particular, the invention also relates to a method of treating asthma which comprises administering to a mammal in need of such treatment an anti-asthma effective amount of a compound of formula I for such purpose.

DETAILED DESCRIPTION OF THE INVENTION

As used herein the term alkyl means a straight or branched, saturated hydrocarbon chain having from 1 to 6 carbon atoms. The number of carbon atoms may be designated. For example, "$C_1$-$C_6$ alkyl" represents a straight or branched, saturated hydrocarbon having from 1 to 6 carbon atoms.

The term alkenyl means means a straight or branched, saturated alkenyl having from 2 to 6 carbon atoms. The number of carbon atoms may be designated. For example, "$C_2$-$C_6$ alkenyl" represents a straight or branched alkenyl having from 1 to 6 carbon atoms.

The term alkynyl means a straight or branched, saturated alkynyl having from 2 to 6 carbon atoms. The number of carbon atoms may be designated. For example, "$C_2$-$C_6$ alkynyl" represents a straight or branched chain alkynyl having from 2 to 6 carbon atoms.

As used herein, a heavy dark line (━) denotes a chemical bond coming above the plane of the page. A dashed line (┅) denotes a chemical bond coming below the plane of the page.

As used herein,

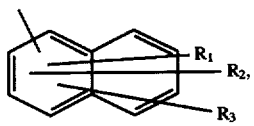

for example, means that $R_1$, $R_2$, and $R_3$ can be in either of the rings of the above naphthyl moiety.

Asymetric centers exist in compounds of formula I of the invention. Accordingly, compounds of formula I include stereoisomers.

All such isomeric forms and mixtures thereof are within the scope of the present invention. Unless otherwise indicated, the methods of preparation disclosed herein may result in product distributions which include all possible structural isomers, although it is understood that physiological response may vary according to stereochemical structure. The isomers may be separated by conventional means such as fractional crystallization, preparative plate or column chromatography on silica, alumina, or reversed phase supports or HPLC (high performance liquid chromatography).

Enantiomers may be separated, where appropriate, by derivatization or salt formation with an optically pure reagent, followed by separation by one of the aforementioned methods. Alternatively, enantiomers may be separated by chromatography on a chiral support.

The compounds of formula I can exist in unsolvated as well as solvated forms, including hydrated forms, e.g. the hemihydrate. In general, the solvated forms, with pharmaceutically acceptable solvents such as water, ethanol, and the like are equivalent to the unsolvated forms for the purposes of the invention.

Those compounds of formula I which contain a basic group such as —$CH_2NH_2$, form pharmaceutically acceptable salts. The preferred pharmaceutically acceptable salts are nontoxic acid addition salts formed by adding to a suitable compound of the invention about a stoichiometric amount of a mineral acid, such as HCl, HBr, $H_2SO_4$ or $H_3PO_4$ or of an organic acid such as acetic, propionic, valeric, oleic, palmitic, stearic, lauric, benzoic, lactic, para-toluenesulfonic, methane sulfonic, citric, maleic, fumaric, succinic and the like, respectively.

GENERAL METHODS OF PREPARATION

The compounds of this invention may be prepared by one of the following general methods. As used herein RT means room temperature. Unless otherwise indicated, variables in the structural formulas below are as defined above.

Method 1.

If the group $R_4$ is an aromatic group with no I or Br substituents, $l_1$ and $l_2$ are all 0, and $l_3$ is 2, then the following method may be used to prepare the useful intermediates (IV):

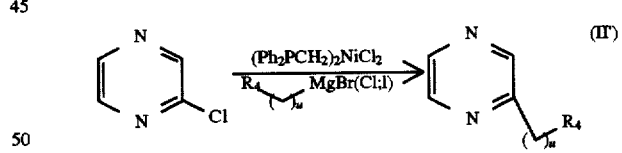

Transition metal catalyzed coupling of 2-chloropyrazine with an aromatic Grignard reagent in a dry, ether solvent, such as THF, yields the aryl-substituted pyrazine of formula II'. The catalyst shown, [1,2-bis-(diphenylphosphino) ethane]nickel[II] chloride, is a preferred reagent for this transformation. Where $R_4$ has no halo substituents, reduction of a compound of formula II' by catalytic hydrogenation, using, for instance, palladium acetate, preferably in acetic acid solvent, results in preferential reduction of the pyrazine ring, leaving the aromatic ring unreduced, that is, it results in a compound of formula II. Similarly, 10% Pd on charcoal (Pd—C) can be used in an alcohol solvent, preferably methanol, with or without the addition of a small quantity (1 to 5 equivalents.) of acetic acid. Reaction times of from 1 to 24 hours generally suffice for this reaction, which is preferentially run at room temperature or slightly above (up to about 50° C.) and using from 1 to about 6 atmospheres pressure of hydrogen.

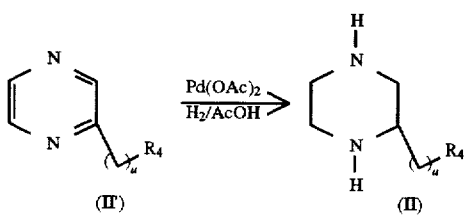

The intermediate of formula II may also be prepared from a compound of formula II', even if the group R$_4$ contains halogen atoms, by reduction using a strong hydride ion donor, preferably lithium aluminum hydride (LAH) or diisobutyl aluminum hydrate (DIBAL-H) in an ether solvent, such as ether, THF or dimethoxyethane (DME).

Selective alkylation of a compound of formula II is possible using low temperature conditions. Thus, reacting a compound of formula II with a substituted aryl-alkyl halide of formula III results in the formation of the 4-substituted derivative of formula IV. Suitable conditions include use of a halogenated solvent, such as CH$_2$Cl$_2$, at low temperature. Suitable temperatures are from −78° C. initially, allowing the reaction mixture to warm gradually to RT if the reaction is not completed after several hours. The reaction is catalyzed by the addition of an equivalent amount of an organic base, such as triethylamine and diisopropylethylamine (Hunig's base).

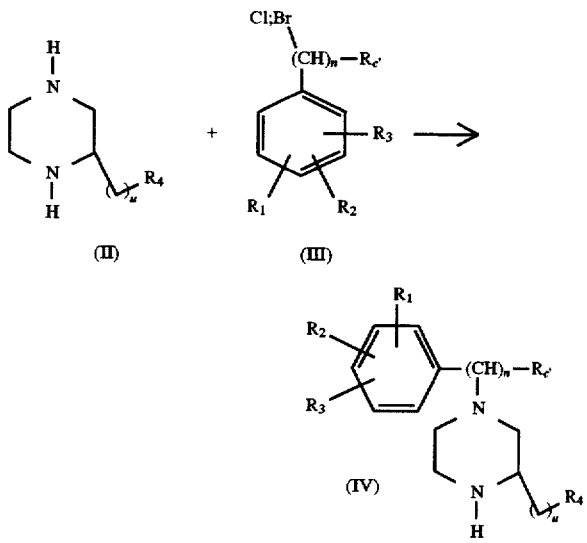

Method 2.

If the group R$_4$ contains one or more halogen atoms on an aromatic ring and the other groups are as in Method 1, then an alternate route to a compound of formula IV is preferred. In addition, this method can be used to prepare compounds in which l$_1$ and l$_2$ are both zero, and l$_3$ is from 2 to 4. Mono-protection of the diamine of formula (A), preferably with BOC anhydride, or other agents known to introduce the t-butyloxycarbonyl protecting group, in an alcohol solvent, such as methanol, preferably at about −10° C., produces a compound of formula V.

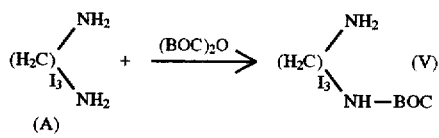

These compounds are used to perform a reductive amination reaction with the aldehyde of formula VI to produce an amine of formula VII.

Suitable conditions for this type of reaction include the use of an alcohol solvent, preferably methanol, made slightly acidic with a weak organic acid, such as acetic acid, and a reducing agent known to favor reductive amination reactions, preferably sodium cyanoborohydride, NaBH$_3$CN.

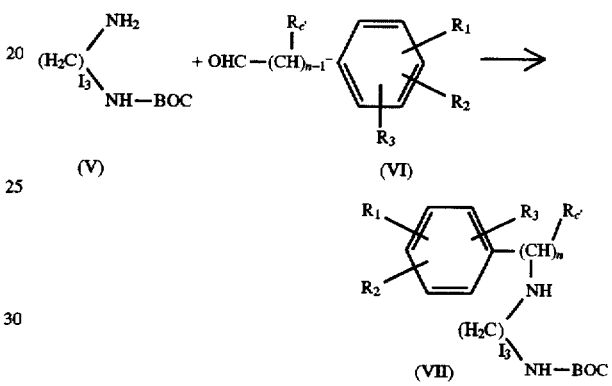

Reaction of a compound of formula VII with a phenacyl halide derivative of formula VIII, in which R$_4$ preferably represents a halogenated aromatic ring, but may be any of the claimed aromatic rings, in the presence of an organic base, such as di-isopropylethylamine, also known as Hunig's Base, in an ether solvent, such as THF, results in the formation of the intermediates of formula IX.

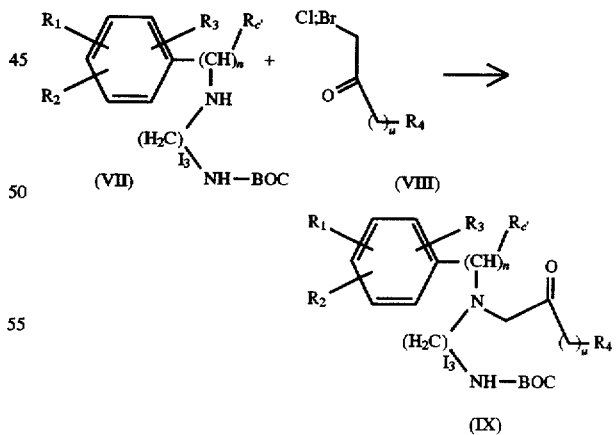

Removal of the BOC protecting group using a suitable acidic catalyst, such as trifluoroacetic acid, followed by an intramolecular reductive amination, under conditions such as those described above for the preparation of a compound of formula VII, leads to the formation of compounds of formula IVA.

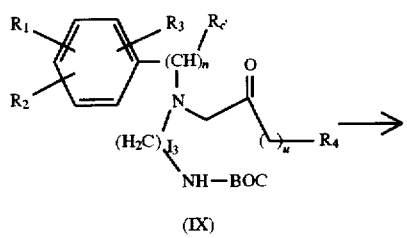

(IX)

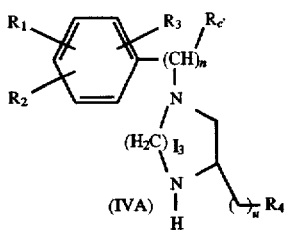

(IVA)

Method 3.

An alternate route to compounds of the invention in which $l_1, l_2$ and m are 0, and $l_3$ is 2 is as follows. Standard coupling of an N-protected amino acid of formula X, wherein such as $R_4$—CH(NHProt)CO$_2$H, with a glycine ester, (for instance the ethyl ester of formula XI), produces a dipeptide of formula XII. A suitable protecting group is BOC, although many others may also be used. Other esters of glycine may also be used. Standard coupling techniques may be applied, an example being the use of N-hydroxybenztriazole (HOBT) and a water-soluble carbodiimide, such as 1-(3-dimethylaminopropyl)-3-ethylcarbodiimide (DEC), in a non-hydroxylic solvent such as DMF or DMA. The reaction is run, preferably, at or below RT, and takes from 1 to 40 hours for completion, depending upon the substrates.

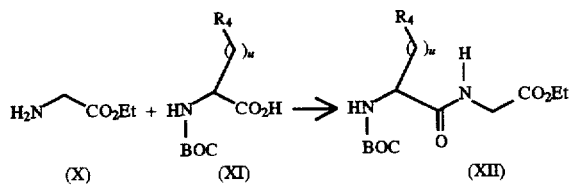

Removal of the protecting group under standard conditions, followed by treatment of the product with a base results in cyclization to the diketopiperazine of formula XIII. Suitable conditions for removal of the exemplified BOC group are well known in the art and include catalysis by trifluoroacetic acid (TFA). A suitable base for cyclization is the alkali metal salt of an alcohol in the alcohol itself used as solvent. For example, a solution of sodium ethoxide in ethanol may be used. The temperature is preferably around RT but may be slightly above or below, in the range 0° C. to about 40° C. The reaction is generally complete within a few hours. Suitable reaction times are from 1 to 24 hours.

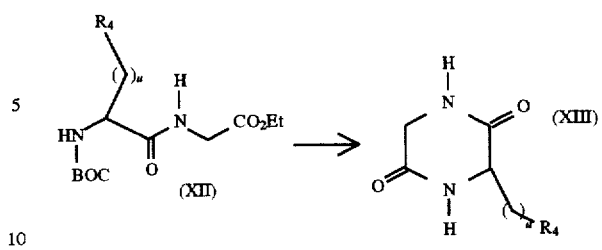

Reduction of the diketopiperazine of formula XIII may be accomplished preferentially with a strong hydride reducing agent, such as LAH or a solution of sodium bis(2-methoxyethoxy)aluminum hydride in toluene (also known as Red-Al®). Suitable solvents for this reaction are DME and other higher boiling ethers since the reaction is run at elevated temperatures, from about 50° C. to about 110° C., preferably at about 90° C.

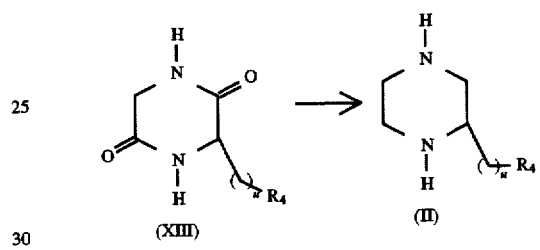

A compound of formula II may be converted to a compound of formula IV by the processes described in Method 1.

Method 4.

The intermediates of formula IV or IVA, formed via any of the previous methods, may be further processed as follows. A compound of formula IV will be used in the Schemes but it should be understood that compounds of formula IVA may also be used in the same way. Reaction of a compound of formula IV with an activated halo-acid, generally the acid halide of formula XIV, in which Hal represents Cl, Br, or I, yields the acylated derivative of formula XV. An organic base is used to take up the hydrogen halide formed in the reaction, suitable bases being triethylamine (TEA) and Hünig's Base. Suitable reaction media include halogenated solvents, such as methylene chloride and chloroform. The reaction is preferably run at low temperature, at least initially. Suitable temperatures are in the region of −50° C. down to −80° C. Later in the reaction it may be desirable to allow the mixture to warm up to about RT to ensure completion of the reaction.

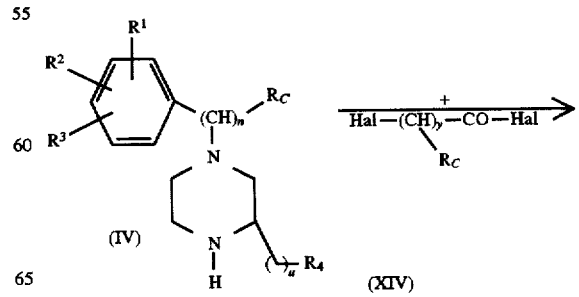

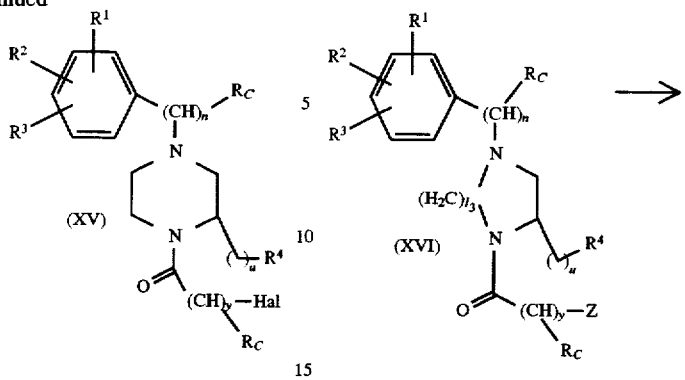

Reaction of the halogenated amides of formula XV with an amine of formula Z—H results in formation of the products of formula XVI, which are compounds of the invention. Compounds of formula of XVI have been modified to show the fact that these products could have been prepared from compounds of formula IVA as well as from IV. Suitable solvents for this reaction are halogenated hydrocarbons, such as methylene chloride, and an organic base is present to absorb the H-Hal formed. Appropriate bases include Hünig's Base. The reaction is performed at or around RT, a suitable temperature being generally in the range of from 0° C. to 40° C. Reaction is complete within 1 to 48 hours.

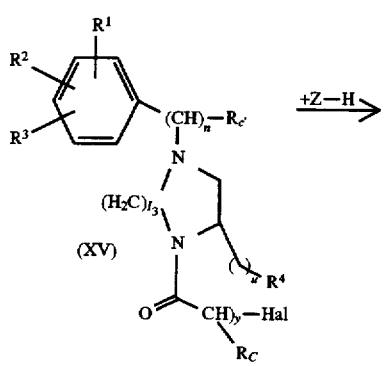

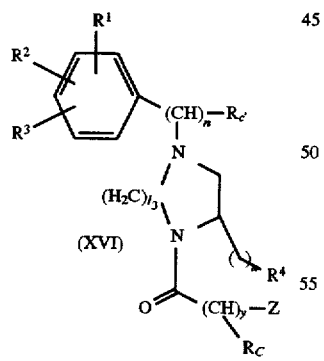

Method 5.

Compounds of formula XVI where y≠0 may be converted to other compounds of the invention of formula XVII by reduction under controlled conditions. It should be realized that the value of y is different in formulas XVI and XVII. In formula XVI, where x=1, y=1 to 4, but in formula XVII, where x=0, y=2 to 5.

Suitable reducing agents to effect this transformation include the borane-dimethyl sulfide complex, as well as other less selective reagents, such as LAH, (assuming that no other group reactive to LAH is present), Red-Al®, and diborane in ether. Effective temperatures for the borane-dimethylsulfide complex to reduce compounds of formula XVI, range from RT to the reflux temperature of the solution of the reagent in THF (about 80° C.).

Method 6.

Intermediates of the formula XVIII may be selectively acylated by coupling with an acid of the formula XIX. Standard coupling techniques may be applied, an example being the use of HOBT, a water-soluble carbodiimide, such as DEC, and an organic base, such as triethylamine, in a non-hydroxylic solvent, such as $CH_2Cl_2$, at a temperature of about −20° C. initially. The mixture may be allowed to warm to RT to complete the reaction. The product of reaction is the amide of formula XX.

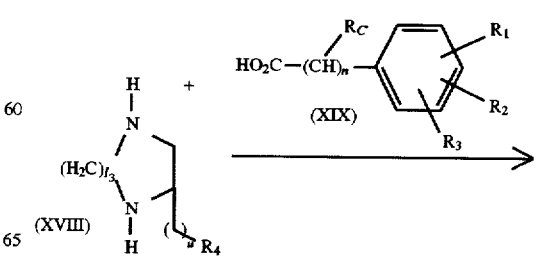

-continued

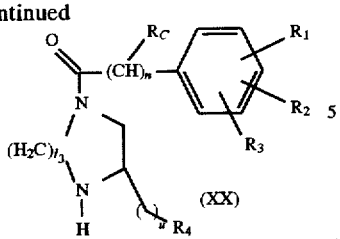

(XX)

Compounds of the formula XX, may be further acylated using an acid halide of formula XXI. The reaction is run, preferably at about −78° C., over a period of 1 to 12 hours, in a halogenated solvent, such as methylene chloride or similar solvent. An organic tertiary amine is used to absorb the H-Hal produced in the reaction. Suitable amines include triethylamine and Hünig's Base.

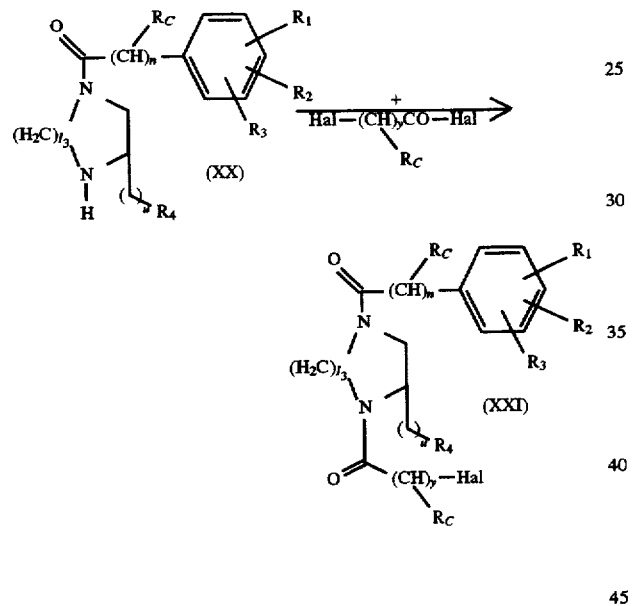

The compounds of formula XXI may be used for further reaction without isolation. Additional organic base, for instance, Hünig's Base, is added to the mixture followed by Z—H, at around −78° C. The reaction is completed by allowing the mixture to warm to RT overnight yielding the compounds of formula XXII after work-up and purification by standard methods.

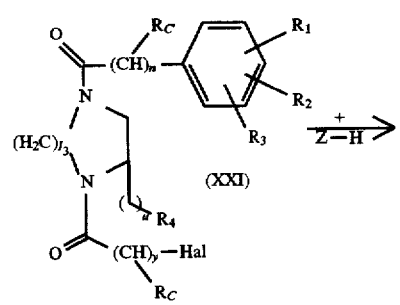

-continued

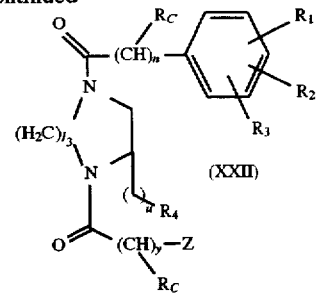

(XXII)

The compounds of formula XXII, in which y≠0 may be converted to other compounds of the invention of formula XXIII by reduction under controlled conditions. It should be realized that the value of n and y are different in compounds of formulas XXII and XXIII. In of formula XXII, where x=1, n=0–4 and y=1–4. In formula XXIII, where x=0, n=1–5 and y=2–5.

Suitable reducing agents to effect this transformation include the borane-methyl sulfide complex, as well as other less selective reagents, such as LAH, Red-Al®, and diborane in ether or other unreactive solvents, such as THF. Using the borane-methyl sulfide complex in THF, at the reflux temperature of the solution, which is about 80° C., the reaction is complete in about 2 hours to 48 hours depending on the precise substrate.

Method 7.

The acylated derivatives of formula XX from Method 6 may be reduced to the saturated alkyl chain derivatives of formula XXIV. As in previous reactions where a carbonyl group is reduced to a —CH₂— group the value of n is different in starting material and product. In formula XX where n=0–4, whereas in formula XXIV where n =1–5.

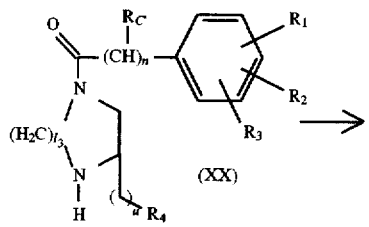

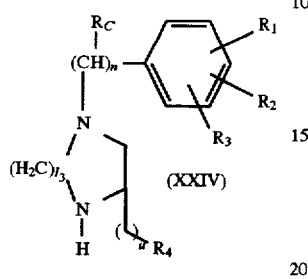

The process to conduct this conversion is the same as described in Method 6 for conversion a compound of formula XXII to a compound of formula XXIII. The reagent of preference is the borane-methyl sulfide complex.

Reaction of the intermediate of formula XXIV with the acyl halide of formula XXV at temperatures of about −78° C. produces the amides of formula XXVI. The reaction is run in a halogenated solvent, such as methylene chloride, in the presence of an organic base to take up the H-Hal formed. A suitable base is Hünig's Base. This product may be used without isolation in the subsequent step.

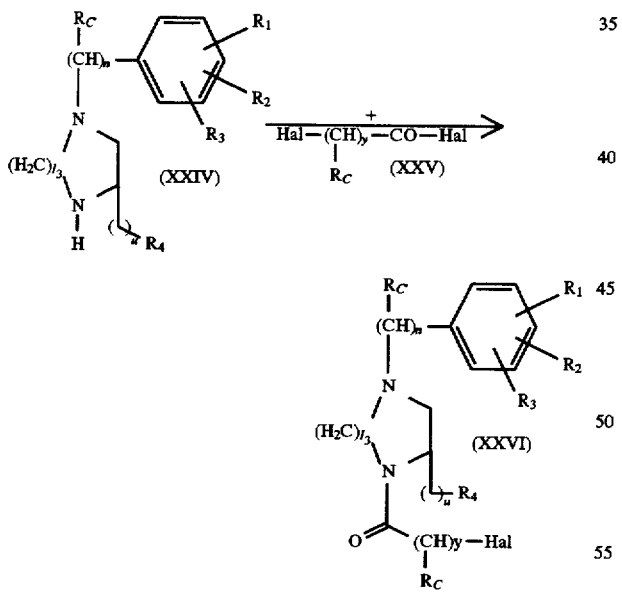

The halo-derivative of formula XXVI may be used without isolation to react with the amine compound of formula Z—H. An additional equivalent amount of a suitable organic base, such as Hünig's Base, is added to the mixture to consume H-Hal. The reaction is initially run at about −78° C. but is allowed to warm gradually to RT to complete the reaction. The product, compound of formula XXVII, is isolated by conventional techniques and may be purified by flash chromatography.

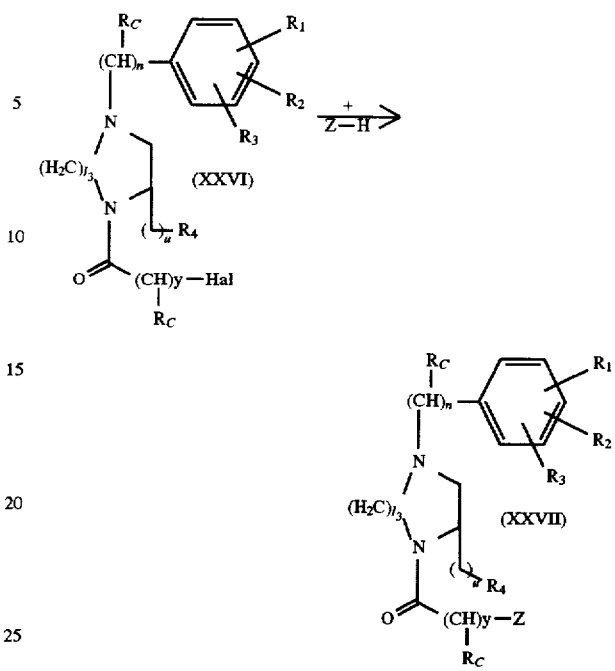

Method 8.

For compounds of claim 1 in which $l_1$ is 1–3, $l_2$ is 1, and $l_3$ is 0 the following scheme may be used. Reaction of the protected amino acid of formula XXVIII with the amino-alcohol of formula XXIX yields the protected amide compound of formula XXX. A suitable protecting group is the BOC group, which is known to be resistant to hydrolysis under basic conditions. Others, such as the carbobenzyloxy (Cbz) group may also be used. Coupling conditions similar to those employed in Method 3 (HOBT/DEC) may be used to effect this coupling reaction.

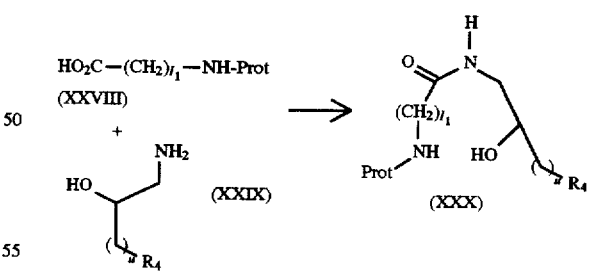

Cyclization of a compound of formula XXX may be accomplished with concomitant loss of the protecting group. Warming a compound of formula XXX with a mixture of acetic acid or trifluoroacetic acid and acetic anhydride results in cyclization with loss of the protecting group to produce a compound of formula XXXI. Suitable temperatures for this reaction are from 40° C. to 100° C.

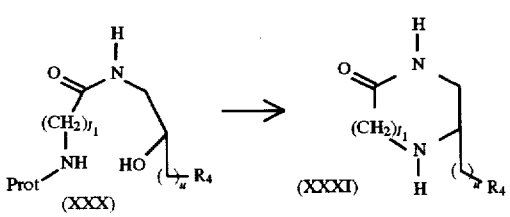

Protection of the amine nitrogen of formula XXXI is then accomplished under standard conditions. Suitable reagents include di-t-butyl dicarbonate, to produce the BOC derivative, and benzyl chloroformate to produce the Cbz derivative. Other protecting groups, made under standard conditions may also be used. Alkylation of the amide is carried out using one of a variety of conditions. Representative reagents for the conversion of a compound of formula XXXII to a compound of formula XXXIII, using the alkylating agent of formula XXXIV, or an equivalent, such as the mesylate or tosylate instead of the Hal derivative, include NaH in DMF or DMA, and anhydrous $K_2CO_3$ or $Cs_2CO_3$ in DMF. Suitable temperatures for the reaction with NaH are from 0° C. to 50° C., and for the other reagents from RT to about 120° C., depending on the precise substrates.

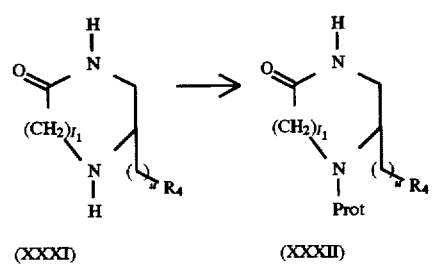

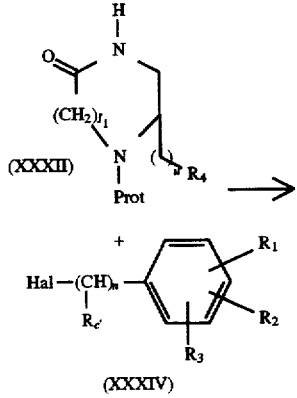

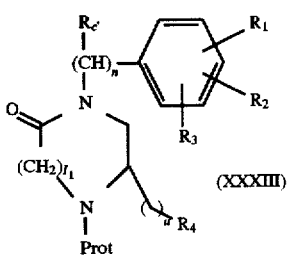

Removal of the protecting group under standard conditions then releases the free amine of formula XXXV which may be acylated at low temperature, for instance, as described in Method 4, using the halo-acid halide of formula XXXVI to produce the halo-derivative of formula XXXVII. This product may be used without isolation for the next step.

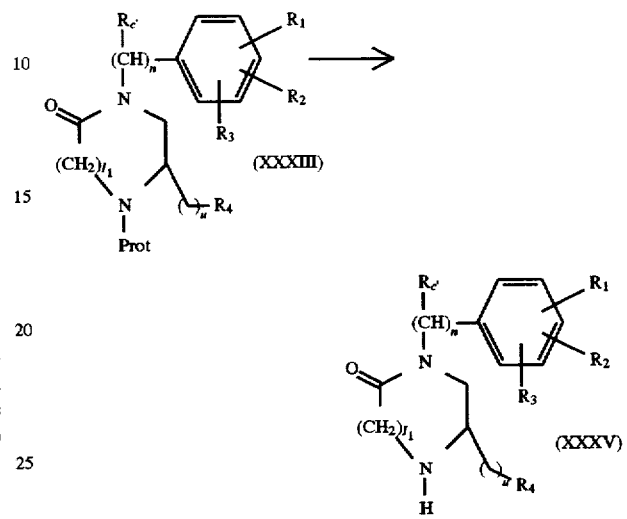

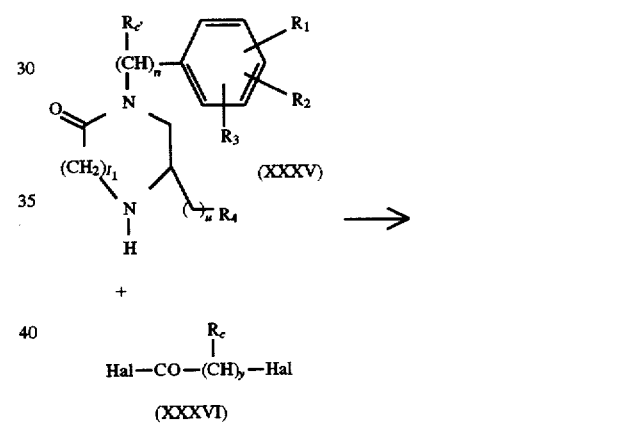

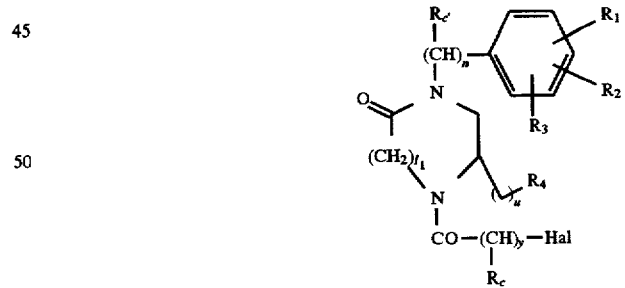

Treatment of the halo-derivative of formula XXXVII with Z—H in the presence of an organic base, under the same conditions as described in Method 6, results in products of formula XXXVIII which are compounds of the invention.

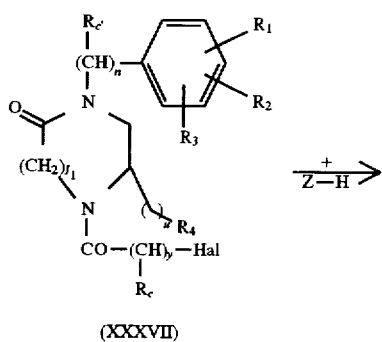

(XXXVII)

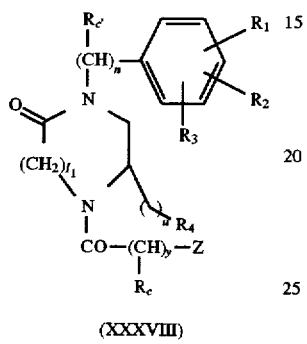

(XXXVIII)

Method 9.

Reaction of a 2-substituted ethylene diamine of formula XXXIX with an α-halo-ester of formula XL in the presence of an organic base, such as Hünig's Base, results in the formation, preferentially, of the derivative of formula XLI. The reaction is run at as low a temperature as possible conducive with a reasonable reaction rate. Temperatures in the range of −20° C. to 40° C. are preferred. Cyclization of this intermediate under basic conditions produces the ring system of a compound of formula XLII. In a compound of formula XL, the ester function, there defined as ethyl, may be any readily available ester that is not highly sterically hindered, such as methyl, n-propyl, or benzyl, instead of ethyl. A compound of formula XLI may be separated from any isomeric product, formed by reaction with the more hindered amino group, by conventional means, such as crystallization or flash chromatography. Suitable bases for the cyclization include alkali metal alkoxides in the respective alcohol, for example, sodium ethoxide in ethanol.

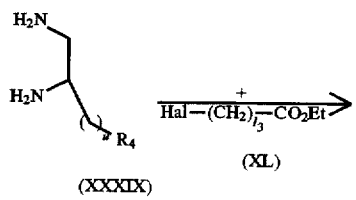

(XXXIX)

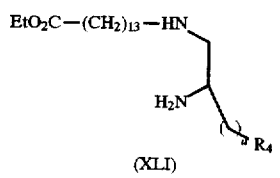

(XLI)

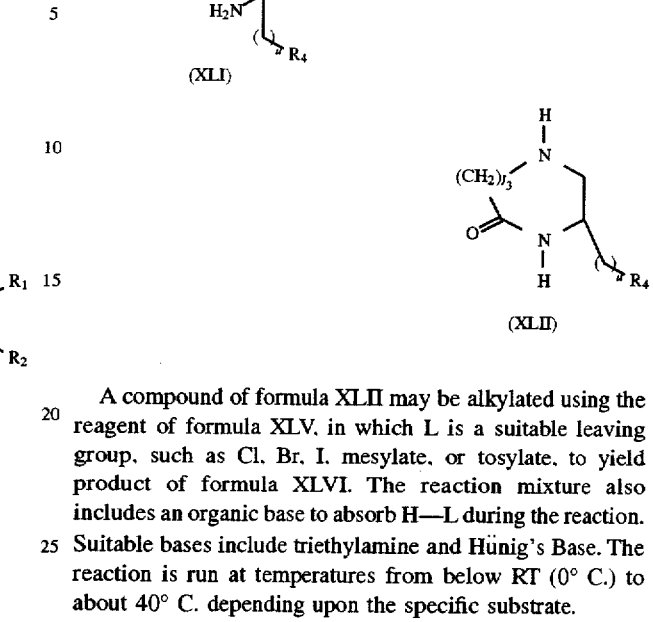

(XLI)

(XLII)

A compound of formula XLII may be alkylated using the reagent of formula XLV, in which L is a suitable leaving group, such as Cl, Br, I, mesylate, or tosylate, to yield product of formula XLVI. The reaction mixture also includes an organic base to absorb H—L during the reaction. Suitable bases include triethylamine and Hünig's Base. The reaction is run at temperatures from below RT (0° C.) to about 40° C. depending upon the specific substrate.

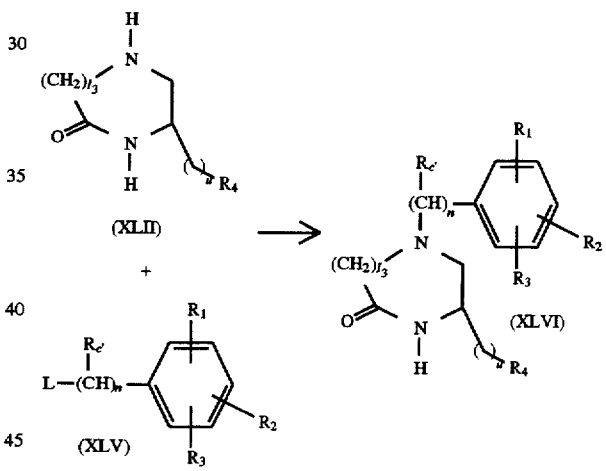

(XLII)

(XLV)

(XLVI)

The compounds of formula XLVI may be further alkylated, under more severe conditions, on the nitrogen of the amide, yielding compounds of formula XLVIII respectively. The protected aldehydes of formula XLIX may be used in this reaction to introduce the chain of atoms —$(CH_2)_y$—. However, it should be noted that the value for y is different from the definition in claim 1. This is because the carbon of the protected aldehyde will eventually form a part of the chain between the nitrogen atom and the Z-group. Thus, in the reagent of formula XLIX, as well as in the product compound of formula XLVII, y=1 to 4 instead of 2 to 5. Suitable conditions for these alkylation reactions include the use of sodium hydride as base, followed by the alkylating agent, or the use of an alkali metal carbonate, especially potassium or cesium carbonate. Both types of reagent may be used in DMF or DMA solution. NaH may also be used in solution in an ether, such as THF or 1,2-dimethoxyethane.

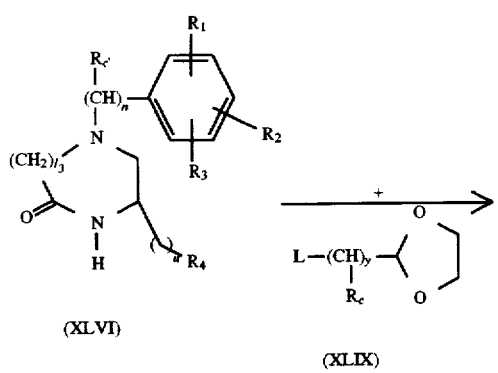

(XLVI)    (XLIX)

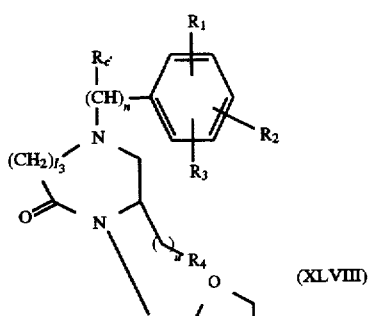

(XLVIII)

The acetal protecting group may next be removed by reaction with an acidic reagent, such as HCl/dioxane, to produce the aldehydes of formula LI.

(XLVIII) ⟶

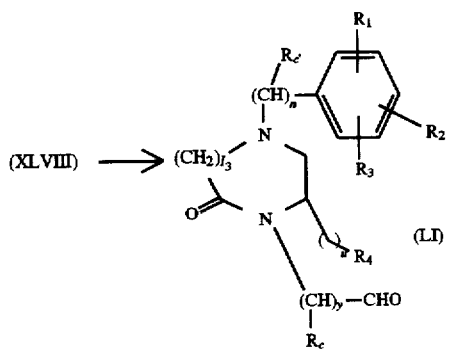

(LI)

The aldehydes of formula LI may now be modified by the introduction of the group Z—. This may be accomplished by a reductive alkylation of the amine Z—H with the aldehydes under standard conditions. Such conditions are exemplified by the use of sodium cyanoborohydride in an alcohol solvent, preferably methanol, at a reaction temperature between about 0° C. and RT. Products of these reactions are compounds of the invention of formula LIII where y is now the same as defined in claim 1, that is 2–5.

(LI) ⟶

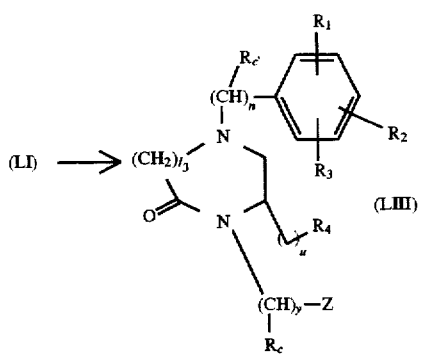

(LIII)

Controlled alkylation of compounds of formula XLVI using a differentially activated alkylene dihalide of formula LIV, in which Hal$_1$ is chloro and Hal$_2$ is either bromo or iodo, produces the haloalkyl derivatives of formula LVI. Suitable bases for this transformation include NaH in DMF, DMA, or THF.

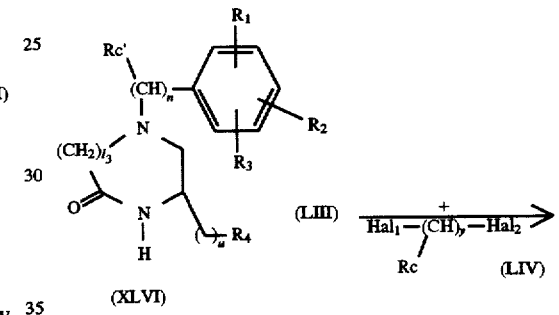

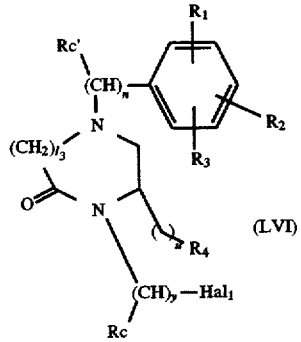

(LVI)

Reaction of these halogen compounds with the amine Z—H is carried out using an organic tertiary amine to absorb the H-Hal$_1$. Suitable bases include Hünig's Base. However, it is well known that if Hal$_1$ is a chlorine atom that it is not easily displaced, it is often preferable to replace the chlorine by, preferably, an iodine atom. This may be achieved by treating the compounds of formula LVI with a solution of NaI or KI in acetone or a higher ketone, such as methyl ethyl ketone or methyl iso-butyl ketone, and heating the solution to a temperature between RT and the boiling point of the solvent in use. Conditions may be adjusted to suit the particular substrate. Subsequent treatment of the exchanged halogen product with the amine Z—H, as described above, leads to the products of formula LVIII which are compounds of the invention.

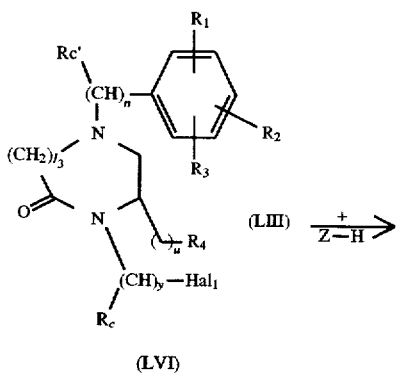

(LVI)

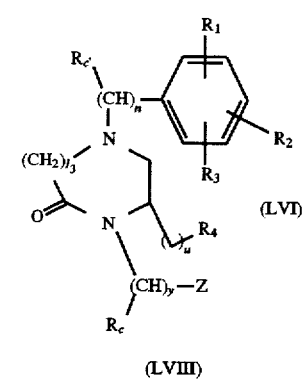

(LVIII)

The in vitro and in vivo activity of the compounds of formula I can be determined by the following procedures.

In vitro procedure to identify $NK_1$ activity

Test compounds are evaluated for their ability to inhibit the activity of the $NK_1$ agonist Substance P on the isolated guinea pig vas deferens. Freshly cut vas deferens are removed from male Hartley guinea pigs (230–350 g) and suspended in 25 ml tissue baths containing Kreb's Henseleit solution warmed to 37° C. and constantly aerated with 95% $O_2$ and 5% $CO_2$. Tissues are adjusted to 0.5 g and allowed to equilibrate for a period of 30 minutes. The vas deferens are exposed to an electrical field stimulation (Grass S48 Stimulator) every 60 seconds at an intensity that will cause the tissue to contract 80% of its maximum capacity. All responses are recorded isometrically by means of a Grass force displacement transducer (FT03) and Harvard electronic recorder. Substance P inhibits the electrical field stimulated-induced contractions of the guinea pig vas deferens. In unpaired studies, all tissues (control or drug treated) are exposed to cumulative concentrations of Substance P ($1\times10^{-10}$M–$7\times10^{-7}$M). Single log-concentrations of the test compounds are given to separate tissues and allowed to equilibrate for 30 minutes before a Substance P concentration-response curve is generated. At least separate tissues are used for each control and individual drug-concentration for every drug assay.

Inhibition of the Substance P is demonstrated by a rightward shift of its concentration-response curve. These shifts are used to determine the $pA_2$ value, which is defined as the negative log of the molar concentration of the inhibitor which would require that twice as much agonist be used to elicit a chosen response. This value is used to determine relative antagonist potency.

Isolated Hamster Trachea $NK_2$ Assay

General methodology and characterization of hamster trachea responses to neurokinin agonists as providing an $NK_2$ monoreceptor assay is found in C. A. Maggi, et al., *Eur.* *J. Pharmacol.* 166 (1989) 435 and J. L. Ellis, et al., *J. Pharm. Exp. Ther.* 267 (1993) 95.

Continuous isometric tension monitoring is achieved with Grass FT-03 force displacement transducers connected to Buxco Electronics preamplifiers built into a Graphtec Linearcorder Model WR 3310.

Male Charles River LAK:LVG (SYR) hamsters, 100–200 g fed weight, are stunned by a sharp blow to the head, loss of corneal reflex is assured, the hamsters are sacrificed by thoractomy and cutting the heart. Cervical trachea segments are removed to room temperature Krebs buffer, pH 7.4, aerated with 95% $O_2$–5% $CO_2$ gas and cleaned of adhering tissue. The segments are cut into two 3–4 mm long ring segments. Tracheal rings are suspended from transducers and anchored in 15.0 ml water jacketed organ baths by means of stainless steel hooks and 6-0 silk. Baths are filled with Krebs buffer, pH 7.4, maintained at 37° C. and continuously aerated with 95% $O_2$–5% $CO_2$ gas. Tracheal rings are placed under 1.0 g initial tension and allowed a 90 min equilibration period with four 1 µM NKA challenge, wash and recovery cycles at 20 min intervals. 30 min vehicle pretreatment is followed by cumulative additions of rising doses of NKA (3 nM–1 µM final concentration, 5 min intervals between additions). The final NKA response is followed by a 15 min wash and recovery period. 30 min pretreatment with a test compound or its vehicle is followed by cumulative additions of rising doses of NKA (3 nM–10 µM final concentration if necessary, 5 min intervals between additions). The final NKA response is followed by a 1 mM carbachol challenge to obtain a maximal tension response in each tissue.

Tissue responses to NKA are recorded as positive pen displacements over baseline and converted to grams tension by comparison to standard weights. Responses are normalized as a % of the maximal tissue tension. $ED_{50}$'s are calculated for NKA from the control and treated NKA dose responses and compared. Test compounds resulting in an agonist dose ratio $\geq 2$ at a screening concentration of 1 µM (i.e. $pA_2 \geq =6.0$) are considered actives. Further dose response data is obtained for actives so that an apparent $pA_2$ estimate can be calculated. $pA_2$ is calculated either by estimation of $K_i$ as described by Furchgott (where $pA_2=-$Log $K_i$, R. F. Furchgott, *Pharm. Rev.* 7 [1995] 183) or by Shild Plot Analysis (O. Arunlakshana & H. O. Shild, *Br. J. Pharmacol.* 14[1959] 48) if the data is sufficient.

Effect of $NK_1$ Antagonists on Substance P-Induced Airway Microvascular Leakage In Guinea Pigs Studies are performed on male Hartley guinea pigs ranging in weight from 400–650 g. The animals are given food and water ad libitum. The animals are anesthetized by intraperitoneal injection of dialurethane (containing 0.1 g/ml diallylbarbituric acid, 0.4 g/ml ethylurea and 0.4 g/ml urethane). The trachea is cannulated just below the larynx and the animals are ventilated ($V_T$=4 ml, f=45 breaths/min) with a Harvard rodent respirator. The jugular vein is cannulated for the injection of drugs.

The Evans blue dye technique (Danko, G. et al., *Pharmacol. Commun.*, 1, 203–209, 1992) is used to measure airway microvascular leakage (AML). Evans blue (30 mg/kg) is injected intravenously, followed 1 min later by i.v. injection of substance P (10 µg/kg). Five min later, the thorax is opended and a blunt-ended 13-guage needle passed into the aorta. An incision is made in the right atrium and blood is expelled by flushing 100 ml of saline through the aortic catheter. The lungs and trachea are removed en-bloc and the trachea and bronchi are then blotted dry with filter paper and weighed. Evans blue is extracted by incubation of the tissue at 37° C. for 18 hr in 2 ml of formamide in stoppered tubes. The absorbance of the formamide extracts of dye is measured at 620 nm. The amount of dye is calculated by interpolation from a standard curve of Evans blue in the range 0.5–10 μg/ml in formamide. The dye concentration is expressed as ng dye per mg tissue wet weight. Test compounds were suspended in cyclodextran vehicle and given i.v. 5 min before substance P.

Measurement of $NK_2$ Activity In Vivo

Male Hartley guinea pigs (400–500 gm) with ad lib. access to food and water are anesthetized with an intraperitoneal injection of 0.9 ml/kg dialurethane (containing 0.1 g/m diallylbarbituric acid, 0.4 g/ml ethylurea and 0.4 g/ml urethane). After induction of a surgical plane of anesthesia, tracheal, esophageal and jugular venous cannulae are implanted to facilitate mechanical respiration, measurement of esophageal pressure and administration of drugs, respectively.

The guinea pigs are placed inside a whole body plethysmograph and the catheters connected to outlet ports in the plethysmograph wall. Airflow is measured using a differential pressure transducer (Validyne, Northridge Calif., model MP45-1, range±2 $cmH_2O$) which measures the pressure across a wire mesh screen that covers a 1 inch hole in the wall of the plethysmograph. The airflow signal is electrically integrated to a signal proportional to volume. Transpulmonary pressure is measured as the pressure difference between the trachea and the esophagus using a differential pressure transducer (Validyne, Northridge, Calif., model MP45-1, range±20 cm $H_2O$). The volume, airflow and transpulmonary pressure signals are monitored by means of a pulmonary analysis computer (Buxco Electronics, Sharon, Conn., model 6) and used for the derivation of pulmonary resistance ($R_L$) and dynamic lung compliance ($C_{Dyn}$).

Bronchoconstriction Due to NKA

Increasing iv doses of NKA are administered at half log (0.01–3 μg/kg) intervals allowing recovery to baseline pulmonary mechanics between each dose. Peak bronchoconstriction occurs within 30 seconds after each dose of agonist. The dose response is stopped when $C_{Dyn}$ is reduced 80–90% from baseline. One dose-response to NKA is performed in each animal. Test compounds are suspended in cyclodextran vehicle and given i.v. 5 min before the initiation of the NKA dose response.

For each animal, dose response curves to NKA are constructed by plotting the percent increase in $R_L$ or decrease in $C_{Dyn}$ against log dose of agonist. The doses of NKA that increased $R_L$ by 100% ($R_L100$) or decreased $C_{Dyn}$ by 40% ($C_{Dyn}40$) from baseline values are obtained by log-linear interpolation of the dose response curves.

Neurokinin Receptor Binding Assay(s)

Chinese Hamster ovary (CHO) cells transfected with the coding regions for the human neurokinin 1 ($NK_1$) of the human neurokinin 2 ($NK_2$) receptors are grown in Dulbecco's minimal essential medium supplemented with 10% fetal calf serum, 0.1 mM non-essential amino acids, 2 mM glutamine, 100 units/ml of penicillin and streptomycin, and 0.8 mg of G418/ml at 37° C. in a humidified atmosphere containing 5% $CO_2$.

Cells are detached from T-175 flasks with a sterile solution containing 5 mM EDTA in phosphate buffered saline. Cells are harvested by centrifugation and washed in RPMI media at 40° C. for 5 minutes. The pellet is resuspended in Tris-HCl (pH7.4) containing 1 uM phsphoramidon and 4 ug/ml of chymostatin at a cell density of $30\times10^6$ cells/ml. The suspension is then homogenized in a Brinkman Polytron (setting 5) for 30–45 seconds. The homogenate is centrifuged at 800×g for 5 min at 40° C. to collect unbroken cells and nuclei. The supernatant is centrifuged in a Sorvall RC5C at 19,000 rpm (44,00×g) for 30 min at 4° C. The pellet is resuspended, an aliquot is removed for a protein determination (BCA) and washed again. The resulting pellet is stored at –80° C.

To assay receptor binding, 50 μl of [$^3$H]-Substance P (9-Sar, 11-Met [02]) (specific activity 41 Ci/mmol) (Dupont-NEN) (0.8 nM for the NK-1 assay) or [$^3$H]-Neurokinin A (specific activity 114 Ci/mmole) (Zenca) (1.0 nM for the NK-2 assay) is added to tubes containing buffer (50 mM Tris-HCl (pH 7.4) with 1 mM $MnCl_2$ and 0.2% Bovine Serum Albumin) and either DMSO or test compound. Binding is initiated by the addition of 100 μl of membrane (10–20 μg) containing the human NK-1 or NK-2 receptor in a final volume of 200 μl. After 40 minutes at room temperature, the reaction is stopped by rapid filtration onto Whatman GF/C filters which have been presoaked in 0.3% polyethylenimine. Filters are washed 2 times with 3 ml of 50 mM Tris-HCl (pH7.4). Filters are added to 6 mls of Ready-Safe liquid scintillation cocktail and quantified by liquid scintillation spectrometry in a LKB 1219 RackBeta counter. Non-specific binding is determined by the addition of either 1 μM of CP-99994 ($NK_1$) or 1 μM SR-48968 ($NK_2$) (both synthesized by the chemistry department of Schering-Plough Research Institute). $IC_{50}$ values are determined from competition binding curves and Ki values are determined according to Cheng and Prusoff using the experimentally determined value of 0.8 nM for the $NK_1$ receptor and 2.4 nM for the $NK_2$ receptor.

Using the test procedures described above, the following data were obtained for representative compounds of formula I:

For all of the compounds of the invention, the $NK_1$ binding is in a range of about 10–93% inhibition at 1 μM concentration. For all of the compounds of the invention, the $NK_2$ binding is in a range of about 0–70% inhibition at 1 μM concentration. It should be understood that while the $NK_2$ binding for certain compounds of the invention is as low as 0% at 1 μM concentration, that at higher concentrations these compounds may have $NK_2$ binding inhibition activity.

Representative values for compounds of the invention are as follows:

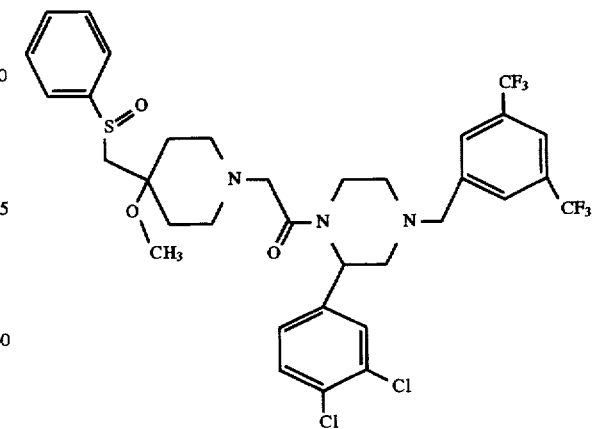

has a $K_i$ for $NK_1$ binding, of 136 nM; and for $NK_2$ binding, a 24% inhibition at 1 μM.

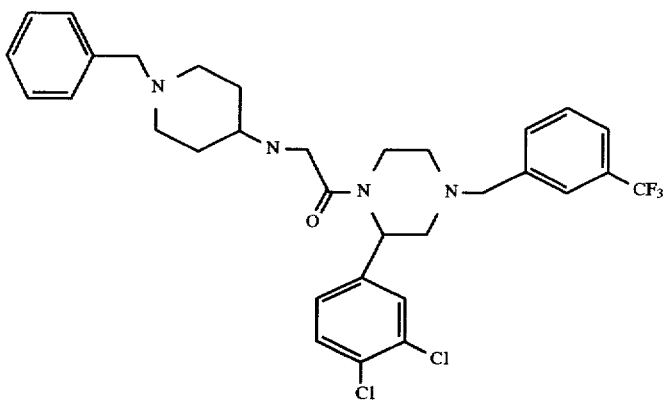

has a $K_i$ for $NK_1$ binding, of 30 nM; and a $K_i$ for $NK_2$ binding, of 175 nM.

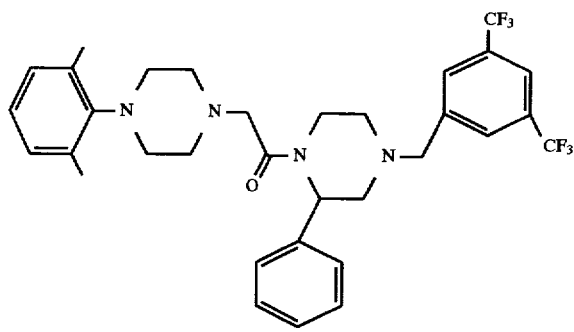

has for $NK_1$ binding, a 48% inhibition at 1 μM; and for $NK_2$ binding, a 0% inhibition at 1 μM.

The $K_i$ of a compound is that concentration at which the compound caused 50% inhibition of either $NK_1$ or $NK_2$. For those compounds of the invention having higher than 50% inhibition of $NK_1$, $K_i$'s for $NK_1$ were determined. The $K_i$'s for $NK_1$ for such compounds fell within a range of about 11 nM to about 176 nM.

For those compounds of the invention having higher than 50% inhibition of $NK_2$, $K_i$'s for $NK_2$ were determined. The $K_i$'s for $NK_2$ for such compounds fell within a range of about 175 nM to about 300 nM.

It will be recognized that compounds of formula I exhibit $NK_1$ and $NK_2$ antagonist activity to varying degrees, i.e., certain compounds have strong $NK_1$ antagonist activity, but weaker $NK_2$ antagonist activity. Others are strong $NK_2$ antagonists, but weaker $NK_1$ antagonists. While compounds with approximate equipotency are preferred, it is also within the scope of this invention to use compounds of with unequal $NK_1/NK_2$ antagonist activity when clinically appropriate.

Certain compounds of formula I have been found to be antagonists of both $NK_1$ and $NK_2$ receptors, and are therefore useful in treating conditions caused or aggravated by the activity of $NK_1$ and $NK_2$ receptors.

The present invention also relates to a pharmaceutical composition comprising a compound of formula I and a pharmaceutically acceptable carrier. Compounds of this invention can be administered in conventional oral dosage forms such as capsules, tablets, powders, cachets, suspensions or solutions, or in injectable dosage forms such as solutions, suspensions, or powders for reconstitution. The pharmaceutical compositions can be prepared with conventional excipients and additives, using well known formulation techniques. Pharmaceutically acceptable excipients and additives include nontoxic and chemically compatible fillers, binders, disintegrants, buffers, preservatives, antioxidants, lubricants, flavorings, thickeners, coloring agents, emulsifiers and the like.

The daily dose of a compound of formula I for treating asthma, cough, bronchospasm, inflammatory disease, migraine, nociception and gastrointestinal disorders is about 0.1 mg to about 20 mg/kg of body weight per day, preferably about 0.5 to about 15 mg/kg, more preferably 0.5 to about 5 mg/kg. For an average body weight of 70 kg, the dosage range is therefore from about 1 to about 1500 mg of drug per day, preferably about 50 to about 100 mg, given in a single dose or 2-4 divided doses. The exact dose, however is determined by the attending clinician, and is dependent on the potency of the compound administered, the age, weight, condition and response of the patient.

The invention disclosed herein is examplified by the following examples, which should not be construed to limit the scope of the disclosure. Alternative mechanistic pathways and analogous structures within the scope of the invention will be apparent to those skilled in the art.

EXAMPLE 1

Preparation of (+, −)-1-[[3,5-bis(trifluoromethyl) phenyl]methyl]-3-phenylpiperazine, dihydrochloride salt, quarter hydrate

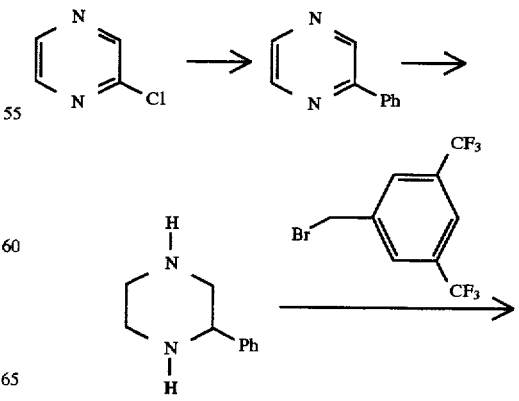

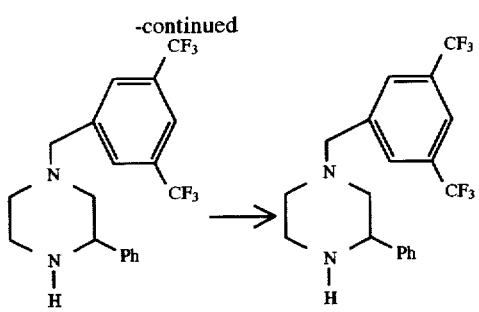

Chloropyrazine (20.68 gram, 177 mmol) and [1,2-bis (diphenylphosphino)ethane]nickel(II) chloride (41.08 gram, 77.8 mmol) in dry THF (1.5 liter) were mixed and stirred for 80 minutes in a flask (cooled with a water bath) under nitrogen. A solution of phenylmagnesium bromide (3M in $Et_2O$) (103 ml, 309 mmol) was added slowly through a dropping funnel into the cooled brick-red slurry at room temperature under nitrogen over 3.5 hours. After stirring at room temperature overnight, TLC showed that the reaction was complete. 3N HCl (100 ml) was added slowly through a dropping funnel under nitrogen and the mixture was stirred for one hour. The THF layer was separated from the aqueous layer. The aqueous layer was adjusted to pH 12 with 6N NaOH and extracted with EtOAc (100 ml, 3×). The organic fractions (THF and EtOAc) were combined and dried over $MgSO_4$, filtered and concentrated to give a solid. The product was purified by flash chromatography on 300 g of flash grade silica gel in 2.5% $EtOAc/CH_2Cl_2$ to give 10.79 gram (69 mmol, 39%) of 2-phenylpyrazine, m.p. 69°–70° C.; FAB mass [M+1]$^+$ 157; Found, C, 76.55; H, 5.22; N, 17.71. Calcd. for $C_{10}H_8N_2$, C, 76.90; H, 5.16;. N, 19.93.

To a solution of 2-phenylpyrazine (11.64 gram, 74.53 mmol) in acetic acid (58.2 ml) was added palladium acetate $Pd(OAc)_2$ (2.33 gram, 9.94 mmol). The mixture was hydrogenated at 50 psi for four hours. After the reaction was complete, the catalyst was filtered off and rinsed with a small portion of acetic acid. The filtrate was concentrated under house vacuum to give a brown-black solid which was suspended in deionized water (300 ml) and adjusted to pH 13 with 20% NaOH solution. The product was extracted from aqueous solution with EtOAc (200 ml, 3×), dried over $MgSO_4$, filtered and evaporated to dryness to give 2-phenylpiperazine (7.2 gram). An additional 1.6 g of 2-phenylpiperazine was obtained by evaporating the aqueous fraction to a solid and triturating the solid with $CH_2Cl_2$. Total yield of 2-phenylpiperazine was 73%. The crude material was crystallized from EtOAc and hexane for characterization, m.p. 86°–88° C.; FAB mass [M+1]$^+$ 163; Found, C, 74.04; H, 8.66; N, 17.15. Calcd. for $C_{10}H_{14}N_2$, C, 74.04; H, 8.69; N, 17.26.

To a solution of 2-phenylpiperazine (4.0 gram, 24.65 mmol) in dry $CH_2Cl_2$ (200 ml) at −78 ° C. under nitrogen was added $Et_3N$ (5.15 ml, 36.97 mmol) followed by the dropwise addition of a $CH_2Cl_2$ solution(46.60 ml) of bis (trifluoromethyl)benzyl bromide (4.66 ml, 24.65 mmol). The flask was kept at −78° C. then it was gradually warmed to room temperature overnight. After TLC showed that the reaction was complete, the material was washed with brine (150 ml, 2×), dried over $MgSO_4$, filtered, and evaporated under vacuum to yield a tan solid. The crude product was purified by flash silica gel chromatography (150 g), eluting with 2.5% $MeOH/CH_2Cl_2$ to give (+,−) 1-[[3,5-bis (trifluoromethyl)phenyl]methyl]-3-phenyl-piperazine (6.96 gram, 17.92 mmol, 72.7%) as an oil. A portion of this oil (0.5 gram, 1.287 mmol)) was converted to its hydrochloride salt by dissolving the oil in $CH_2Cl_2$ (20 ml) and treating with 2.3M HCl-EtOH (1.3 ml, 2.99 mmol). After stirring at room temperature for 10 minutes, all solvents were removed under high vacuum and the residue was dried overnight, m.p. 229°–233° C.; FAB mass [M+1]$^+$ 389; Found, C, 48.83; H, 4.28; N, 5.87; Cl, 14.77; F, 24.03. Calcd. for $C_{19}H_{18}N_2F_6$·2HCl·0.25 $H_2O$. C, 48.99; H, 4.43; N, 6.01; Cl, 15.22; F, 24.47.

EXAMPLE 2

Preparation of (+,−)-4-[[3,5-bis(trifluoromethyl) phenyl]methyl]-2-phenyl-1-[[[1-(phenylmethyl)-4-piperidinyl]amino]acetyl]piperazine, trihydrochloride salt, dihydrate

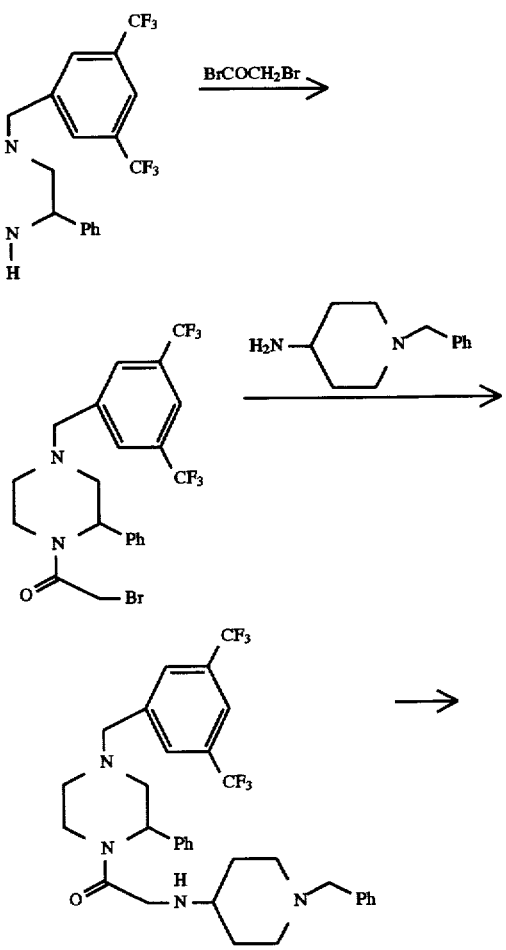

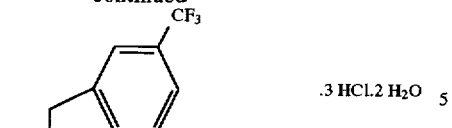

.3 HCl.2 H₂O

To a solution of (+, −) 1-|[3,5-bis(trifluoromethyl)phenyl]methyl|-3-phenyl-piperazine (0.76 gram, 1.975 mmol) in dry CH₂Cl₂ (15.2 ml) at −78° C. was added Et₃N (0.286 ml, 2.055 mmol) followed by the dropwise addition of bromoacetyl bromide (0.179 ml, 2.055 mmol). After stirring at −78° C. for 4 hours, the reaction was diluted with CH₂Cl₂ (200 ml), washed with brine (100 ml, 2×) and dried over MgSO₄. After filtration, the solvent was removed to give a light yellow solid which was used without further purification. FAB mass [M+1]⁺ 509.2 (⁷⁹Br).

The product from the previous reaction (1.067 gram, 2.096 mmol) was dissolved in dry CH₂Cl₂ (10.67 ml) and cooled to −78° C. under nitrogen. To this cooled solution were added 4-amino-1-benzylpiperidine (0.44 ml, 2.11 mmol) and diisopropylethylamine (0.402 ml, 2.3 mmol). The reaction was gradually warmed to room temperature overnight under nitrogen. After completion, CH₂Cl₂ (300 ml) was added and the organic layer was washed with brine (100 ml, 2×), dried over MgSO₄ and filtered. The filtrate was evaporated under vacuum to give a crude oil which was purified by flash chromatography on flash grade silica gel (100 g), eluting with 2.5% NH₃-MeOH-2.5% EtOH/CH₂Cl₂ to give a light yellow oil (0.76 g, 1.229 mmol, 59%). A portion of the oil (0.27 gram, 0.436 mmol) was converted to its hydrochloride salt by dissolving in CH₂Cl₂ (13.5 ml) and treating with 2.3M HCl-EtOH (0.938 ml, 2.182 mmol). After stirring at room temperature for 40 minutes, solvent was evaporated and the residue was vacuum dried overnight, m.p. 199°–202° C.; FAB mass [M+1]⁺ 619.5; Found, C, 51.73; H, 5.98; N, 7.18; Cl, 13.69; F, 14.75. Calcd. for C₃₃H₃₆N₄OF₆.3 HCl.2 H₂O, C, 51.87 H, 5.67; N, 7.33; Cl, 13.92; F. 14.91.

EXAMPLE 3
Preparation of (+, −)-4-|[3,5-bis(trifluoromethyl)phenyl]methyl]-1-|2-(4-hydroxy-4-phenyl-1-piperidinyl)acetyl|-2-phenylpiperazine, dihydrochloride salt, 1.5 hydrate

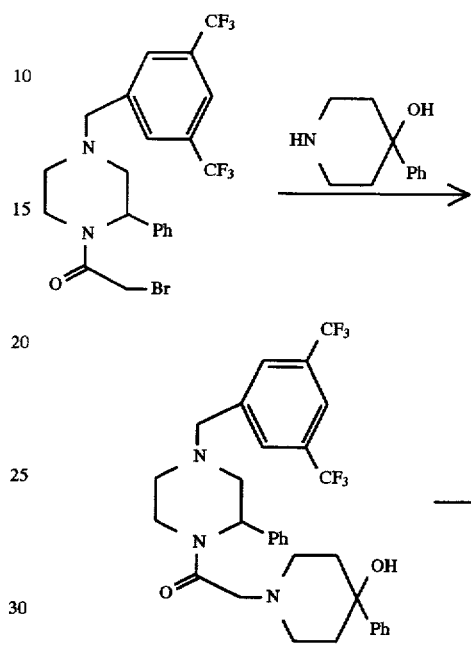

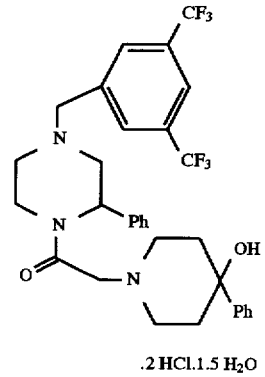

.2 HCl.1.5 H₂O

By process analogous to that described in Example 2, employing 4-hydroxy-4-phenyl-piperidine in place of 4-amino-1-benzyl-piperidine the title compound was prepared. m.p. 185°–187° C.; FAB mass [M+1]⁺ 606.6 Found, C, 54.58; H. 5.44; N. 5.75; Cl, 9.71; F. 16.11. Calcd. for C₃₂H₃₃O₂N₃F₆.2 HCl.1.5 H₂O. C, 54.47; H, 5.43; N. 5.96; Cl. 10.05; F. 16.16.

By process analogous to that described in Example 2, employing appropriate heterocyclic derivatives (Z group), as listed below, in place of 4-amino-1-benzyl-piperidine, the following compounds were prepared.

| Z | salt | m.p. °C. | [M + 1] FAB mass | High Res. Mass |
|---|---|---|---|---|
| H₃CC—N(H)—C(Ph)(piperidinyl)N— (acetamido-phenyl-piperidinyl) | free form | 198–201 | 647.4 | |
| Ph-CH₂-N(piperazinyl)N— | 3HCl.2H₂O | 192–195 | 605.5 | |
| Ph-CH₂-(piperidinyl)N— | 2HCl.1.5H₂O | 162–165 | 604.5 | |
| Ph-CH₂-N(diazabicyclic)N— | free form | 45–47 | 617.3 | Cal'd 617.2715<br>Found 617.2731 |
| 2,6-dimethylphenyl-piperazinyl N— | free form | 66–68 | 619.3 | Cal'd 619.2872<br>Found 619.2856 |
| PhS-C(=S)-CH₂-C(OMe)(piperidinyl)N— | free form | 68–71 | 682.3 | |

EXAMPLE 4

Preparation of (+.−)-4-[[3,5-bis(trifluoromethyl) phenyl]methyl]-2-phenyl-N-[1-(phenylmethyl)-4-piperidinyl]-1-piperazineethanamine, tetrahydrochloride salt, monohydrate

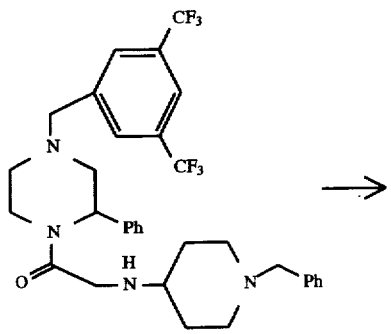

-continued

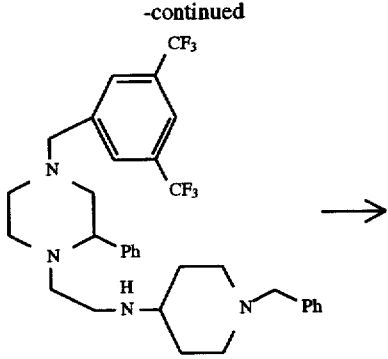

53

-continued

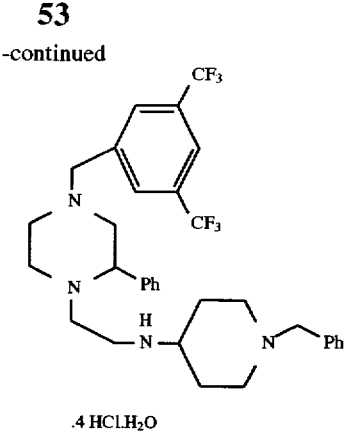

.4 HCl.H₂O

To a solution of (+, −)-4-[[3,5-bis(trifluoromethyl)phenyl]methyl]-2-phenyl-1-[[[1-(phenylmethyl)-4-piperidinyl]amino]acetyl]piperazine (0.48 g, 0.776 mmol) in THF (12 ml) was added 10M BH₃.S(CH₃)₂ (0.388 ml, 3.88 mmol). The mixture was heated in an oil bath at 80° C. under nitrogen overnight. After completion, excess BH₃ was decomposed by dropwise addition of MeOH to the cooled solution under nitrogen. MeOH was evaporated and the residue was redissolved in EtOH (14.4 ml). K₂CO₃ (0.235 gram, 1.707 mmol) was added and the mixture was refluxed at 80° C. for five hours. After TLC showed that the reaction was complete, the solid was filtered off and the filtrate was evaporated under vacuum. The residue was redissolved in EtOAc (300 ml), washed with brine (100 ml) and dried over MgSO₄. It was filtered and evaporated under vacuum to give an oil which was purified by flash chromatography on flash grade silica gel (80 g), eluting with 3% NH₃-MeOH/CH₂Cl₂ to give the desired material as an oil (0.373 gram, 0.615 mmol, 79%). A portion of the oil (0.36 gram) was converted to its hydrochloride salt by dissolving in dry CH₂Cl₂ (18 ml), followed by the addition of 2.3M HCl-EtOH (1.3 ml). Solvents were removed after stirring at room temperature for 0.5 hour and the residue was vacuum dried, m.p. 238°–241° C.; FAB mass [M+1]⁺ 605.6; Found, C, 51.96; H, 5.83; N, 7.01; Cl, 14.52; F, 18.21. Calcd. for C₃₃H₃₈N₄F₆.4 HCl.H₂O, C, 51.57; H, 5.77; N, 7.29, Cl, 14.83; F, 18.45.

EXAMPLE 5

Preparation of (+, −)-1-[2-[4-[[3,5-bis(trifluoromethyl)phenyl]methyl]-2-phenyl-1-piperazinyl]ethyl]-4-phenyl-4-piperidinol, trihydrochloride salt, monhydrate

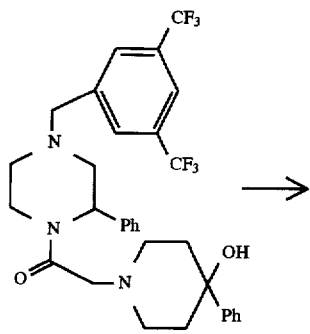

54

-continued

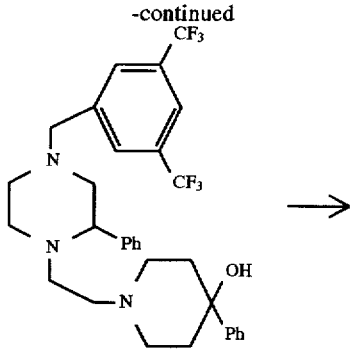

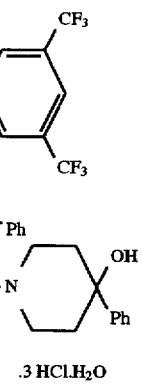

.3 HCl.H₂O

By a process analogous to the process described in Examples 3 and 4 the title compound was prepared, m.p. 215°–220° C.; FAB mass [M+1]⁺ 592.1; Found, C, 53.17; H, 5.51; N, 5.77; Cl, 14.37; F, 15.62. Calcd. for C₃₂H₃₅ON₃F₆.3 HCl.H₂O, C, 53.45; H, 5.61; N, 5.84; Cl, 14.79; F, 15.85.

By a process analogous to the process described in Examples 3 and 4, employing appropriate heterocyclic derivatives (Z group), listed below, in place of 4-amino-1-benzyl-piperidine, the following compounds were prepared.

| Z | salt | m.p. °C. | [M + 1]⁺ FAB mass |
|---|---|---|---|
| Ph—CH₂—N(\_\_\_)N— | 4HCl.1.0H₂O | >230 | 591.1 |
| Ph—CH₂—(\_\_\_)N— | 3HCl.1.0H₂O | >260 | 590.9 |

EXAMPLE 6

Preparation of (+, −)-N-|1-|2-|4-||3,4-bis(trifluoromethyl)phenyl|methyl|-2-phenyl-1-piperazinyl|ethyl|-4-phenyl-4-piperidinyl| acetamide, trihydrochloride salt, 1.5 hydrate

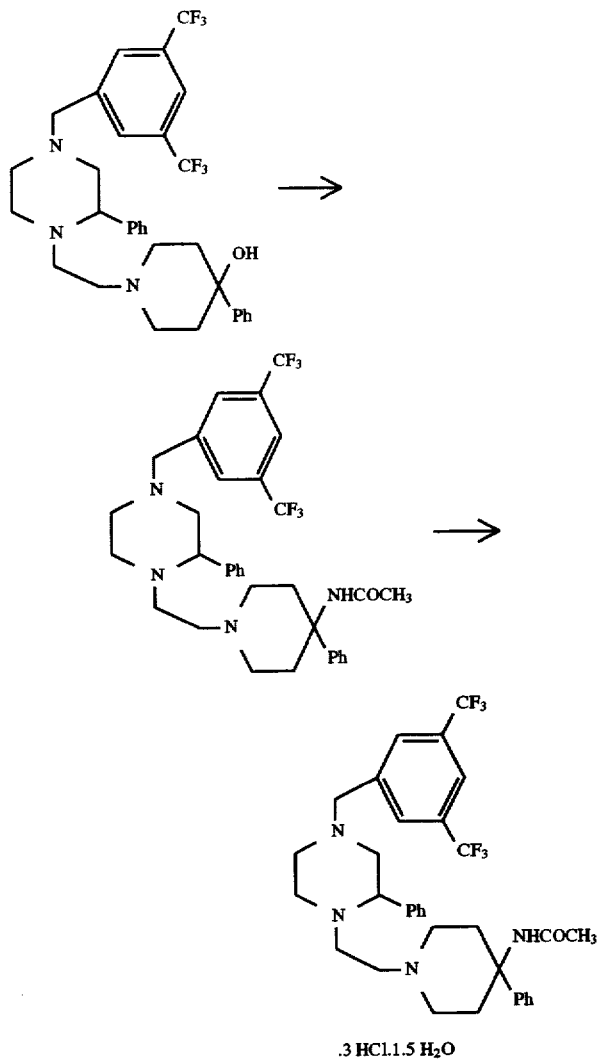

To a solution of the product from Example 5 (free form) (0.66 gram, 1.116 mmol) in 5.0 ml of acetonitrile was added dropwise concentrated sulfuric acid (2.44 ml) at room temperature under nitrogen. After 4 hours, water (100 ml) was added to the reaction and the solution was adjusted to pH 9 with 10% NaOH solution. The product was extracted from the aqueous solution with EtOAc (100 ml, 3×). The organic fractions were combined and washed with brine (100 ml), dried over $MgSO_4$, filtered, and concentrated under vacuum to give an oil. The product was purified by flash chromatography on flash silica gel (80 g) and was eluted with 10% $NH_3$-MeOH/$CH_2Cl_2$ to give an oil (0.40 g, 0.774 mmol, 69%). A portion of this oil (0.4 g, 0.632 mmol) was dissolved in $CH_2Cl_2$ (20 ml) and treated with 2.3M HCl-EtOH (2.528 mmol). After stirring at RT for 0.5 hour, solvents were removed under vacuum to give a white solid, m.p. 245°–247° C.; FAB mass [M+1]+ 633.4; Found, C, 53.27; H, 5.80; N, 7.23; Cl, 13.91; F, 14.55. Calcd. for $C_{34}H_{38}ON_4F_6$·3 HCl·1.5 $H_2O$, C, 53.09; H, 5.76; N, 7.28; Cl, 13.83; F, 14.82.

EXAMPLE 7

Preparation of (+, −)-1-|(2-methoxyphenyl)methyl|-3-phenyl-piperazine, dihydrochloride salt, monohydrate

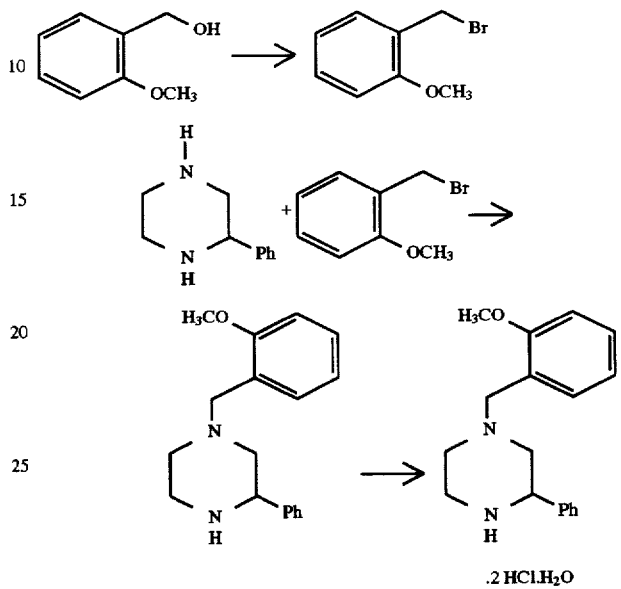

To a solution of 1-hydroxymethyl-2-methoxy-benzene (28.7 gram, 0.207 mol) in $CH_2Cl_2$ (574 ml) at 0° C. under nitrogen was added slowly $PBr_3$ (13.66 ml, 0.145 mol). After stirring for an additional 1.5 hours, MeOH (13.66 ml) was added and stirred for 5 minutes. To this mixture was added dropwise 10% $Na_2CO_3$ (2 ml) solution and stirred for 5 minutes. The mixture was then washed with 10% $Na_2CO_3$ (50 ml, 2×) and brine (100 ml). It was dried over $MgSO_4$, and filtered. The filtrate was removed under vacuum to give an oil (40 gram) of 1-bromomethyl-2-methoxy-benzene. This material was used without purification.

To a solution of (+, −)-2-phenyl-piperazine (2.83 gram, 17.44 mmol) (described in Example 1) in dry $CH_2Cl_2$ (141.5 ml) at −78° C. was added slowly a solution of 1-bromomethyl-2-methoxy-benzene (3.507 gram, 17.44 mmol) in dry $CH_2Cl_2$ (35 ml) under nitrogen. The reaction was stirred at −78° C. and gradually warmed to RT overnight. After completion, the product was diluted with $CH_2Cl_2$ (200 ml), washed with brine (100 ml), dried over $MgSO_4$ and filtered. The filtrate was removed under vacuum to give an oil. The product was purified by flash chromatography on flash grade silica gel (150 g), eluting with 4% MeOH/$CH_2Cl_2$ to give the title compound as an oil (2.68 gram, 54%). A portion of this oil (0.33 gram, 1.168 mmol) was dissolved in $CH_2Cl_2$ (10.0 ml) and treated with 2.3M HCl (1.1 ml, 2.53 mol). After stirring at room temperature for 10 minutes, solvents were removed under vacuum to give a solid, m.p. 152°–156° C.; FAB mass [M+1]+ 283.2. Found, C, 58.18; H, 7.23; N, 7.33; Cl, 18.89. Calcd. for $C_{18}H_{22}ON_2$·2 HCl·$H_2O$, C, 57.91; H, 7.02; N, 7.50; Cl, 18.99.

EXAMPLE 8

Preparation of (+, −)-1-[(4-hydroxy-4-phenyl-1-piperidinyl)acetyl]-4-[(2-methoxy-phenyl)methyl]-2-phenyl piperazine, dihydrochloride salt

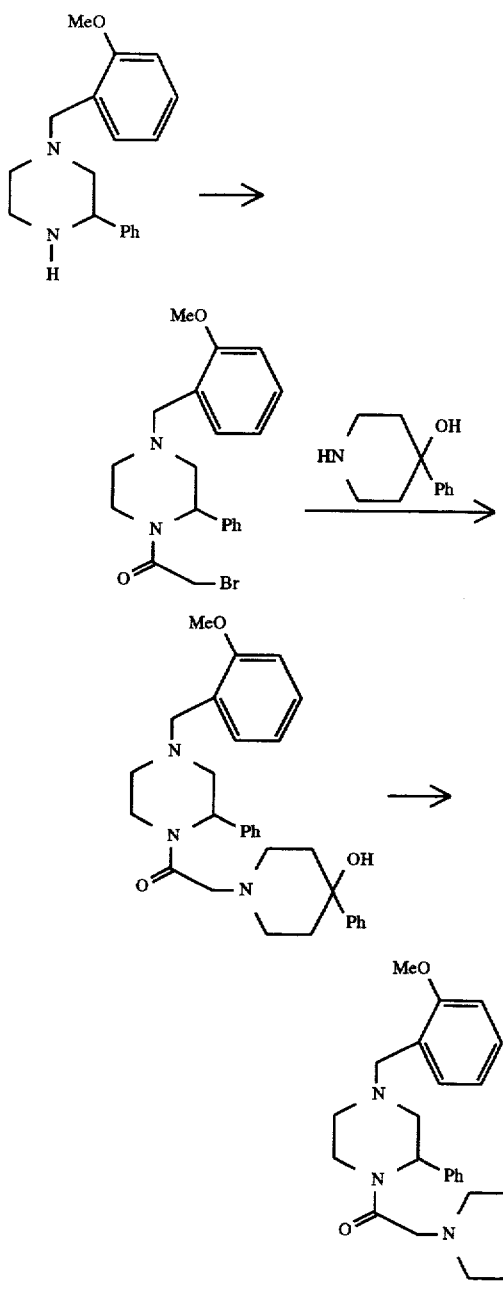

The bromoacetyl derivative of the product from Example 7 was prepared according to the procedure described in Example 2. This intermediate was used for the next reaction without further purification. The title compound was prepared by employing a process analogous to that described in Example 3, via the bromoacetyl derivative of (+, −)-1-[(2-methoxyphenyl)methyl]-3-phenyl-piperazine to give a solid, m.p. 183°–186° C.; FAB mass [M+1]+ 500; Found, C, 61.30; H, 7.54; N, 6.98; Cl, 11.65. Calcd. for $C_{31}H_{37}N_3O_3 \cdot 2$ HCl. C, 61.18; H, 7.12; N, 6.90; Cl, 11.65.

EXAMPLE 9

Preparation of (+, −)-1-[2-[4-[(2-methoxyphenyl)methyl]-2-phenyl-1-piperazinyl]ethyl]-4-phenyl-4-piperidinol

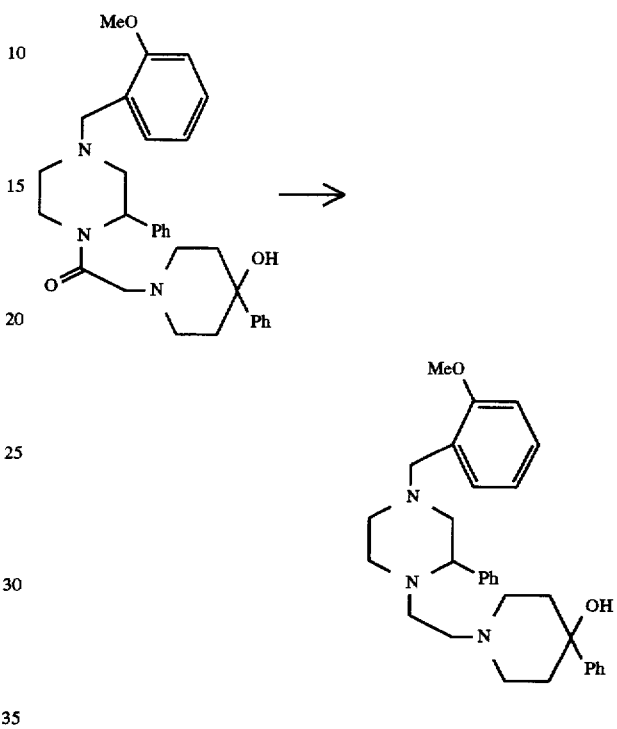

The product from Example 8 (free form) (0.7 gram, 1.4 mmol) was used to prepare the title compound by employing a procedure analogous to the procedure for Example 4. The title compound was a solid, m.p. 63°–65° C.; FAB mass [M+1]+ 486; Found, C, 75.86; H. 8.52; N. 8.54. Calcd. for $C_{31}H_{39}N_3O_2$. C, 75.54; H. 8.14; N. 8.53.

EXAMPLE 10

Preparation of 4-[[3,5-bis(trifluoromethyl)phenyl]methyl]-α-methyl-2-phenyl-1-piperazineacetamide, dihydrochloride salt, monohydrate (diastereomeric mixture)

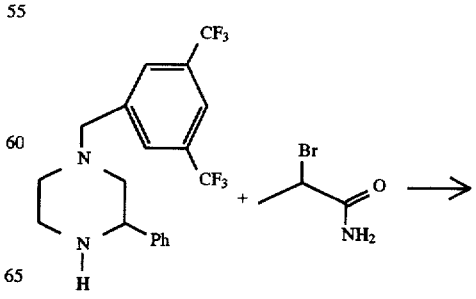

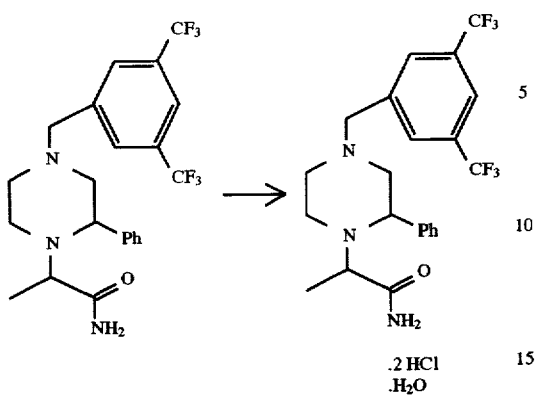

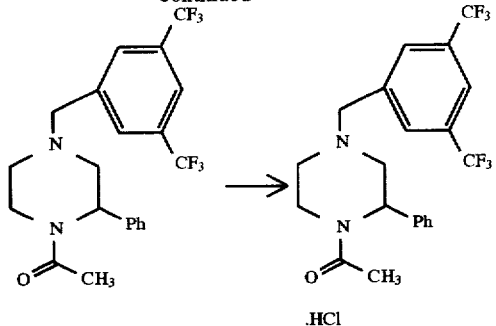

A mixture containing (+, −)-1-[[3,5-bis(trifluoromethyl)-phenyl]methyl]-3-phenyl piperazine (Example 1, free form) (0.5 gram, 1.3 mmol), 2-bromopropionamide (0.213 gram, 1.4 mmol), $K_2CO_3$ (0.193 gram, 1.4 mmol), n-$Bu_4NHSO_4$ (0.44 gram, 1.3 mmol), and dry DMF (20 ml) was heated at 80° C. overnight under nitrogen. After the reaction was complete, DMF was removed under vacuum and the residue was redissolved in EtOAc, washed with brine, dried over $MgSO_4$, and filtered. The filtrate was concentrated under vacuum to give a brown oil (0.55 g). The product was purified by flash chromatography on flash grade silica gel (70 g), and eluted with 3% MeOH/$CH_2Cl_2$ to give an oil (0.32 g, 53%). A portion of this oil (0.14 g, 0.305 mmol) was dissolved in $CH_2Cl_2$ (5 ml) and treated with 2.35M HCl/MeOH (0.324 ml, 0.762 mmol). After stirring at RT for 10 minutes, solvents were evaporated under vacuum to give a solid, m.p. >175° C., no sharp melting point; FAB mass [M+1]$^+$ 460.8; Found, C, 48.09; H, 4.73; N, 7.50; Cl, 12.43; F, 20.93. Calcd. for $C_{22}H_{23}N_3OF_6 \cdot 2$ HCl·$H_2O$ C, 48.01; H, 4.94; N, 7.63; Cl, 12.88; F, 20.71.

To a solution of (+, −)-1-[[3,5-bis(trifluoromethyl)phenyl]-methyl]-3-phenyl-piperazine (0.4 gram, 1.03 mmol) in dry $CH_2Cl_2$ (5 ml) was added diisopropyl ethyl amine (0.15 g, 1.1 mmol) and acetyl chloride (0.081 g, 1.03 mmol). The solution was stirred at 0° C. and warmed to RT overnight under nitrogen. After the reaction was complete, the product was diluted with EtOAc (100 ml) and washed with brine (20 ml, 3×). It was dried over $MgSO_4$, filtered and concentrated to give an oil (0.35 g, 0.81 mmol, 79%). The oil was converted to its hydrochloride salt as described in Example 10 to give a white solid, m.p. 202°–203° C.; FAB mass [M+1]$^+$ 431; Found, C, 53.76; H, 4.51; N, 6.00; Cl, 7.48; F, 24.54. Calcd. for $C_{21}H_{20}N_2OF_6 \cdot HCl$. C, 54.02; H, 4.53; N, 6.00; Cl, 7.60; F, 24.42

EXAMPLE 12

Preparation of (+, −)-1-[[3,5-bis(trifluoromethyl)phenyl]methyl]-3-(3,4-dichlorophenyl)-piperazine, dihydrochloride salt

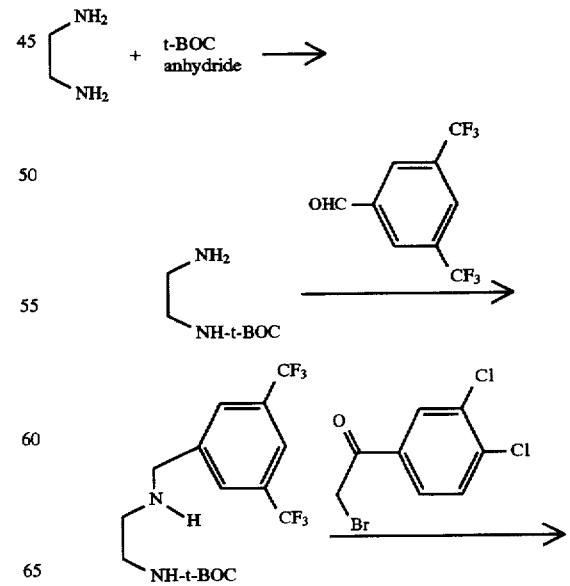

EXAMPLE 11

Preparation of (+, −)-1-acetyl-4-[[3,5-bis(trifluoromethyl)phenyl]methyl]-2-phenylpiperazine, hydrochloride

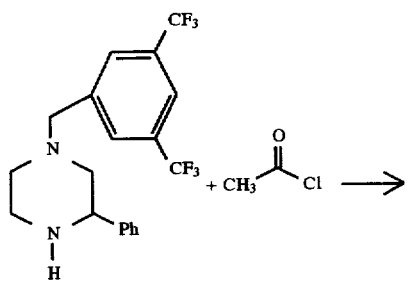

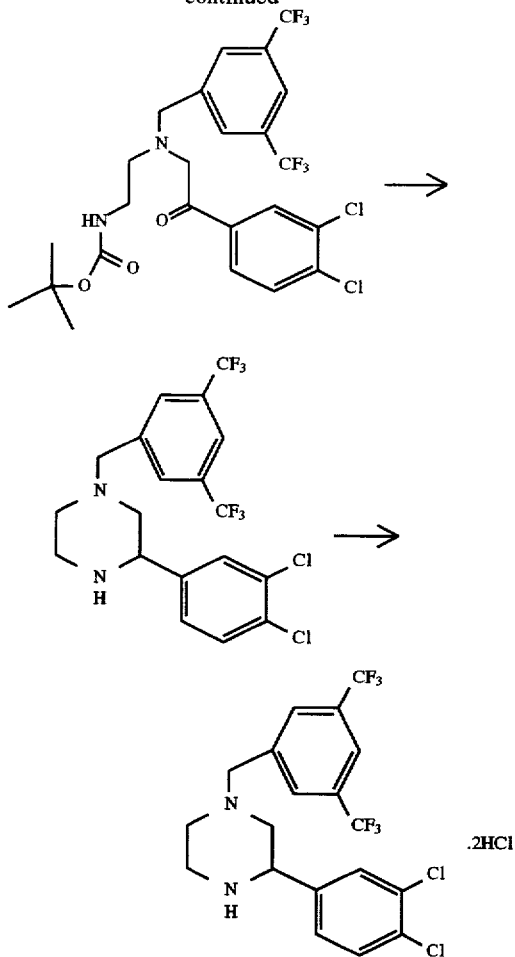

To a solution of ethylene diamine (30.0 gram, 0.5 mol) in MeOH (300 ml) at −10° C. under nitrogen was added dropwise a solution of di-t-butyidicarbonate (22 g, 0.1 mol) in MeOH (250 ml). The reaction was stirred at −10° C. for 5 hours then gradually warmed to RT overnight. After the reaction was complete, the mixture was concentrated under vacuum to give a residue which was suspended in $CH_2Cl_2$ (500 ml) and washed with brine (200 ml, 2×). The organic fraction was dried over $MgSO_4$, filtered and concentrated under vacuum to give an oil (10.8 g) which contained 10% of di-t-BOC protected material.

To a solution of the product (9.0 gram, 56 mmol) from the previous reaction in $CH_2Cl_2$ (50 ml) was added slowly 3,5-bis(trifluoromethyl)-benzaldehyde (15 g, 62 mmol) at 0° C. under nitrogen. To this mixture was added $Na_2SO_4$ (4 g) and it was stirred overnight at RT. $Na_2SO_4$ was filtered off and $CH_2Cl_2$ was removed to give a clear oil which was redissolved in absolute EtOH (100 ml). To this solution was added $NaBH_3CN$ (5.3 g, 84 mmol) and acetic acid (20 ml). The mixture was stirred overnight under nitrogen. After the reaction was complete, the mixture was concentrated under vacuum to give a residue which was redissolved in EtOAc and brine, basified to pH 8. The product was extracted from the aqueous solution with EtOAc (100 ml, 2×) and washed with brine (100 ml 2×). The EtOAc fractions were combined and dried over $MgSO_4$, filtered and concentrated to give an oil (20 g). The product was purified by flash chromatography on flash grade silica gel (500 g) and eluted with 2.5% $MeOH/CH_2Cl_2$ to yield 17.3 g (44.78 mmol, 80%) of N-t-BOC-N'-3,5-bis(trifluoromethyl)phenyl ethylene diamine. FAB mass |M+1|⁺ 387.2.

A mixture of the above product (10.5 g, 272 mmol), 3,4-dichlorophenacyl bromide (7.3 g, 272 mmol) and diisopropylethylamine (3.9 g, 30 mmol) in dry THF (50 ml) was stirred at RT under nitrogen overnight. After the reaction was complete, the white solid was filtered off and the filtrate was concentrated under vacuum to give a residue which was triturated with ether and the solid was filtered off. The ether solution was concentrated to give a crude brown oil (16 g) which was used for the next reaction without purification. FAB mass [M+1]⁺ 573.575

To a solution of the above product (16 g, 27.9 mmol) in $CH_2Cl_2$ (10 ml) was added trifluoroacetic acid (18 ml) and the mixture was stirred at RT for 3 hours under nitrogen. The excess TFA and solvent were removed under vacuum and the resulting brown oil was redissolved in MeOH (50 ml) and removed again under vacuum to give a brown solid. The brown solid was suspended in MeOH (100 ml) and $NaBH_3CN$ (3.5 g, 55.8 mmol) was added portionwise. After overnight, the solvent was removed. To the residue was added $CH_2Cl_2$ (200 ml) and brine (200 ml), then basified with 3N NaOH to pH 10. The product was extracted from the aqueous solution with $CH_2Cl_2$ (100 ml, 2×), dried over $MgSO_4$, filtered, and the filtrate was concentrated under vacuum to give a light brown oil (12.5 g). The product was purified by flash chromatography on flash grade silica gel (300 g) and eluted with 2% $MeOH/CH_2Cl_2$ to give a light brown oil (10.5 g, 22.97 mmol, 83%).

A portion of this oil (0.2 g, 0.435 mmol) was dissolved in MeOH (92 ml) and treated with 2.35M HCl/MeOH (0.4 ml, 0.94 mmol). After stirring for 10 minutes at RT, the solvent was removed and dried under vacuum to give the title compound as a white solid (0.25 g), m.p. 234°–236° C.; FAB mass [M+1]⁺ 457.459; Found, C, 42.67; H, 3.40; N, 5.29; Cl, 26.70; F, 21.38. Calcd. for $C_{19}H_{16}N_2Cl_2F_6$.2 HCl, C,43.04; H, 3.42; N, 5.28; Cl, 26.75; F, 21.50.

EXAMPLE 13

Preparation of (+, −)-4-[[3,5-bis(trifluoromethyl) phenyl]methyl]-2-(3,4-dichlorophenyl)-1-[[[1-(phenylmethyl)-4-piperidinyl]amino]acetyl]-piperazine

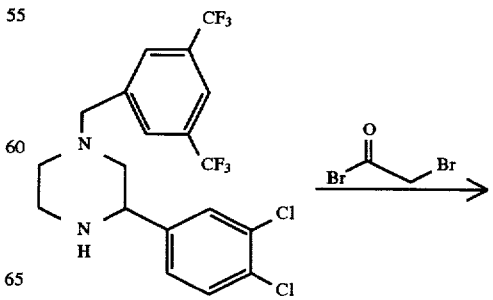

-continued

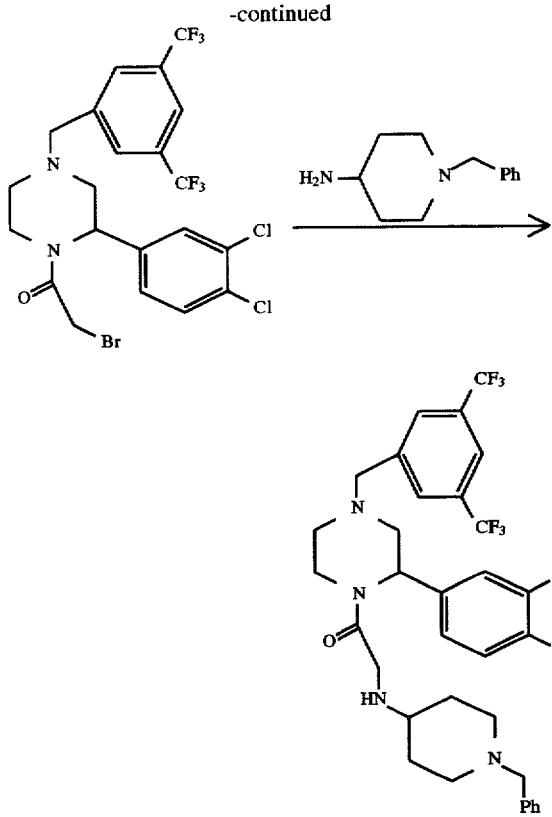

By a procedure analogous to the procedure described in the first part of Example 2. using (+, −)-1-[[3,5-bis(trifluoromethyl)phenyl]-methyl]-3-(3,4-dichlorophenyl)-piperazine in place of (+, −)-1-[[3,5-bis-(trifluoromethyl)-phenyl]methyl]-3-phenyl-piperazine, the bromoacetyl derivative was obtained in 78% from its starting material as a solid, m.p. 146°–148° C.; FAB mass [M+1]$^{+35}$Cl 577, 579.

By a procedure analogous to the procedure described in the second part of Example 2. the title compound was obtained as a solid (48%) after purification by flash chromatography on flash grade silica gel (70 g), eluting with 4% MeOH/CH$_2$Cl$_2$, m.p. 53°–55° C.; FAB mass [M+1]$^{+35}$Cl 687; Found. C. 56.98; H. 4.72; N. 8.13; Cl. 10.67; F. 16.30. Calcd. for C$_{33}$H$_{34}$N$_4$Cl$_2$F$_6$O.0.25 H$_2$O. C, 57.27; H, 5.03; N, 8.10; Cl, 10.25; F. 16.47.

By a procedure analogous to the procedure described in Example 2. but using (+, −)-1-[[3,5-bis(trifluoromethyl)phenyl]methyl]-3-(3,4-dichlorophenyl)-piperazine in place of (+, −)-1-[[3,5-bis(trifluoromethyl)-phenyl]methyl]-3-phenyl-piperazine, and employing appropriate heterocyclic derivatives (Z group), listed below, in place of 4-amino-1-benzyl-piperidine, the following compounds were prepared.

EXAMPLE 14

| Z | m.p. °C. | FAB mass [M + 1]$^+$ based on $^{35}$Cl | [M + 1]$^+$ High Res. Mass |
|---|---|---|---|
| H$_3$CC(=O)—NH— (4-acetamido-4-phenyl-piperidin-1-yl) | free form 108–110 | | Cal'd 715.2041 Found 715.2050 |
| Ph-CH$_2$-N(piperazin-1-yl)— | 2H$_2$O 58–60 | | Cal'd 673.1936 Found 673.1935 |

-continued
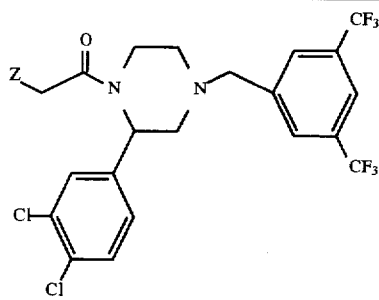
| Z | m.p. °C. | [M + 1]⁺ FAB mass based on $^{35}$Cl | [M + 1]⁺ High Res. Mass |
|---|---|---|---|
|  | free form 55–57 | 672 | |
| 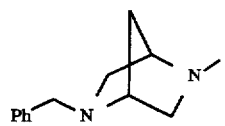 | 0.25H$_2$O 55–57 | 685 | |
| 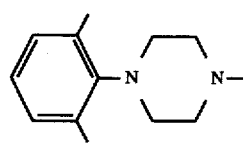 | free form 74–76 | 687 | |
| 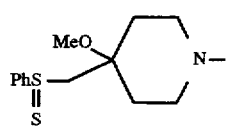 | free form 82–83 | 750 | |
| 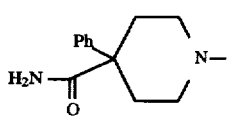 | free form 105–107 | 702 | |
|  | free form 85–86 | 674 | |

EXAMPLE 15

Preparation of (+, −)-1-[2-[4-[[3,5-bis(trifluoromethyl)phenyl]methyl]-2-(3,4-dichlorophenyl)-1-piperazinyl]ethyl]-4-phenyl-4-piperidinol

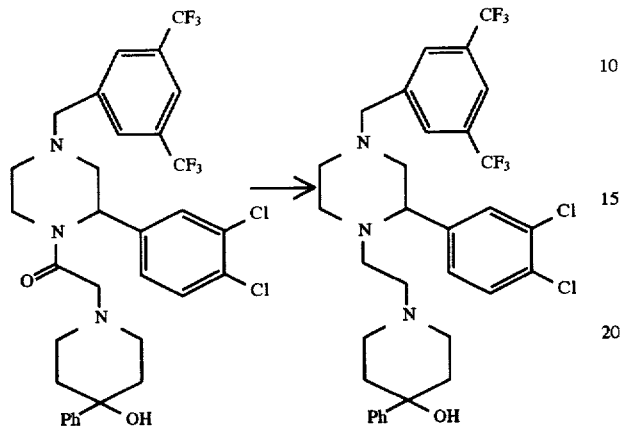

By a procedure analogous to the procedure described in Example 4, using the last compound from Example 14, as a starting material, the title compound was prepared in 67% yield as a solid, m.p. 71°–72° C.; FAB mass [M+1]$^+$ $^{35}$Cl 660; Found, C, 58.08; H, 5.14; N, 6.40; F, 17.37. Calcd. for C$_{32}$H$_{33}$N$_3$Cl$_2$F$_6$O, C, 58.19; H, 5.04; N, 6.36; F, 17.26.

EXAMPLE 16

Preparation of (+, −)-4-[[3,5-bis(trifluoromethyl)phenyl]acetyl]-2-phenyl-1-[[[1-(phenylmethyl)-4-piperidinyl]amino]acetyl]piperazine

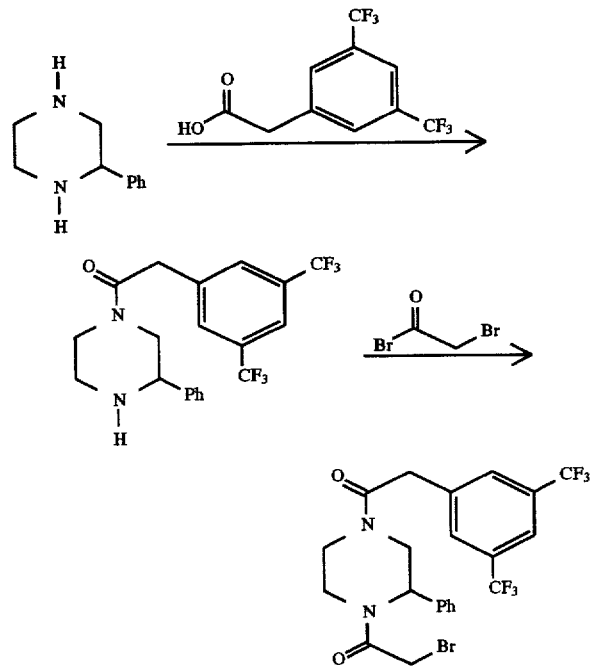

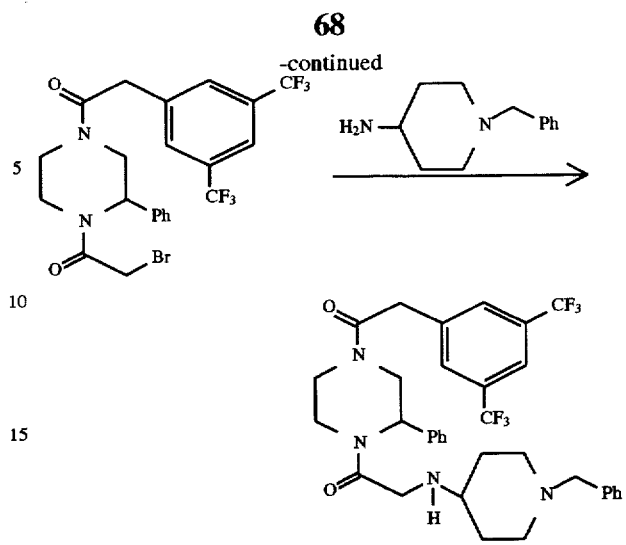

To cooled CH$_2$Cl$_2$ (127 ml) containing 2-phenylpiperazine (Example 1, 1.0 gram, 6.164 mmol), 3,5-bis(trifluoromethyl)phenylacetic acid (1.797 g, 6.472 mmol), and N-hydroxybenzotriazole monohydrate (0.874 g, 6.472 mmol) at −20° C. were added Et$_3$N (0.9 ml, 6.472 mmol) and N,N-dimethylaminopropylethylcarbodimide (DEC) under nitrogen. The reaction was kept at −20° C. for an hour and gradually warmed to RT overnight. After stirring 20 hours, the reaction was complete and CH$_2$Cl$_2$ (200 ml) was added. The organic solution was washed with 5% NaHCO$_3$ (100 ml) and brine (100 ml, 3×), dried over MgSO$_4$, filtered and concentrated under vacuum to give 2.5 g of crude product. The product was purified by flash chromatography on flash grade silica gel (120 g), eluting with 3% NH$_3$-MeOH/CH$_2$Cl$_2$ to give a gummy solid (2.08 g, 4.996 mmol, 81%). A portion of this solid (1.0 g) was crystallized from hexane and characterized to yield a solid, m.p. 80°–82° C.; FAB mass [M+1]$^+$ 417.2; Calcd. for C$_{20}$H$_{18}$ON$_2$F$_6$, C, 57.69; H, 4.36; N, 6.73; F, 27.38. Found, C, 57.91; H, 4.55; N, 6.69; F, 27.61.

To a solution of the above compound (1.11 g, 2.642 mmol) in dry CH$_2$Cl$_2$ (22.2 ml) at −78° C. was added diisopropylethylamine (0.483 ml, 2.774 mmol) followed by the dropwise addition of bromoacetyl bromide (0.246 ml, 2.774 mmol). After stirring at −78° C. for 7 hours under nitrogen, additional diisopropylethylamine (0.51 ml, 2.9 mmol) and 4-amino-1-benzylpiperidine (0.605 ml, 2.9 mmol) were added at −78° C. The reaction was gradually warmed to RT overnight. After the reaction was complete, the reaction was diluted with CH$_2$Cl$_2$ (150 ml), washed with brine (50 ml, 3×) and dried over MgSO$_4$. After filtration, the solvent was removed under vacuum to give a light yellow solid which was purified by flash chromatography on flash grade silica gel (150 g), eluting with 5% NH$_3$-MeOH/CH$_2$Cl$_2$ to give the title compound as a white solid (0.94. g, 1.453 mmol, 55%), m.p.49–52° C.; FAB mass [M+1]$^+$ 647.3°; Calcd. for C$_{34}$H$_{36}$O$_2$N$_4$F$_6$, C, 63.15; H, 5.16; N, 8.66; F, 17.62. Found, C, 62.73; H, 5.77; N, 8.56; F, 17.68.

EXAMPLE 17

Preparation of (+, −)-4-|2-|3,5-bis(trifluoromethyl) phenyl|ethyl|-2-phenyl-N-| 1-(phenylmethyl)-4-piperidinyl|-1-piperazineethanamine, four hydrochloride salt, hemihydrate

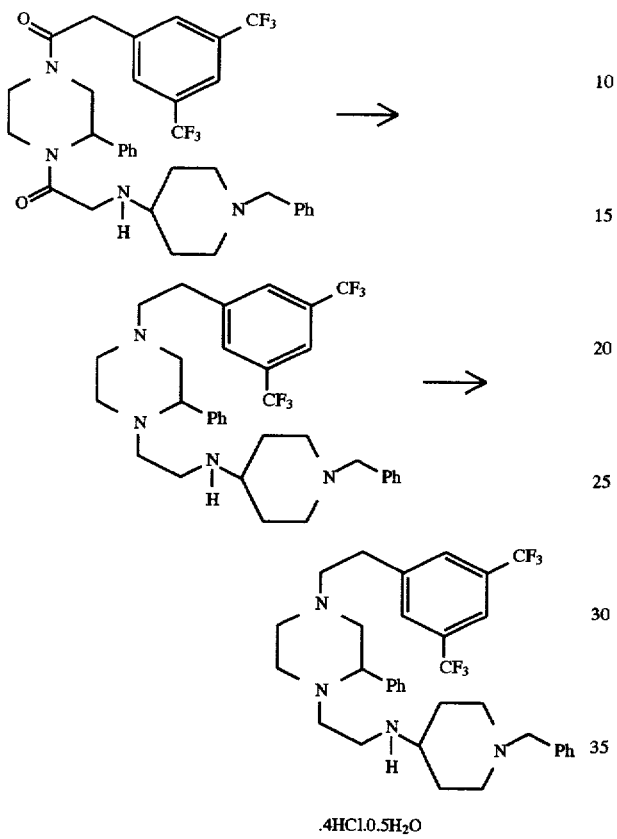

To a solution of the product from Example 16 (0.463 gram, 0.72 mmol) in dry THF (21.6 ml) was added a 10M solution of $BH_3.S(CH_3)_2$ (0.716 ml, 7.16 mmol) at RT under nitrogen. The solution was heated at 80° C. under nitrogen for 24 hours. After cooling to RT, MeOH (5 ml) was added slowly to decompose excess $BH_3.S(CH_3)_2$. All solvents were removed under vacuum and the residue was redissolved in absolute EtOH (14.1 ml), followed by the addition of $K_2CO_3$ (0.22 g, 1.58 mmol). The mixture was heated at 80° C. for 6.5 hours under nitrogen. After cooling $K_2CO_3$ was filtered and EtOH was removed to give a residue which was redissolved in EtOAc (150 ml) and washed with brine (50 ml, 2×). It was dried over $MgSO_4$, filtered, and evaporated under vacuum to give a solid (0.42 g) which was purified by flash chromatography on flash grade silica gel (80 g), eluting with 4% $NH_3$-MeOH/$CH_2Cl_2$ to give a white solid (0.14 g, 0.227 mmol, 49%).

The above material (0.14 g, 0.227 mmol) was treated with $CH_2Cl_2$ (6.8 ml) and 2.3M HCl-EtOH (0.592 ml, 1.362 mmol). After stirring at RT for 10 minutes, the solution was evaporated under high vacuum to give a white solid, m.p. 182°–190° C.; High Res. MS |M+1|$^+$; Calcd. for $C_{34}H_{41}N_4F_6$, 619.3235, Found, 619.3222. Calcd. for $C_{34}H_{40}N_4F_6$.4 HCl.0.5 $H_2O$, C, 52.79; H, 5.86; N, 7.24, F, 14.73; Cl, 18.33. Found, C, 52.58; H, 6.10; N, 7.21; F, 14.77; Cl, 16.71.

EXAMPLE 18

Preparation of (+, −)-2-phenyl-1-[[[(1-phenylmethyl)-4-piperidinyl]amino]acetyl]-4-[(3,4, 5-trimethoxylphenyl)acetyl]piparazine, hemihydrate

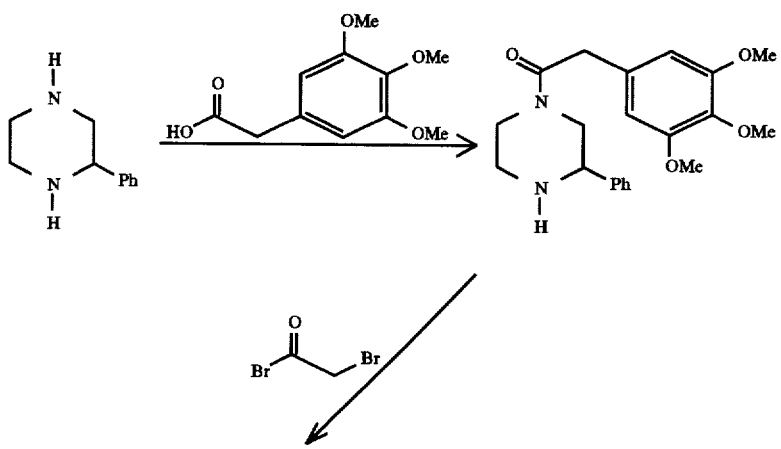

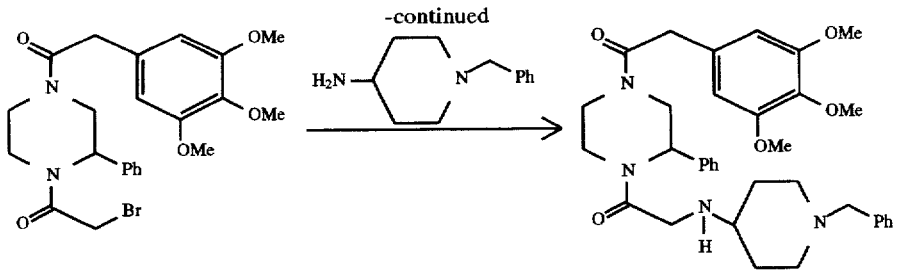

By a procedure analogous to the procedure described in Example 16, using 3,4,5-trimethoxyphenylacetic acid in place of 3,5-bis(trifluoromethyl)phenylacetic acid, the title compound was prepared as a solid, m.p. 53°–56° C., High Res. MS:[M+1]$^+$ Calcd. for $C_{35}H_{45}N_4O_5$ 601.3390; Found, 601.3393. Calcd. for $C_{35}H_{44}N_4O_5 \cdot 0.5\ H_2O$, C, 68.94; H, 7.43; N, 9.19. Found, C, 69.21; H, 7.53; N, 9.22.

EXAMPLE 19

Preparation of (+, −)-2-phenyl-N-[1-(phenylmethyl)-4-piperidinyl]-4-[2-(3,4,5-trimethoxyphenyl)ethyl]-1-piperazineethanamine, four hydrochloride salt, monohydrate

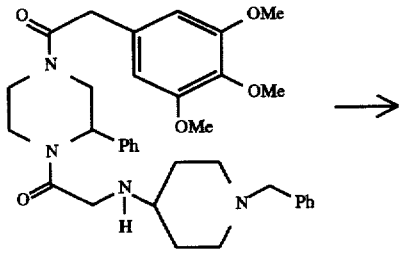

By essentially the same process as described in Example 17, using the product from Example 18 in place of the product from Example 16, the title compound was prepared as a solid, m.p. 167° C. (wet, no sharp melting point); High Res. MS: [M+1]$^+$ Calcd. for $C_{35}H_{49}N_4O_3$, 573.3805. Found, 573.3810. Calcd. for $C_{35}H_{48}N_4O_3 \cdot 4\ HCl \cdot H_2O$, C, 57.07; H, 7.39; N, 7.61; Cl, 19.25. Found, C, 57.16; H, 7.88; N, 7.64, Cl, 18.71.

EXAMPLE 20

Preparation of (+/−)-4-|2-|3,5-bis(trifluoromethyl)phenyl)ethyl|-2-phenyl-1-|||1-(phenylmethyl)-4-piperidinyl|amino|acetyl|piperazine, trihydrochloride salt

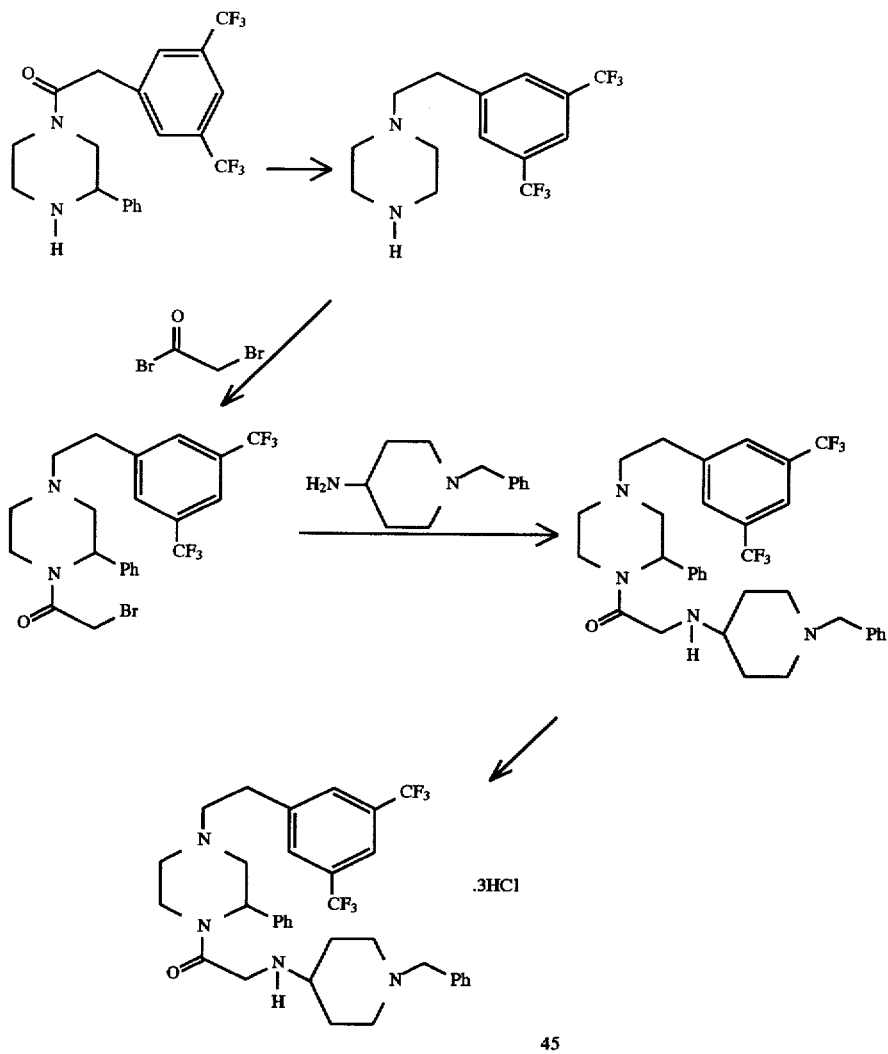

By a process analogous to the reduction process described in the first part of Example 17, using (+, −)-[[3,5-bis-(trifluoromethyl)phenyl]acetyl]-3-phenylpiperazine (described in the first part of Ex. 16) as a starting material, (+, −)-4-[2-[bis(trifluoromethyl)phenyl]ethyl]-2-phenyl piperazine was prepared as a solid after purification by flash chromatography, m.p. 193°–195° C., FAB mass [M+1]$^+$ 403.3. This material (0.38 g, 0.94 mmol) was converted to its bromoacetylderivative according to the same procedure as described in the second step of Example 16. After reaction was complete, the material was alkylated with 4-amino-1-benzylpiperidine without isolation, using the same procedure as described in the third step of Example 16. The title compound was obtained as a solid by flash chromatography, then converted to its HCl salt by treatment with HCl/MeOH solution. m.p. 214°–216° C., High Res. MS: [M+1]$^+$ Calcd. for $C_{34}H_{39}N_4OF_6$, 633.3028; Found, 633.3034.

EXAMPLE 21

Preparation of (+, −)-2-phenyl-1-[[[(1-phenylmethyl)-4-piperidinyl]amino]acetyl]-4-[2-(3,4,5-trimethoxyphenyl)ethyl]piperazine

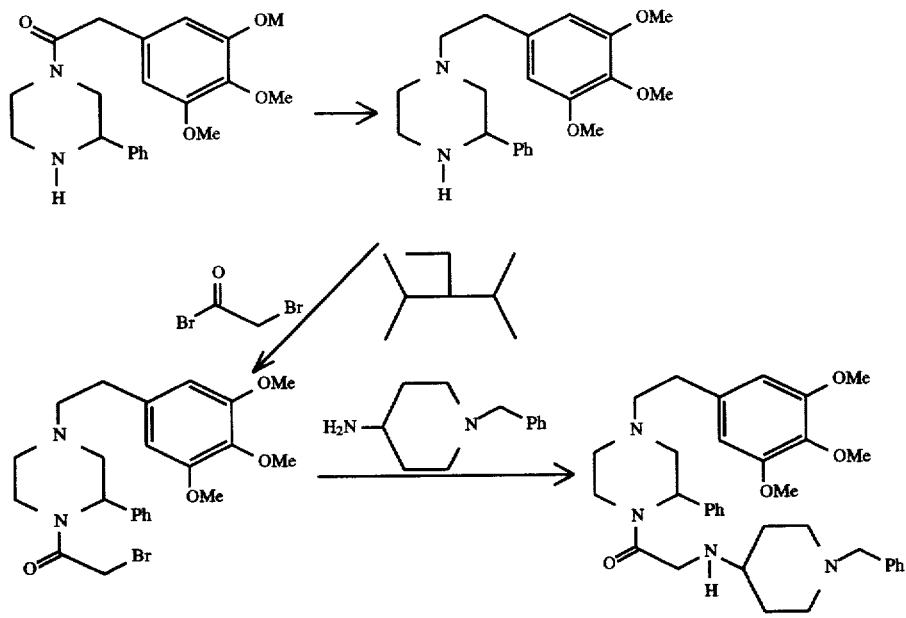

By a reduction process analogous to that described in the first part of Example 17, using (+, −)-3-phenyl-1-[(3,4,5-trimethoxyphenyl)acetyl]piperazine as a starting material (described in the first part of Example 18) (+, −)-2-phenyl-4-[[2-(3,4,5-trimethoxy)phenyl]ethyl]-piperazine was prepared as a solid after purification by flash chromatography. m.p. 160°–162° C., FAB mass [M+1]$^+$ 357.4. This material (0.53 g, 1.48 mmol) was converted to its bromoacetyl derivative according to the same procedure as described in the second step of Example 16. After reaction is complete, the bromoacetyl derivative is alkylated in situ with 4-amino-1-benzylpiperidine, using the same procedure as described in the third step of Example 16.

The title compound can be obtained and purified by flash chromatography.

EXAMPLE 22

Preparation of (+, −)-4-[[3,5-bis(trifluoromethyl)phenyl]methyl]-6-(3,4-dichloro-phenyl)-1-[2-[[1-(phenylmethyl)-4-piperidinyl]amino]ethyl]2-piperazinone

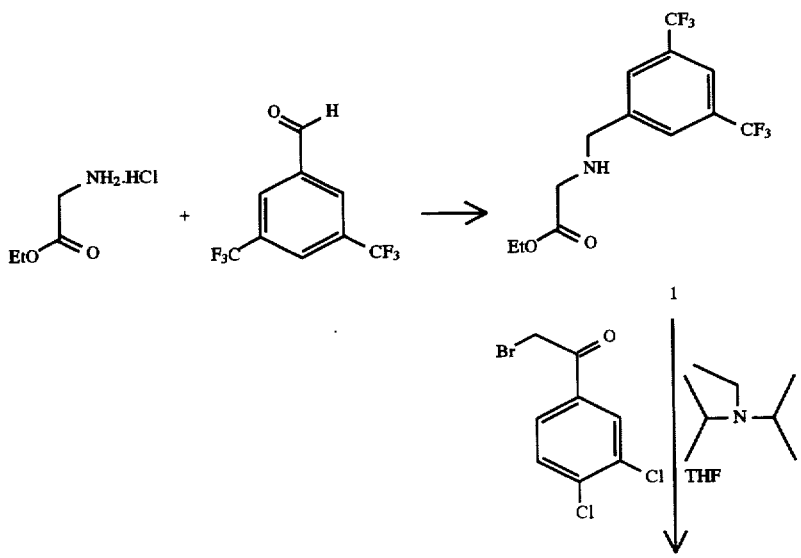

-continued

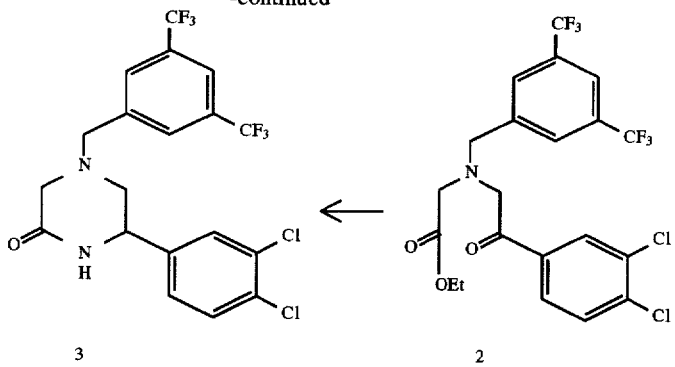

A mixture of glycine ethylester hydrochloride salt (2.9 gram, 20.6 mmol), 3,5-bis(trifluoromethyl)benzaldehyde (5.0 g, 20.6 mmol) and triethyl amine (2.1 g, 20.6 mmol) in MeOH (70 ml) was stirred at RT for 40 minutes under nitrogen. To the above solution was added acetic acid (20 ml) and NaBH₃CN (2.6 g, 41.2 mmol). After stirring at RT for 4 days, half of the solvent was removed and AcOH (10 ml) was added then stirred at RT for an additional two days. All solvent was removed to give a white paste which was mixed with $CH_2Cl_2$ (100 ml) and brine (50 ml), and basified with 3N NaOH to about pH 10. The product was extracted from the aqueous solution with $CH_2Cl_2$, dried over $MgSO_4$, filtered and evaporated to give an oil (7.5 g). The product was purified by flash chromatography on flash grade silica gel (170 g), eluting with 20% EtOAc/Hexane to give compound (1) (2.7 g) FAB mass [M+1]⁺ 330.

Compound(1) (4.92 g, 14.76 mmol), obtained from a large scale preparation, was dissolved in THF (80 ml) and treated with Hunig's base (1.89 g, 14.76 mmol) and 3,4-dichlorophenacyl bromide (4.35 g, 16.4 mmol). The solution was stirred at RT under nitrogen for 3 days. After reaction was complete, THF was removed under vacuum and the residue was dissolved in $CH_2Cl_2$-ether (800 ml), washed with brine (200 ml, 3×), dried over $Na_2SO_4$, filtered and evaporated under vacuum to give a brown gum. Product was purified by flash chromatography to give compound (2) as a light paste. FAB mass [M+1]⁺ ³⁵Cl, 516.

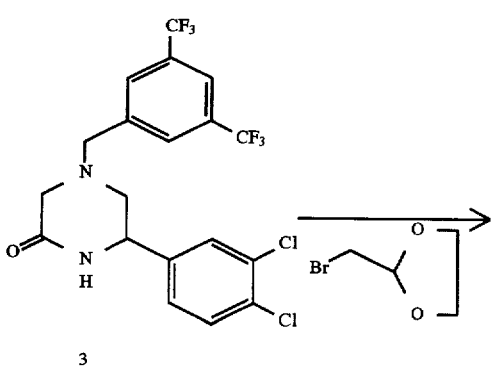

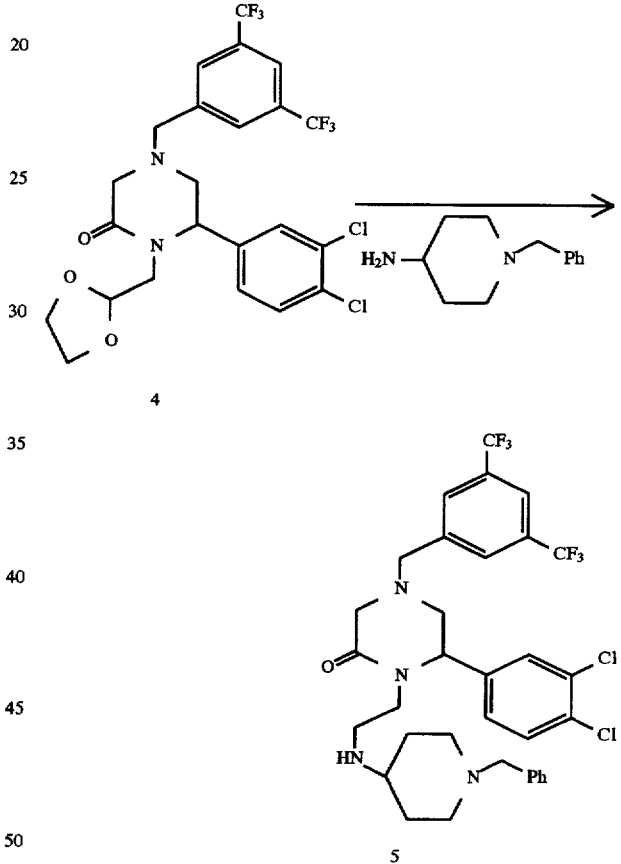

A mixture of compound (2) and 1.2 equivalents of $NH_4OAc$ is heated at appropriate temperature to form compound (3). The compound (3) is treated with NaH/DMF and alkylates with 2-bromomethyl-1,3-dioxolane to give compound (4). After removal the protecting group of compound (4) with HCl/dioxane, the desired compound (5) is obtained by reductive amination (NaBH₃CN/MeOH) with 4-amino-1-benzyl-piperidine.

The following compounds can be prepared by employing essentially the same processes covered from Example 1 to Example 22 with appropriate starting materials and reagents, as described above.

EXAMPLES OF COMPOUND 22
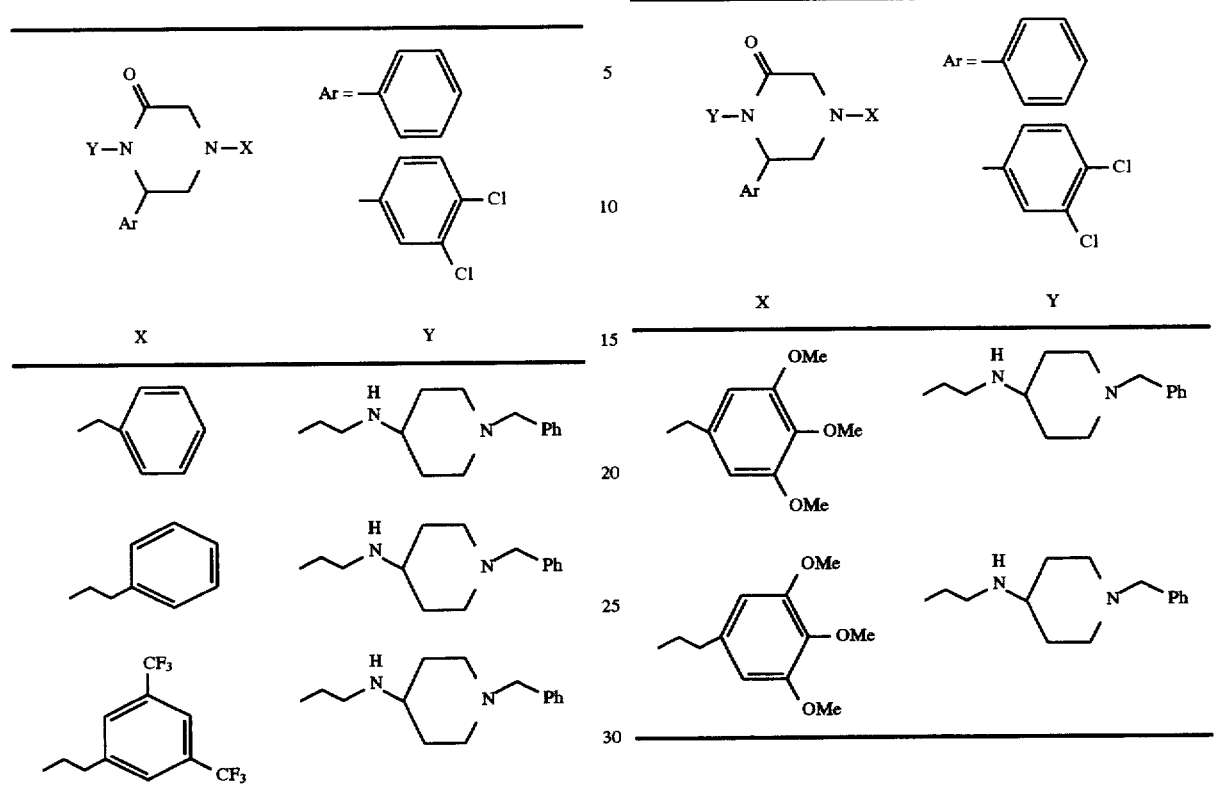
EXAMPLES OF COMPOUND 22C
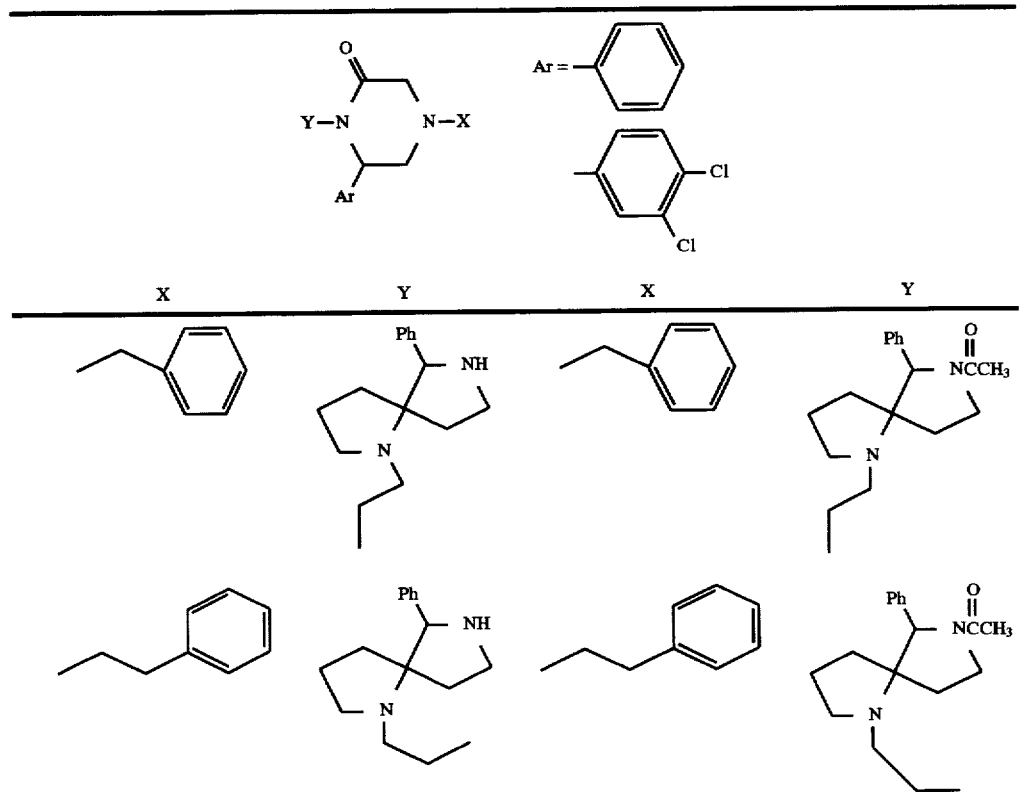

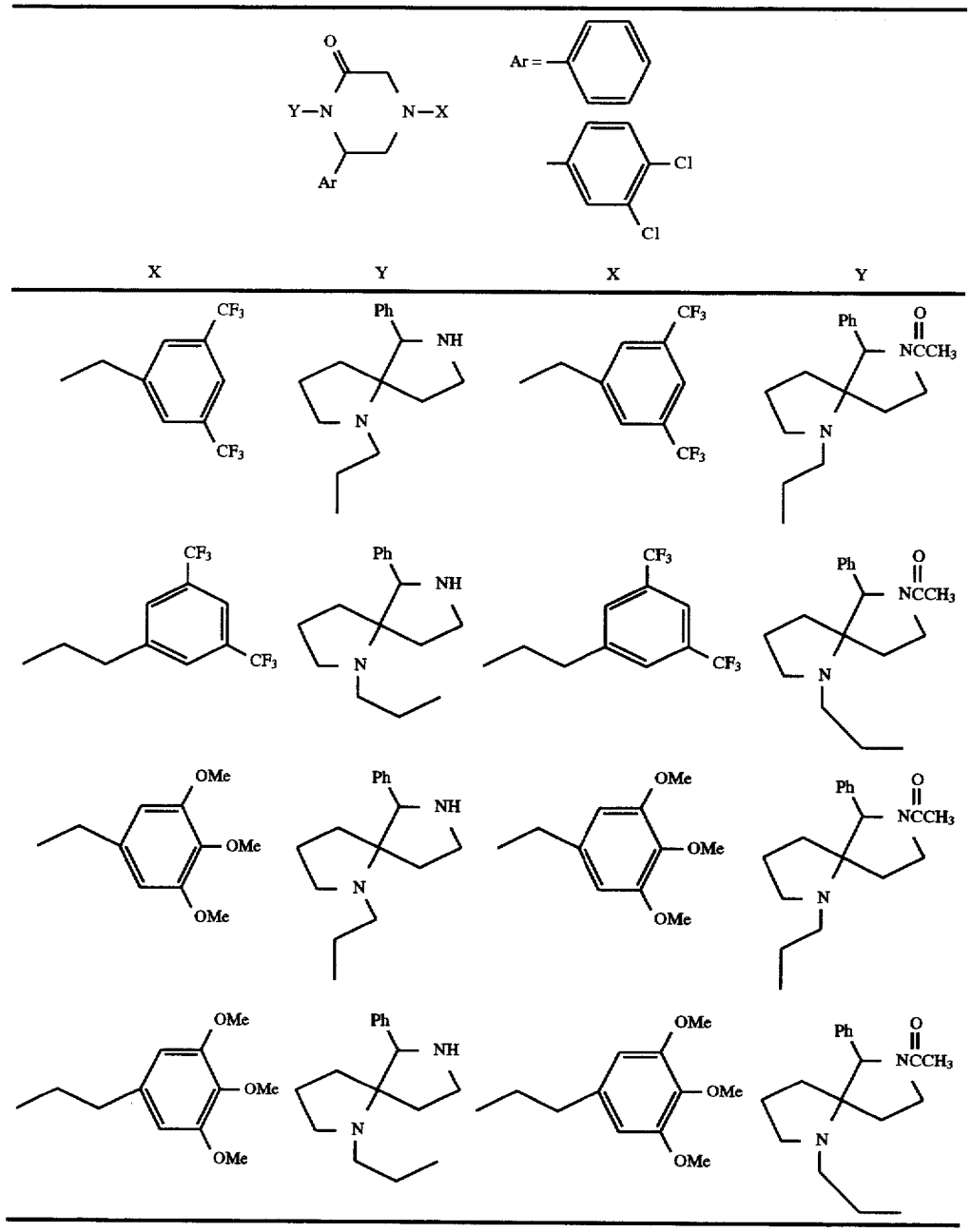
EXAMPLE 23
The following compounds can be prepared by employing processes analogous to those set forth in Examples 1 to Example 22 using appropriate starting materials and reagents, as described above. Those compounds just below, which have been given without any physical data, have not been made. Those compounds just below which have melting points, have been made.

EXAMPLE 23
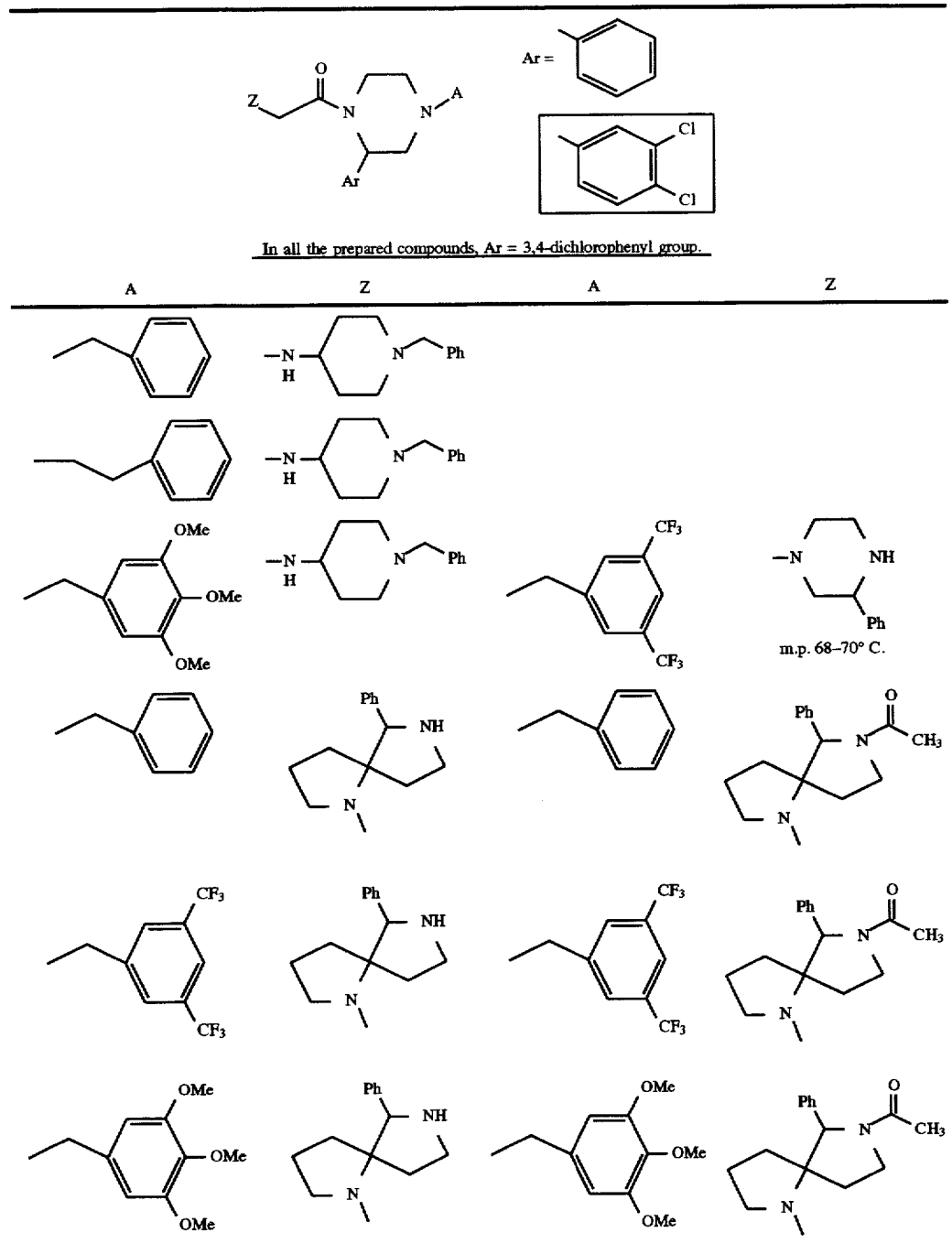

EXAMPLE 24

Preparation of (+, −)-1-[[3,5-bis(trifluoromethyl)phenyl]methyl]-5-(3,4-dichlorophenyl)-4-[[1-(phenylmethyl)-4-piperidylamino]acetyl]2-piperazinone Scheme 24

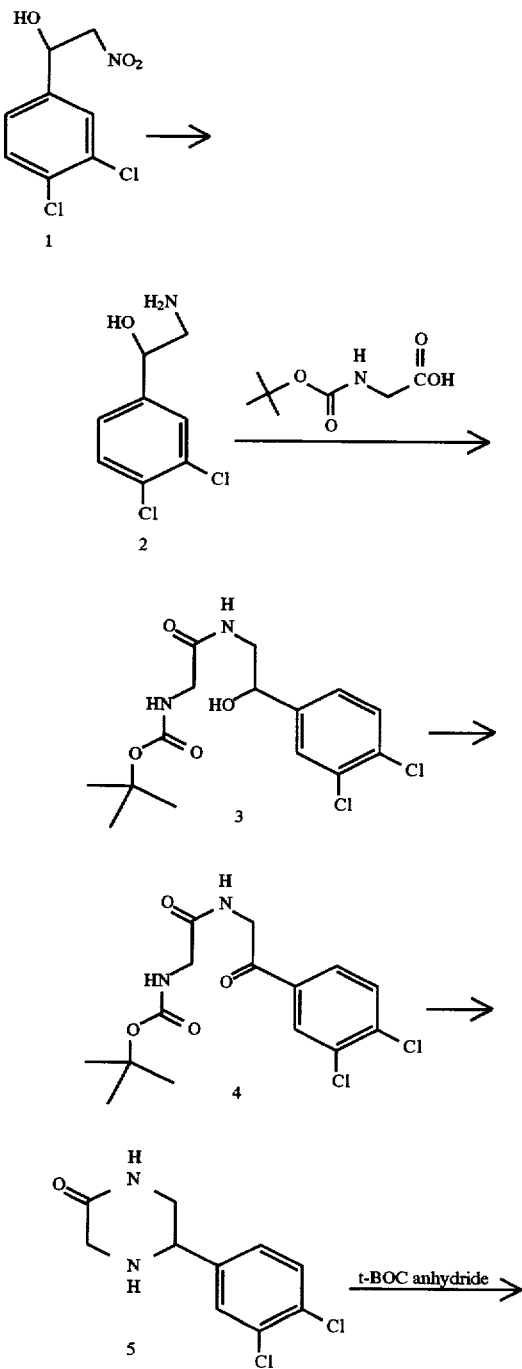

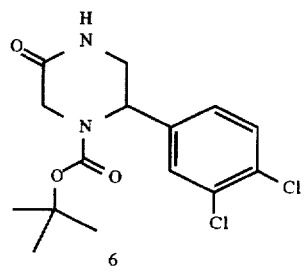

To a solution of 3,4-dichloro-1-(1-hydroxy-2-nitro)ethylbenzene (6.2 g, 27.92 mmol) in THF(100 ml) at 0° C. was added slowly a DME solution of 0.5M LiAlH$_4$ (200 ml, 100 mmol) under argon. The ice-water bath was removed after the addition of LAH. After stirring at RT for 5 hours, the reaction was slowly quenched with dropwise addition of saturated Na$_2$SO$_4$ solution (45 ml) under argon. It was stirred at RT for one hour and precipate was filtered. The filtrate was concentrated under vacuum to give a light brown oil. The product (2) was purified by flash chromatography on flash grade silica gel (200 g) and eluting with 2.5% NH$_3$-MeOH-CH$_2$Cl$_2$. FAB mass for C$_8$H$_9$ONCl$_2$ [M+1]$^+$ $^{35}$Cl, 206.

To a solution of the above product (2) (2.1 g, 10.19 mmol) in THF (210 ml) was added N-t-butoxycarbonyl glycine (1.91 g, 10.69 mmol) and N-hydroxybenzotriazole monohydrate (1.44 g, 10.69 mmol). The solution was cooled to −20° C. under nitrogen. To the cooled solution was added Et$_3$N (1.49 ml, 10.69 mmol) and N,N-dimethylaminopropylethylcarbodiimide (2.05 g, 10.69 mmol). The mixture was stirred at −20° C. for an hour then gradually warmed to RT overnight. After the reaction was complete, the reaction was diluted with CH$_2$Cl$_2$ (200 ml), washed with brine (150 ml, 3×), dried over MgSO$_4$, filtered and evaporated under vacuum. The crude product (3) was used without further purification. FAB Mass [M+1]$^+$ for $^{35}$Cl, 363.2.

Compound (3) was oxidized to the keto derivative (4) by PCC/CH$_2$Cl$_2$ at RT. FAB Mass [M+1]$^+$ for $^{35}$Cl, 361.1. Compound (4) was cyclized to compound (5) via in-situ reductive amination with NaBH$_3$CN in MeOH after removal of t-BOC protecting group. Compound (5) was protected with t-BOC anhydride in CH$_2$Cl$_2$ to give compound (6).

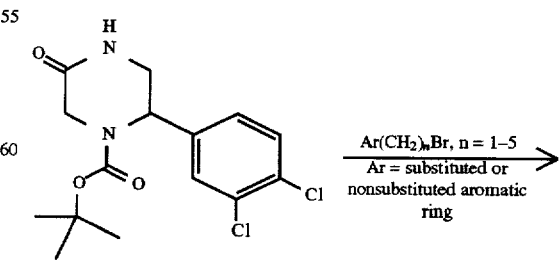

Ar(CH$_2$)$_n$Br, n = 1–5
Ar = substituted or nonsubstituted aromatic ring

87
-continued

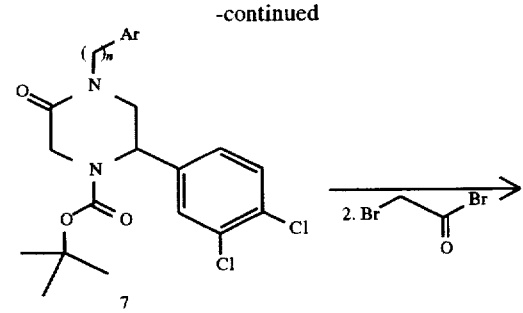

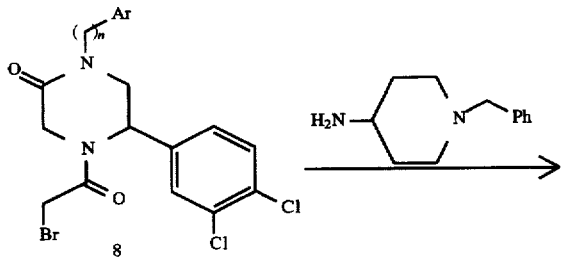

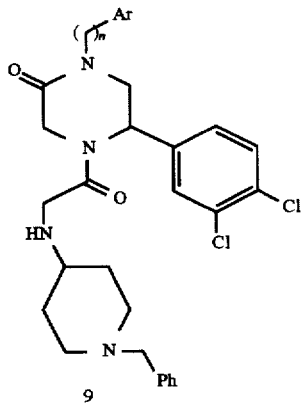

Compound (6) is treated with NaH/DMF and 3,5-bis(trifluoromethyl)benzylbromide to yield compound (7). After removal of t-BOC protecting group of (7), followed by acetylation with bromoacetylbromide, compound (8) is obtained. Alkylation of (8) with 4-amino-1-benzylpiperidine gives compound (9).

The following compounds are prepared by employing analogous processes covered from Example 1 to Example 24 with appropriate materials and reagents, as described above.

88
EXAMPLES OF COMPOUND 24A

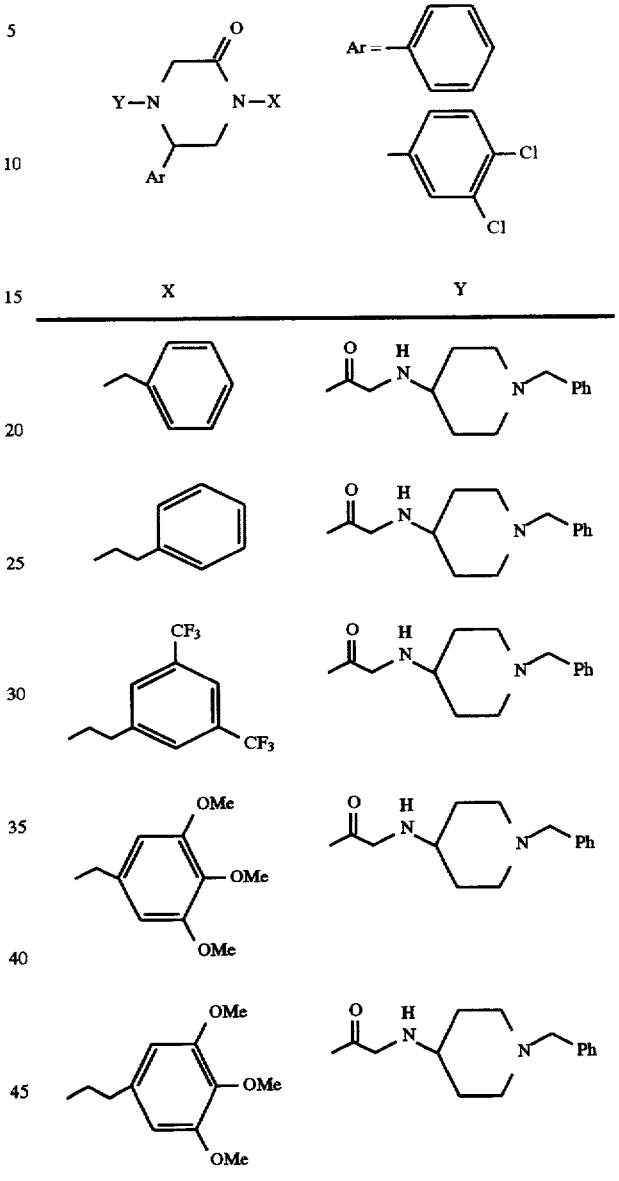

EXAMPLES OF COMPOUND 24C
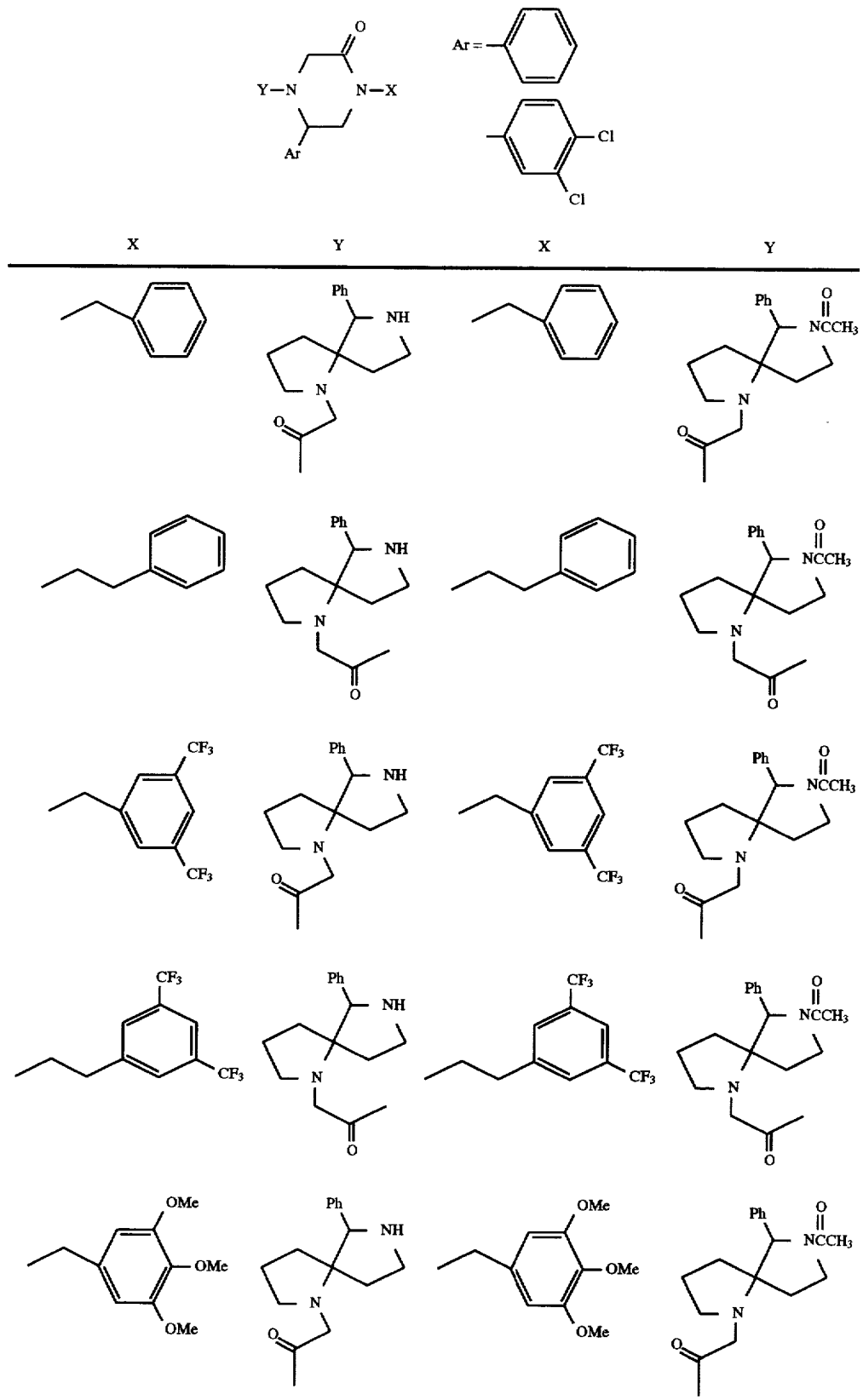

-continued
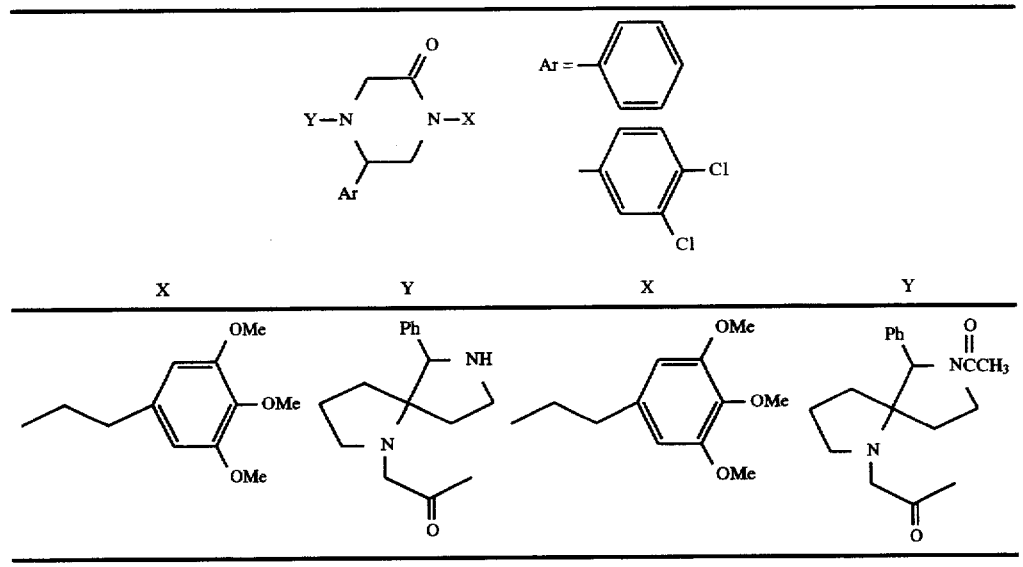
EXAMPLE 25
Preparation of (+, −)-1-[[3,5-bis(trifluoromethyl)phenyl]methyl]-5-(3,4-dichlorophenyl)-4-[[2-[1-(phenylmethyl)-4-piperidinyl]amino]ethyl]2-piperazone
General Method of Synthesis Example 25
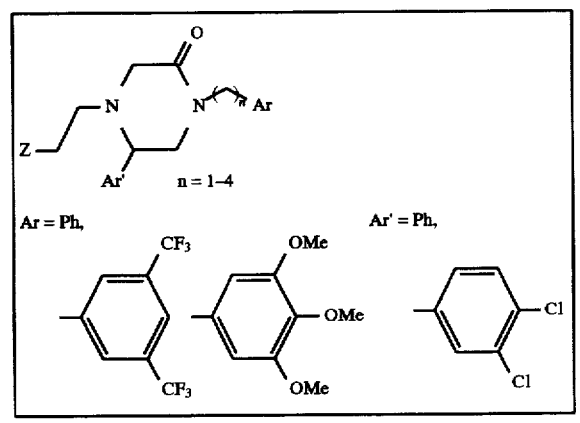
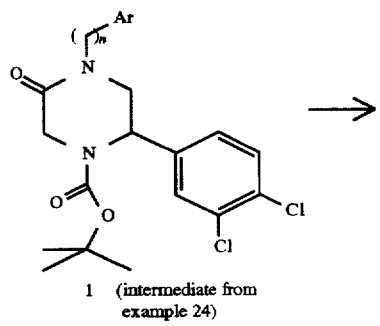
1 (intermediate from example 24)
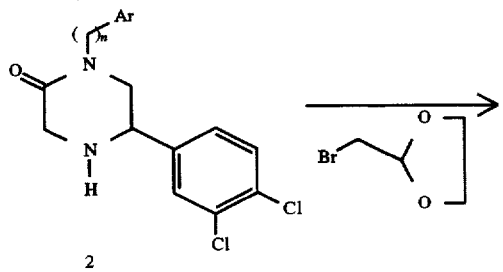
2
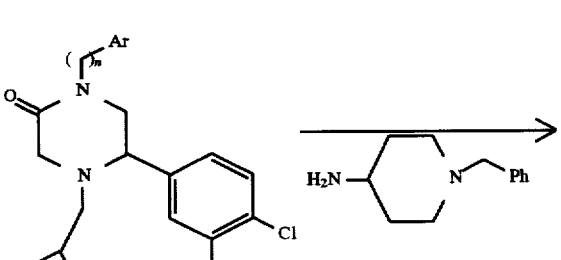
3
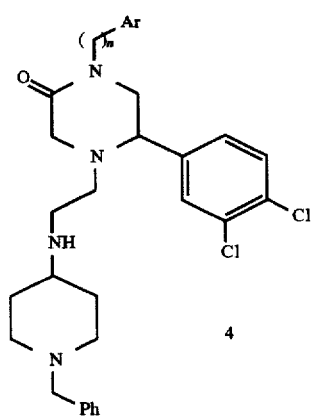
4

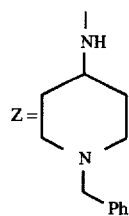

Using the intermediate 6 prepared in the example 24 as a starting material, compound 2 is obtained by removal the t-BOC protecting group with CF₃COOH. Treatment of 2 with Cs₂CO₃/DMF then alkylation with 2-bromomethyl-1, 3-dioxolane gives compound 3. Follow by removal the protecting group of 3 and in-situ reductive amination with 4-amino-1-benzylpiperidine in the presence of NaBH₃CN/MeOH, compound 4 is obtained.

The following compounds can be prepared by employing processes analogous to those set forth in Example 1 to Example 25 using appropriate materials and reagents, as described above.

EXAMPLES OF COMPOUND 25A

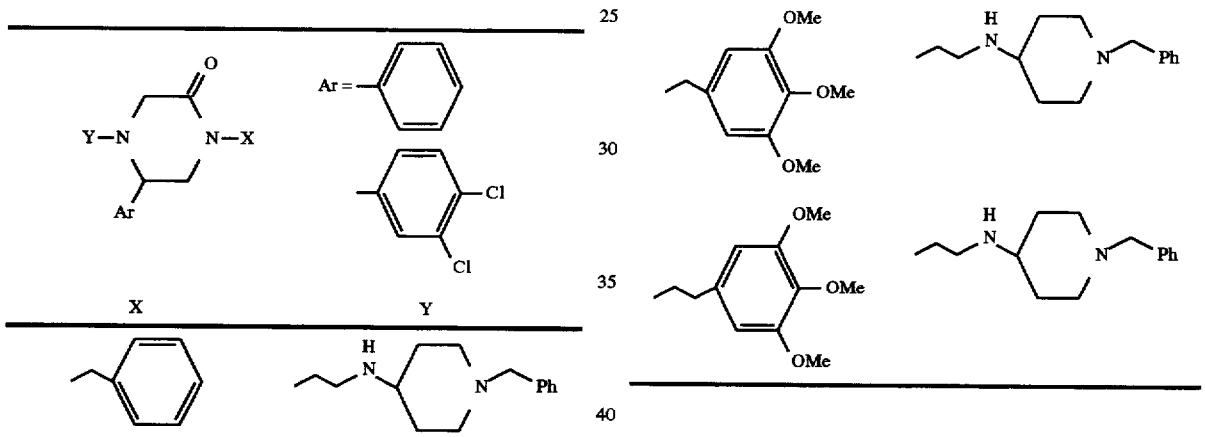

EXAMPLES OF COMPOUND 25C

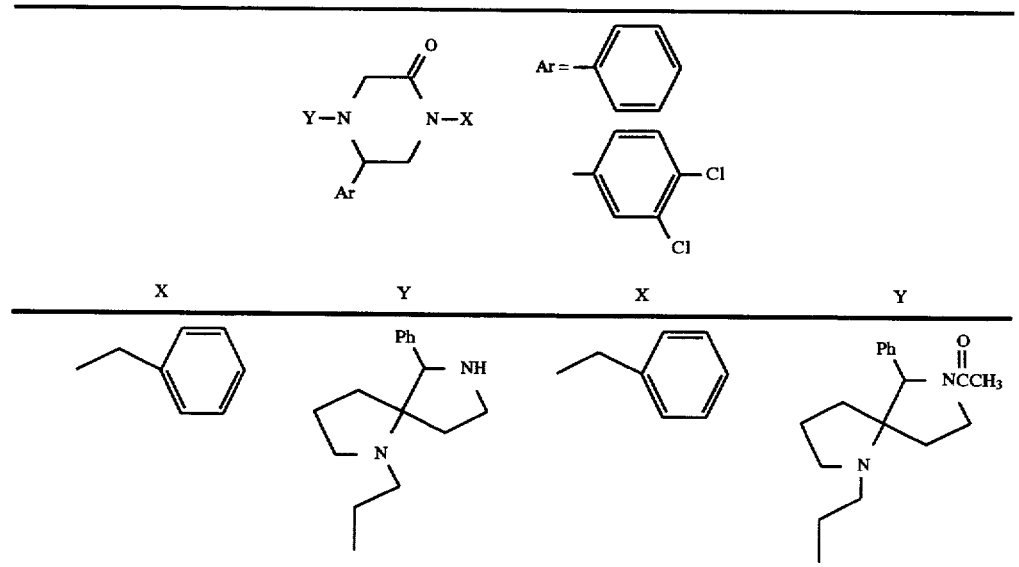

-continued
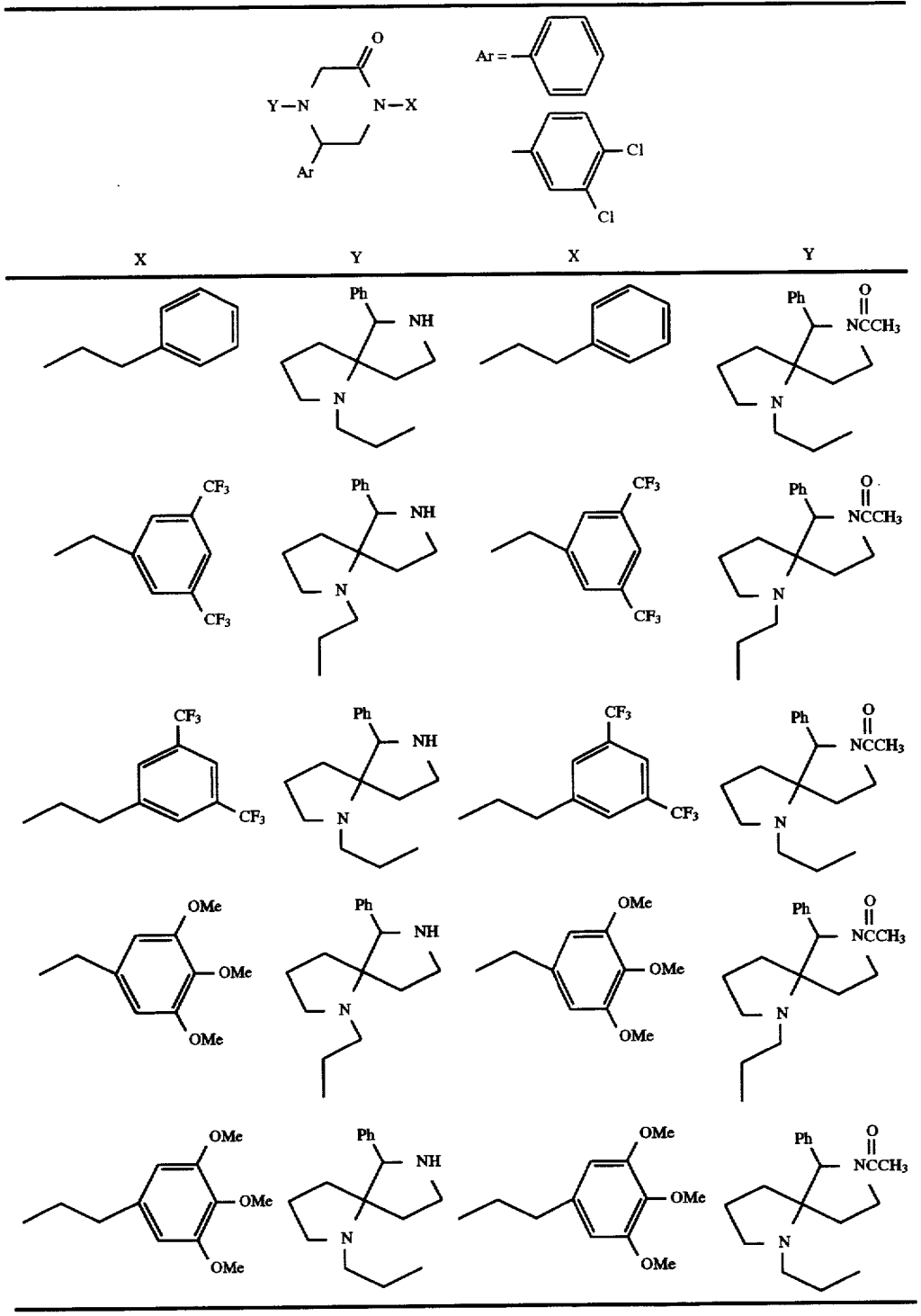

What is claimed is:

1. A compound of the formula:

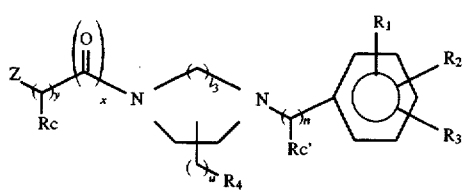

wherein each $R_1$ is independently selected from the group consisting of

H, $C_1$-$C_6$ alkyl, $CF_3$, $C_2F_5$, $NO_2$, $OR_a$, Cl, Br, I, F, $-O-\overset{O}{\overset{\|}{C}}-Ra$,

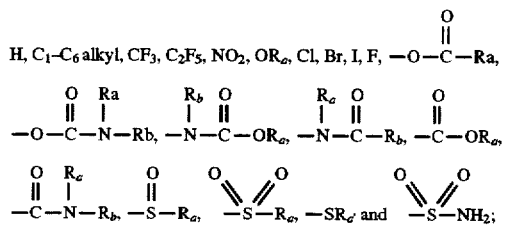

provided $R_a$ is not H in

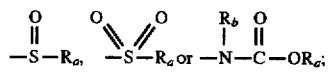

and each $R_2$, and $R_3$ is independently selected from the group consisting of H, $C_1$-$C_6$ alkyl, $OR_a$, Cl, Br, I, F, $-O-\overset{O}{\overset{\|}{C}}-Ra$, $-\overset{O}{\overset{\|}{C}}-OR_a$ and

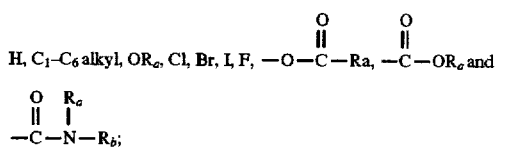

each $R_a$ and $R_b$ is independently selected from the group consisting of H, $C_1$-$C_6$ alkyl, $CF_3$, $C_2F_5$, phenyl, and benzyl;

each $R_c$ and $R_{c'}$ is selected from the group consisting of H, $C_1$-$C_6$ alkyl, $C_2$-$C_6$ alkenyl, $C_2$-$C_6$ alkynyl, unsubstituted or substituted phenyl, and unsubstituted or substituted benzyl, with the proviso that no more than one $R_c$ is other than H in the

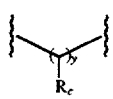

moiety, and no more than one $R_{c'}$ is other than H in the

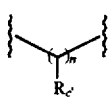

moiety;

$R_4$ is

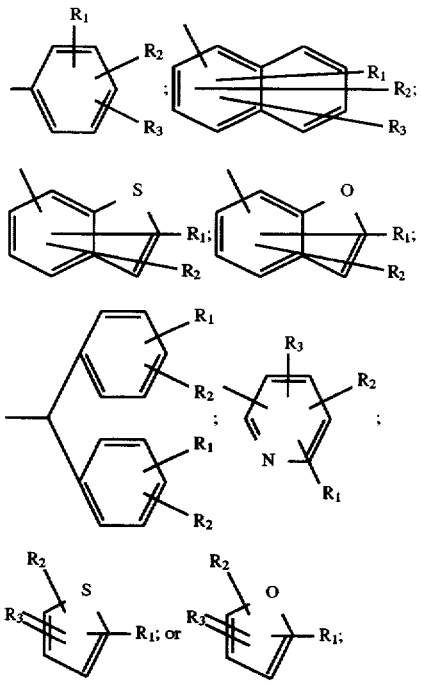

n is 0 to 5;

$l_3$ is 2, x is 0, and y is 2 to 4; or x is 1, and y is 0 to 3;

Z is

$p_1$ and $p_2$ are each independently 1 to 4 with the proviso that $p_1$ and $p_2$ added together are 2 to 6;

each t is 0 to 4;

each u is independently 0 to 2;

$R_5$ is selected from the group consisting of

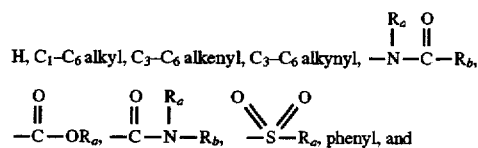

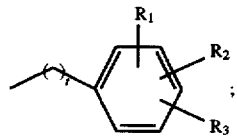

wherein $R_a$ is not H when $R_5$ is

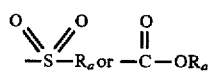

and with the proviso that when $R_5$ is $C_3$-$C_6$ alkenyl or $C_3$-$C_6$ alkynyl, the double or triple bond cannot be directly attached to nitrogen;

$R_6$ is selected from the group consisting of H, $C_1$–$C_6$ alkyl,

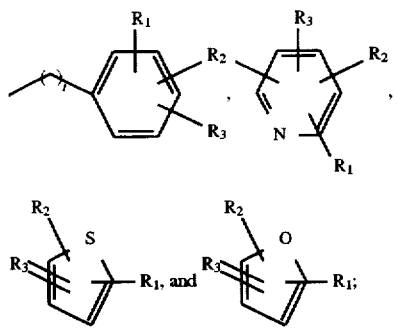

and wherein substituted means 1 to 3 substituents independently selected from the group consisting of H, $C_1$–$C_6$ alkyl, $CF_3$, $C_2F_5$, OH, $OC_1$–$C_6$ alkyl, Cl, Br, I and F;

or a pharmaceutically acceptable salt thereof.

2. A compound according to claim 1 wherein one of $R_1$, $R_2$, and $R_3$ in the

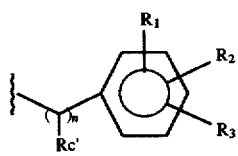

moiety of formula I is H.

3. A compound according to claim 1 wherein two of $R_1$, $R_2$, and $R_3$ in the

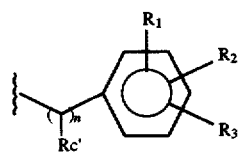

moiety of formula I is H.

4. A compound according to claim 1 wherein all of $R_c$ or all of $R_{c'}$ are H.

5. A compound according to claim 1 wherein $R_4$ is phenyl or

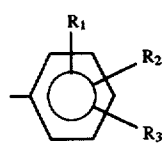

wherein each $R_1$ is independently

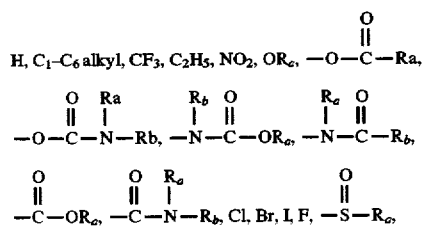

-continued

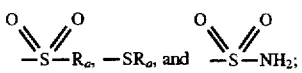

and where $R_a$ is not H in

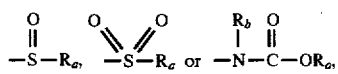

and each $R_2$, and $R_3$ can be independently

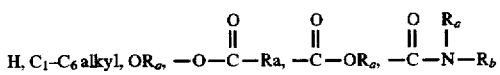

Cl, Br, I, or F;

each $R_a$ and $R_b$ is independently selected from the group consisting of H, $C_1$–$C_6$ alkyl, $CF_3$, $C_2F_5$, phenyl, and benzyl.

6. A compound according to claim 1 wherein $R_5$ is

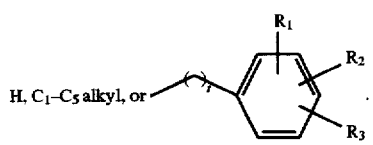

7. A compound according to claim 1 wherein $R_6$ is

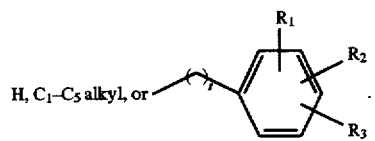

8. A composition comprising a neurokinin antagonistic effective amount of a compound according to claim 1 and a pharmaceutically acceptable carrier material.

9. A compound according to claim 1, wherein n is 0 to 3.

10. A method for for inducing neurokinin antagonism which comprises administering a neurokinin antagonistic effective amount of a compound according to claim 1 to a mammal in need thereof.

11. A method for treating chronic airway diseases selected from the group consisting of asthma and allergies; inflammatory diseases selected from the group consisting of inflammatory bowel disease, psoriasis, fibrositos, osteoarthritis, and rheumatoid arthritis; migraine; central nervous system disorders selected from the group consisting of depression, psychosis, dementia, and Alzheimer's disease; Down's syndrome; neuropathy; multiple sclerosis; ophthalmic disorders; conjunctivitis; auto immune disorders; graft rejection; systemic lupus erythematosus; GI disorders selected from the group consisting of Crohn's disease and ulcerative colitis; disorders of bladder function; circulatory disorders such as angina; Raynaud's disease; coughing and pain comprising administering an effective amount of a compound of claim 1 to a mammal in need of such treatment.

12. A compound selected from the group consisting of
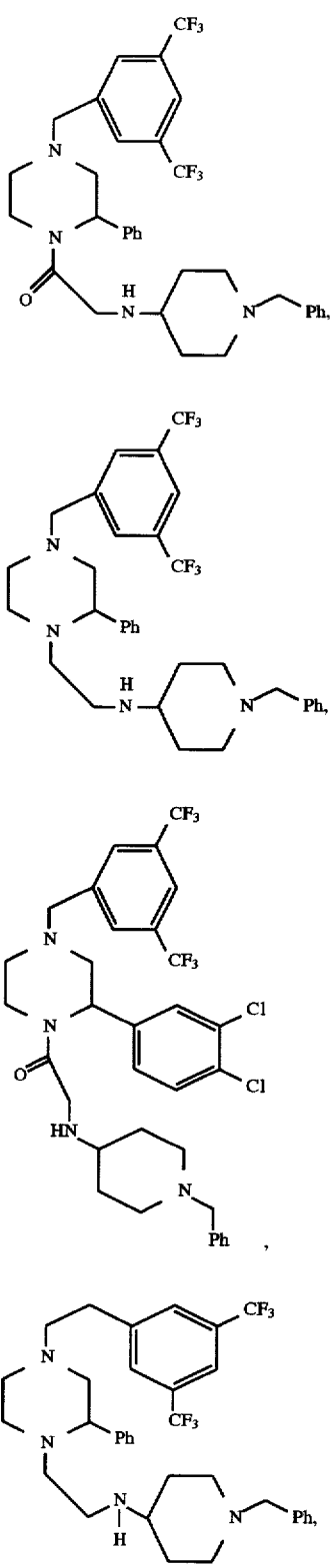
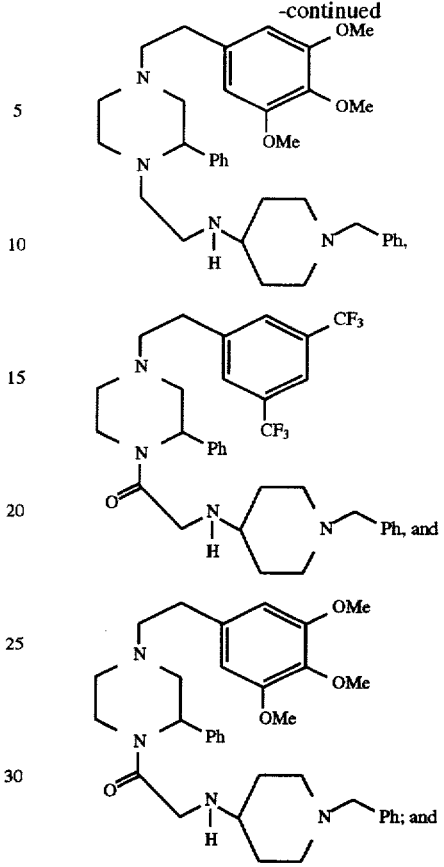
a compound selected from the group consisting of
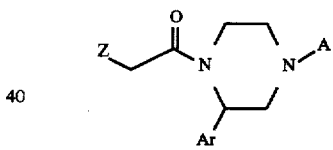
wherein Ar is phenyl or 3,4-dichlorophenyl
| wherein A is | and Z is |
|---|---|
| 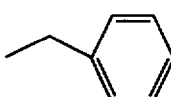 | 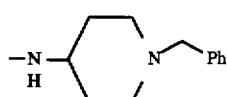 |
| 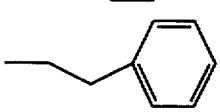 | 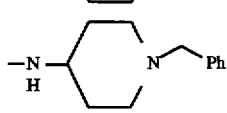 |
|  | |
or a pharmaceutically acceptable salt thereof.
* * * * *